(12) United States Patent
Yashiro et al.

(10) Patent No.: US 10,196,358 B2
(45) Date of Patent: *Feb. 5, 2019

(54) KCNQ2-5 CHANNEL ACTIVATOR

(71) Applicant: Ono Pharmaceutical Co., Ltd., Chuo-ku, Osaka-shi, Osaka (JP)

(72) Inventors: Kentaro Yashiro, Osaka (JP); Daisuke Wakamatsu, Osaka (JP); Tetsuji Saito, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,428

(22) Filed: Aug. 8, 2017

(65) Prior Publication Data

US 2017/0334855 A1 Nov. 23, 2017

Related U.S. Application Data

(63) Continuation of application No. 15/515,243, filed as application No. PCT/JP2015/080034 on Oct. 23, 2015, now Pat. No. 9,809,544.

(30) Foreign Application Priority Data

Oct. 24, 2014 (JP) ................. 2014-217540

(51) Int. Cl.
| | |
|---|---|
| *C07D 213/61* | (2006.01) |
| *A61K 31/44* | (2006.01) |
| *A61K 31/17* | (2006.01) |
| *A61K 31/341* | (2006.01) |
| *A61K 31/351* | (2006.01) |
| *A61K 31/381* | (2006.01) |
| *A61K 31/4045* | (2006.01) |
| *A61K 31/417* | (2006.01) |
| *A61K 31/422* | (2006.01) |
| *A61K 31/4245* | (2006.01) |
| *A61K 31/426* | (2006.01) |
| *A61K 31/435* | (2006.01) |
| *A61K 31/4545* | (2006.01) |
| *A61K 31/4965* | (2006.01) |
| *A61K 31/505* | (2006.01) |
| *C07D 213/74* | (2006.01) |
| *C07D 309/04* | (2006.01) |
| *C07C 275/32* | (2006.01) |
| *C07C 275/40* | (2006.01) |
| *C07D 333/20* | (2006.01) |
| *C07D 333/28* | (2006.01) |

(Continued)

(52) U.S. Cl.
CPC .......... *C07D 213/61* (2013.01); *A61K 31/17* (2013.01); *A61K 31/341* (2013.01); *A61K 31/351* (2013.01); *A61K 31/381* (2013.01); *A61K 31/4045* (2013.01); *A61K 31/417* (2013.01); *A61K 31/422* (2013.01); *A61K 31/426* (2013.01); *A61K 31/4245* (2013.01); *A61K 31/435* (2013.01); *A61K 31/4545* (2013.01); *A61K 31/4965* (2013.01); *A61K 31/505* (2013.01); *C07C 233/26* (2013.01); *C07C 233/29* (2013.01); *C07C 275/32* (2013.01); *C07C 275/40* (2013.01); *C07D 209/30* (2013.01); *C07D 213/40* (2013.01); *C07D 213/74* (2013.01); *C07D 233/64* (2013.01); *C07D 239/26* (2013.01); *C07D 241/12* (2013.01); *C07D 271/06* (2013.01); *C07D 277/28* (2013.01); *C07D 307/52* (2013.01); *C07D 309/04* (2013.01); *C07D 333/20* (2013.01); *C07D 333/28* (2013.01); *C07D 413/06* (2013.01)

(58) Field of Classification Search
None
See application file for complete search history.

(56) References Cited

U.S. PATENT DOCUMENTS 4,058,612 A 11/1977 Neustadt
4,093,742 A 6/1978 Neustadt
(Continued)

FOREIGN PATENT DOCUMENTS

CN 101596191 A 12/2009
GB 1507340 A 4/1978
(Continued)

OTHER PUBLICATIONS

English translation of the Office Action for counterpart Chinese Application No. 201580057252.0, dated Apr. 23, 2018.*
(Continued)

*Primary Examiner* — Zinna Northington Davis
(74) *Attorney, Agent, or Firm* — Foley & Lardner LLP

(57) ABSTRACT

The present invention relates to a compound represented by the general formula (I) (wherein the definition of each group has the same meaning as described in the specification). The compound is useful as preventive and/or therapeutic agent for KCNQ2-5 channel-related diseases.

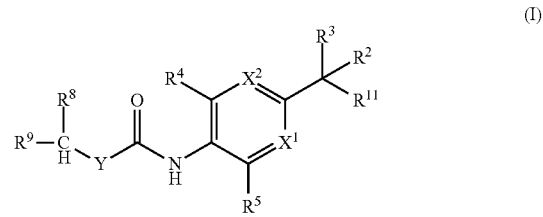

(I)

11 Claims, No Drawings

(51) Int. Cl.

| | |
|---|---|
| *C07D 233/64* | (2006.01) |
| *C07D 239/26* | (2006.01) |
| *C07D 413/06* | (2006.01) |
| *C07D 241/12* | (2006.01) |
| *C07C 233/26* | (2006.01) |
| *C07C 233/29* | (2006.01) |
| *C07D 271/06* | (2006.01) |
| *C07D 277/28* | (2006.01) |
| *C07D 209/30* | (2006.01) |
| *C07D 213/40* | (2006.01) |
| *C07D 307/52* | (2006.01) |

(56) References Cited

U.S. PATENT DOCUMENTS

| | | | |
|---|---|---|---|
| 9,809,544 B2* | 11/2017 | Yashiro | C07D 213/61 |
| 2010/0234429 A1 | 9/2010 | Kuehnert et al. | |

FOREIGN PATENT DOCUMENTS

| | | |
|---|---|---|
| JP | 51-82239 A | 7/1976 |
| JP | 2003-192660 A | 7/2003 |
| JP | 2014-521616 A | 8/2014 |
| WO | WO 02/058698 A2 | 8/2002 |
| WO | WO 03/055848 A2 | 7/2003 |
| WO | WO 2006/029623 A1 | 3/2006 |
| WO | WO 2010/102809 A1 | 9/2010 |
| WO | WO-2011/085351 A2 | 7/2011 |
| WO | WO 2011/085361 A1 | 7/2011 |
| WO | WO 2013/013815 A1 | 1/2013 |
| WO | WO 2013/064450 A1 | 5/2013 |

OTHER PUBLICATIONS

Dalby-Brown, "Kv7 Channels: Function, Pharmacology and Channel Modulators," Current Topics in Medicinal Chemistry, 2006, 6:999-1023.

Liu et al., Chemical Abstracts 164 :326336 of Youji Huazue, 2014, 34(10):2140-2145, Chinese Journal of Organic Chemistry (published online Jun. 11, 2014), 34(10):2140-2145.

Rode et al., "Functional effects of the KCNQ modulators retigabine and XE991 in the rat urinary bladder," European Journal of Pharmacology, 2010, 638:121-127.

Streng et al., "Urodynamic Effects of the K+ Channel (KCNQ) Opener Regitabine in Freely Moving, Conscious Rats," The Journal of Urology, Nov. 2004, 172:2054-2058.

Yu et al., "Discovery, Synthesis, and Structure-Activity Relationship of a Series of N-Aryl-bicyclo[2.2.1]heptane-2-carboxamides: Characterization of ML213 as a Novel KCNQ2 and KCNQ4 Potassium Channel Opener," ACS Chem. Neurosci., 2011, 2:572-577.

* cited by examiner

KCNQ2-5 CHANNEL ACTIVATOR

CROSS-REFERENCE TO RELATED APPLICATIONS

This application is a Continuation of U.S. application Ser. No. 15/515,243, which is the U.S. National Stage application of PCT/JP2015/080034, filed Oct. 23, 2015, which claims priority from Japanese application JP 2014-214540, filed Oct. 24, 2014.

TECHNICAL FIELD

The present invention relates to a compound represented by the general formula (I):

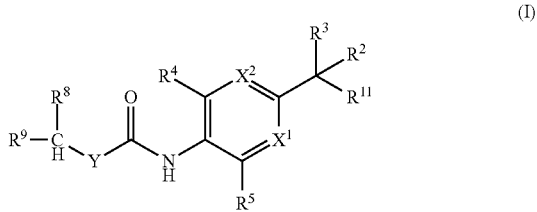

(wherein all the symbols represent the same meanings as given below), a salt thereof, a solvate thereof, or a cocrystal thereof (hereinafter, also abbreviated as the compound of the present invention).

BACKGROUND ART

It has been found that a KCNQ channel has five subtypes including KCNQ1, KCNQ2, KCNQ3, KCNQ4, and KCNQ5. Among them, KCNQs 2-5 other than KCNQ1 are expressed in the nociceptive sensory system such as spinal dorsal root ganglion and spinal cord. The activation of the KCNQ2-5 channel causes hyperpolarization of the nerve cell in a nociceptive signal pathway.

It has been reported that KCNQ2-5 channel activator is useful for treatment for many disorders characterized by neuron excitatory disorders including epilepsy, pain, migraine, and anxiety disorders (see Non-Patent Literature 1). Actually, retigabine as a KCNQ2-5 channel activator has been marketed as an antiepileptic drug.

Furthermore, in recent years, it has been also reported that the retigabine is useful for treatment for urinary bladder disorders (for example, overactive urinary bladder) (see Non-Patent Literatures 2 and 3).

It is considered that since the overactive urinary bladder is caused by potential overactivity of the detrusor muscle, a muscarinic receptor antagonist having an effect of mainly inhibiting contraction of the urinary bladder has been widely used for treatment for overactive urinary bladder. However, the muscarinic receptor is present not only in the urinary bladder but also in the salivary gland, the intestinal tract, the ciliary muscle, and the like, and the muscarinic receptor has also a functional role. Therefore, adverse reactions such as dry mouth, constipation, and nephelopsia may occur concurrently. Furthermore, there is a concern that the effect of inhibiting contraction of the urinary bladder by the muscarinic receptor antagonist may cause adverse reactions such as difficulty of urination, increase in the amount of residual urine, and urodialysis. Therefore, sufficient therapeutic effect cannot be necessarily provided. Furthermore, as a drug to overcome the problems of the muscarinic receptor antagonist, a selective β3 adrenergic receptor agonist was put on the market in 2011 in Japan. It is suggested that the selective β3 adrenergic receptor agonist enhances the urine collection function by relaxing action of the urinary bladder, while it gives less effect on the urination function. Since the selective β3 adrenergic receptor agonist exhibits the relaxing action of the urinary bladder not by contractile stimulation, it is expected to have an effect in a wide range of patients. On the other hand, increase in use increases a risk of Q-T extension and shows increase in the cardiac rate by the effect of β cardiac receptor, and which is a restriction factor of the usage.

As mentioned above, in this region, a drug having a relaxing action of the urinary bladder not by the contractile stimulation, and less adverse reaction have been demanded. The KCNQ2-5 channel activator is expected as a drug that responds to these unmet medical needs.

To date, as a KCNQ activator having a monocyclic amide skeleton, for example, a compound represented by the general formula (a) is known:

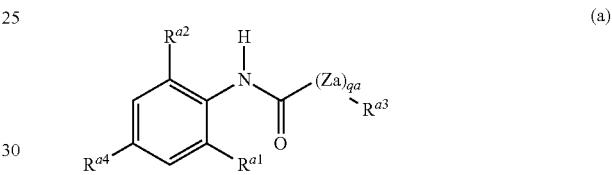

(wherein Za is O or S; qa is 0 or 1; $R^{a1}$ and $R^{a2}$ are each independently selected from the group consisting of halogen, cyano, amino, $C_{1-6}$-alkyl (alkenyl/alkynyl), and the like; $R^{a3}$ is selected from the group consisting of $C_{1-6}$-alkyl (alkenyl/alkynyl), $C_{3-8}$-cycloalkyl (cycloalkenyl), $C_{3-8}$-cycloalkyl (cycloalkenyl)-$C_{1-6}$-alkyl (alkenyl/alkynyl), aryl-$C_{1-6}$-alkyl (alkenyl/alkynyl), aryl-$C_{3-8}$-cycloalkyl (cycloalkenyl), and the like; $R^{a4}$ is selected from the group consisting of halogen, cyano, $C_{1-6}$-alkyl (alkenyl/alkynyl), $C_{3-8}$-cycloalkyl (cycloalkenyl), $C_{3-8}$-cycloalkyl (cycloalkenyl)-$C_{1-6}$-alkyl (alkenyl/alkynyl), and the like (definitions of the groups were partially extracted) (see Patent Literature 1).

However, the compound of the present invention is not included in the general formula (a) of Patent Literature 1. Furthermore, Patent Literature 1 includes neither description nor suggestion of technique of achieving the compound of the present invention from the compound described in the Patent Literature 1.

Furthermore, Patent Literature 2 describes the following compound:

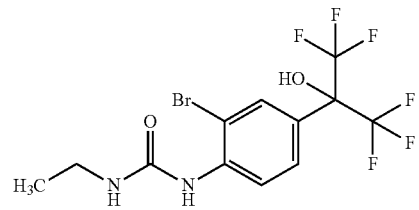 [SMILES: CCNC(=O)Nc1ccc(C(O)(C(F)(F)F)C(F)(F)F)cc1Br]

(N-ethyl-N'-[2-bromo-4-(hexafluoro-2-hydroxy-2-propyl) phenyl]urea). However, Patent Literature 2 relates to a compound having a hypotensive activity, and includes neither description nor suggestion of the KCNQ activity.

CITATION LIST

Patent Literatures

Patent Literature 1: International Publication number WO2006/029623
Patent Literature 2: Japanese Patent Application Unexamined Publication No. S51-82239

Non-Patent Literatures

[Non-Patent Literature 1] Current Topics in Medicinal Chemistry, Vol. 6, p. 999-1023, 2006
[Non-Patent Literature 2] The Journal of Urology, Vol. 172, p. 2054-2058, 2004
[Non-Patent Literature 3] European Journal of Pharmacology, Vol. 638, p. 121-127, 2010

SUMMARY OF THE INVENTION

Technical Problems

An object of the present invention is to provide a compound having a strong opening action with respect to KCNQ2-5 channels.

Solution to Problem

In order to solve the above-mentioned problems, the inventors of the present invention have keenly studied, and as a result, found that the compound of the present invention has a strong opening action with respect to the KCNQ2-5 channels. Furthermore, the present inventors have found that the compound of the present invention is excellent in solubility, stability and/or safety. Thus, the present inventors have completed the present invention.

That is to say, the present invention relates to
(1) a compound represented by the general formula (1):

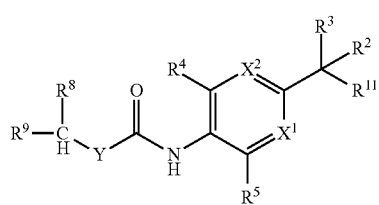

(wherein $X^1$ is (1) a nitrogen atom or (2) C—$R^6$; $X^2$ is (1) a nitrogen atom or (2) C—$R^7$; $R^{11}$ is (1) $OR^1$ or (2) $NH_2$; $R^1$ is (1) a hydrogen atom or (2) a C1-4 alkyl group; $R^2$ and $R^3$ are each independently (1) a hydrogen atom, or (2) a C1-4 alkyl group which may be substituted with halogen, where both $R^2$ and $R^3$ are not simultaneously a hydrogen atom; $R^4$, $R^5$, $R^6$, and $R^7$ are each independently (1) a hydrogen atom, (2) halogen, (3) a C1-4 alkyl group which may be substituted with halogen, or (4) a C1-4 alkoxy group which may be substituted with halogen, where both $R^4$ and $R^5$ are not simultaneously a hydrogen atom; Y is (1) —NH—, (2) —O—, or (3) a bond; $R^8$ is (1) a hydrogen atom or (2) a C1-4 alkyl group which may be substituted with halogen or a hydroxy group; $R^9$ is (1) a ring A, (2) a C1-6 alkyl group, (3) a C2-6 alkenyl group, (4) a C2-6 alkynyl group, (5) —C1-4 alkylene group-ring A, (6) —C2-4 alkenylene group-ring A, (7) —C2-4 alkynylene group-ring A, (8) -ring B-ring C, (9) -ring B-C1-4 alkylene group-ring C, (10) -ring B-C2-4 alkenylene group-ring C, (11) -ring B-C2-4 alkynylene group-ring C, or (12) -ring B-O-ring C, where the alkyl group, alkenyl group, alkynyl group, alkylene group, alkenylene group or alkynylene group each may be substituted with halogen or a hydroxy group; the ring A is (1) C3-8 cycloalkane, (2) 3- to 8-membered heterocycloalkane, (3) a C3-12 monocyclic or bicyclic unsaturated carbocyclic ring, or which may be partially saturated, or (4) 3- to 12-membered monocyclic or bicyclic unsaturated heterocycle including one to four heteroatoms selected from an oxygen atom, a nitrogen atom, and a sulfur atom, or which may be partially saturated; ring B and ring C are each independently (1) C3-8 cycloalkane, (2) 3- to 8-membered heterocycloalkane, (3) a C3-7 monocyclic unsaturated carbocyclic ring, or which may be partially saturated, or (4) 3- to 7-membered monocyclic unsaturated heterocycle including one to three heteroatoms selected from an oxygen atom, a nitrogen atom and a sulfur atom, or which may be partially saturated; where the ring A, ring B and ring C each independently may be substituted with one to five $R^{10}$, and when a plurality of $R^{10}$ is present, the plurality of $R^{10}$ may be the same as or different from each other; $R^{10}$ (1) halogen, (2) a hydroxy group, (3) a cyano group, (4) a C1-6 alkyl group which may be substituted with halogen or a hydroxy group, (5) a C1-6 alkoxy group which may be substituted with halogen or a hydroxy group, or (6) an amino group which may be substituted with a C1-4 alkyl group or a C2-5 acyl group) (excluding N-ethyl-N'-[2-bromo-4-(hexafluoro-2-hydroxy-2-propyl)phenyl]urea), a salt thereof, a solvate thereof, or a cocrystal thereof;

(2) the compound described in the above (1), wherein Y is —NH— or a bond, a salt thereof, a solvate thereof, or a cocrystal thereof;

(3) the compound described in the above (1) or (2), wherein $X^1$ is C—$R^6$, and $X^2$ is C—$R^7$, a salt thereof, a solvate thereof, or a cocrystal thereof;

(4) the compound described in any one of the above (1) to (3), which is represented by the general formula (II):

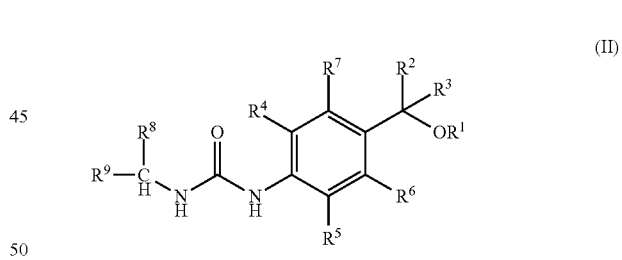

(wherein the symbols represent the same meaning as described in the above (1)), a salt thereof, a solvate thereof, or a cocrystal thereof;

(5) the compound described in any one of the above (1) to (4), wherein $R^1$ is a hydrogen atom, a salt thereof, a solvate thereof, or a cocrystal thereof;

(6) the compound described in any one of the above (1) to (5), wherein one of $R^2$ and $R^3$ is a methyl group which may be substituted with halogen, and the other is a hydrogen atom or a methyl group which may be substituted with halogen, a salt thereof, a solvate thereof, or a cocrystal thereof;

(7) the compound described in any one of the above (1) to (6), wherein $R^6$ is a hydrogen atom or halogen, and $R^7$ is a hydrogen atom, a salt thereof, a solvate thereof, or a cocrystal thereof;

(8) the compound described in any one of the above (1) to (7), which is represented by the general formula (II-1):

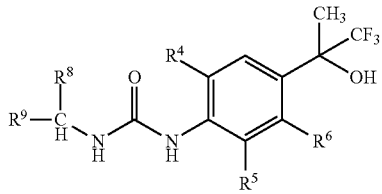

(II-1)

(wherein R⁶ is a hydrogen atom or halogen, and the other symbols represent the same meaning as described in the above (1)), a salt thereof, a solvate thereof, or a cocrystal thereof;

(9) the compound described in any one of the above (1) to (7), which is represented by the general formula (II-2):

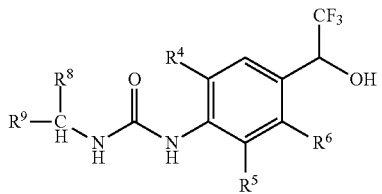

(II-2)

(wherein R⁶ is a hydrogen atom or halogen, and the other symbols represent the same meaning as described in the above (1)), a salt thereof, a solvate thereof, or a cocrystal thereof;

(10) the compound described in any one of the above (1) to (9), wherein R⁴ and R⁵ are each independently halogen or a methyl group, a salt thereof, a solvate thereof, or a cocrystal thereof;

(11) the compound described in any one of the above (1) to (10), wherein R⁸ is a hydrogen atom or a methyl group, a salt thereof, a solvate thereof, or a cocrystal thereof;

(12) the compound described in the above (1), wherein the compound is:
(1)  1-{2,6-dichloro-4-[(2R)-1,1,1-trifluoro-2-hydroxy-2-propanyl]phenyl}-3-{[5-(trifluoromethyl)-2-pyridinyl]methyl}urea,
(2)  1-{2,6-dichloro-4-[(2R)-1,1,1-trifluoro-2-hydroxy-2-propanyl]phenyl}-3-{[5-(trifluoromethyl)-2-pyrimidinyl]methyl}urea,
(3)  1-{2,6-dichloro-4-[(2R)-1,1,1-trifluoro-2-hydroxy-2-propanyl]phenyl}-3-{[6-(trifluoromethyl)-3-pyridinyl]methyl}urea,
(4)  1-[(5-chloro-2-pyridinyl)methyl]-3-{2,6-dichloro-4-[(2R)-1,1,1-trifluoro-2-hydroxy-2-propanyl]phenyl}urea,
(5)  1-{2,6-dichloro-4-[(2R)-1,1,1-trifluoro-2-hydroxy-2-propanyl]phenyl}-3-{[3-(trifluoromethyl)-1,2,4-oxadiazole-5-yl]methyl}urea,
(6)  1-{2,6-dichloro-4-[(2S)-1,1,1-trifluoro-2-hydroxy-2-propanyl]phenyl}-3-{[5-(trifluoromethyl)-2-pyrimidinyl]methyl}urea,
(7)  1-{2,6-dichloro-4-[(2S)-1,1,1-trifluoro-2-hydroxy-2-propanyl]phenyl}-3-{[6-(trifluoromethyl)-3-pyridinyl]methyl}urea,
(8)  1-[(5-chloro-2-pyridinyl)methyl]-3-{2,6-dichloro-4-[(2S)-1,1,1-trifluoro-2-hydroxy-2-propanyl]phenyl}urea,
(9)  1-{2,6-dichloro-4-[(2S)-1,1,1-trifluoro-2-hydroxy-2-propanyl]phenyl}-3-{[3-(trifluoromethyl)-1,2,4-oxadiazole-5-yl]methyl}urea,
(10)  1-{2,6-dichloro-4-[(1R)-2,2,2-trifluoro-1-hydroxyethyl]phenyl}-3-{[3-(trifluoromethyl)-1,2,4-oxadiazole-5-yl]methyl}urea,
(11)  1-{2,6-dichloro-4-[(1R)-2,2,2-trifluoro-1-hydroxyethyl]phenyl}-3-{[2-(trifluoromethyl)-5-pyrimidinyl]methyl}urea,
(12)  1-{2,6-dichloro-4-[(1R)-2,2,2-trifluoro-1-hydroxyethyl]phenyl}-3-{[5-(trifluoromethyl)-2-pyrimidinyl]methyl}urea,
(13)  1-{2,6-dichloro-4-[(1R)-2,2,2-trifluoro-1-hydroxyethyl]phenyl}-3-{[2-(trifluoromethyl)-1,3-thiazole-5-yl]methyl}urea,
(14)  1-{2,6-dichloro-4-[(1S)-2,2,2-trifluoro-1-hydroxyethyl]phenyl}-3-{[3-(trifluoromethyl)-1,2,4-oxadiazole-5-yl]methyl}urea,
(15)  1-{2,6-dichloro-4-[(1S)-2,2,2-trifluoro-1-hydroxyethyl]phenyl}-3-{[2-(trifluoromethyl)-5-pyrimidinyl]methyl}urea,
(16)  1-{2,6-dichloro-4-[(1S)-2,2,2-trifluoro-1-hydroxyethyl]phenyl}-3-{[2-(trifluoromethyl)-1,3-thiazole-5-yl]methyl}urea,
(17)  1-{2,6-dichloro-4-[(2S)-1,1,1-trifluoro-2-hydroxy-2-propanyl]phenyl}-3-{[5-(trifluoromethyl)-2-pyridinyl]methyl}urea, or
(18)  1-{2,6-dichloro-4-[(1S)-2,2,2-trifluoro-1-hydroxyethyl]phenyl}-3-{[5-(trifluoromethyl)-2-pyridinyl]methyl}urea,
a salt thereof, a solvate thereof, or a cocrystal thereof;
(13) a pharmaceutical composition comprising a compound represented by the general formula (I), a salt thereof, a solvate thereof, or a cocrystal thereof, and a pharmaceutically acceptable carrier;
(14) the pharmaceutical composition described in the above (13), which is a preventive and/or therapeutic agent for a KCNQ2-5 channel-related disease;
(15) the pharmaceutical composition described in the above (14), wherein the KCNQ2-5 channel-related disease is dysuria;
(16) the pharmaceutical composition described in the above (15), the dysuria is overactive urinary bladder;
(17) a method for preventing and/or treating a KCNQ2-5 channel-related disease, the method comprising: administering an effective amount of the compound represented by the general formula (I), a salt thereof, a solvate thereof, or a cocrystal thereof, to a mammal;
(18) a compound represented by the general formula (I), a salt thereof, a solvate thereof, or a cocrystal thereof, for preventing and/or treating a KCNQ2-5 channel-related disease;
(19) use of a compound represented by the general formula (I), a salt thereof, a solvate thereof, or a cocrystal thereof, for producing a preventive and/or therapeutic agent for a KCNQ2-5 channel-related disease;
(20) a compound represented by the general formula (I-1):

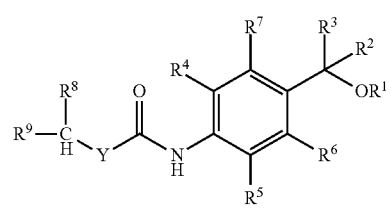

(I-1)

(wherein $R^1$ is (1) a hydrogen atom or (2) a C1-4 alkyl group; $R^2$ and $R^3$ are each independently (1) a hydrogen atom, or (2) a C1-4 alkyl group which may be substituted with halogen, where both $R^2$ and $R^3$ are not simultaneously a hydrogen atom; $R^4$ and $R^5$ are each independently (1) a hydrogen atom, (2) halogen, (3) a C1-4 alkyl group which may be substituted with halogen, or (4) a C1-4 alkoxy group which may be substituted with halogen, where both $R^4$ and $R^5$ are not simultaneously a hydrogen atom; $R^6$, and $R^7$ are each independently a hydrogen atom or halogen; Y is (1) —NH—, (2) —CH$_2$—, (3) —O—, or (4) a bond; $R^8$ is (1) a hydrogen atom or (2) a C1-4 alkyl group which may be substituted with halogen or a hydroxy group; $R^9$ is (1) a ring A, (2) a C1-6 alkyl group, (3) a C2-6 alkenyl group, (4) a C2-6 alkynyl group, (5) —C1-4 alkylene group-ring A, (6) —C2-4 alkenylene group-ring A, (7) —C2-4 alkynylene group-ring A, (8) -ring B-ring C, (9) -ring B-C1-4 alkylene group-ring C, (10) -ring B-C2-4 alkenylene group-ring C, or (11) -ring B-C2-4 alkynylene group-ring C, where the alkyl group, alkenyl group, alkynyl group, alkylene group, alkenylene group or alkynylene group each may be substituted with halogen or a hydroxy group; the ring A is (1) C3-8 cycloalkane, (2) 3- to 8-membered heterocycloalkane, (3) a C5-12 monocyclic or bicyclic unsaturated carbocyclic ring, or which may be partially saturated, or (4) 5- to 12-membered monocyclic or bicyclic unsaturated heterocycle including one to four heteroatoms selected from an oxygen atom, a nitrogen atom, and a sulfur atom, or which may be partially saturated; ring B and ring C are each independently (1) C3-8 cycloalkane, (2) 3- to 8-membered heterocycloalkane, (3) a C5-7 monocyclic unsaturated carbocyclic ring, or which may be partially saturated, or (4) 5- to 7-membered monocyclic unsaturated heterocycle including one to three heteroatoms selected from an oxygen atom, a nitrogen atom and a sulfur atom, or which may be partially saturated; where the ring A, ring B and ring C each independently may be substituted with one to five $R^{10}$, and when a plurality of $R^{10}$ is present, the plurality of $R^{10}$ may be the same as or different from each other; $R^{10}$ is (1) halogen, (2) a hydroxy group, (3) a cyano group, (4) a C1-6 alkyl group which may be substituted with halogen or a hydroxy group, or (5) a C1-6 alkoxy group which may be substituted with halogen or a hydroxy group), a salt thereof, a solvate thereof, or a cocrystal thereof;

(21) the compound described in the above (20), wherein Y is —NH—, —CH$_2$—, or a bond, a salt thereof, a solvate thereof, or a cocrystal thereof;

(22) the compound described in the above (20) or (21), which is represented by the general formula (II):

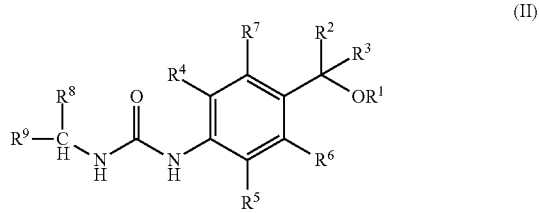

(II)

(wherein the symbols represent the same meaning as described in the above (20)), a salt thereof, a solvate thereof, or a cocrystal thereof;

(23) the compound described in any one of the above (20) to (22), wherein $R^1$ is a hydrogen atom, a salt thereof, a solvate thereof, or a cocrystal thereof;

(24) the compound described in any one of the above (20) to (23), wherein one of $R^2$ and $R^3$ is a methyl group which may be substituted with halogen, and the other is a methyl group which may be substituted with a hydrogen atom or halogen a salt thereof, a solvate thereof, or a cocrystal thereof;

(25) the compound described in any one of the above (20) to (24), wherein $R^7$ is a hydrogen atom, a salt thereof, a solvate thereof, or a cocrystal thereof;

(26) the compound described in any one of the above (20) to (25), which is represented by the general formula (II-1):

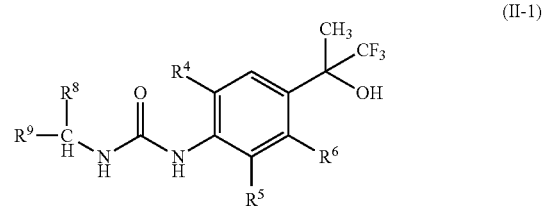

(II-1)

(wherein the symbols represent the same meaning as described in the above (20)), a salt thereof, a solvate thereof, or a cocrystal thereof;

(27) the compound described in any one of the above (20) to (25), which is represented by the general formula (II-2):

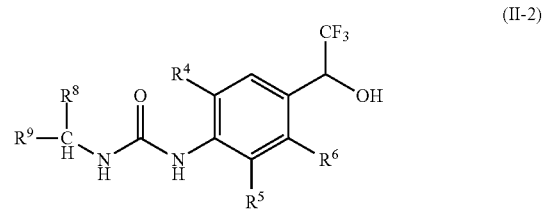

(II-2)

(wherein the symbols represent the same meaning as described in the above (20)), a salt thereof, a solvate thereof, or a cocrystal thereof;

(28) the compound described in any one of the above (20) to (27), wherein $R^4$ and $R^5$ are each independently halogen or a methyl group, a salt thereof, a solvate thereof, or a cocrystal thereof;

(29) the compound described in any one of the above (20) to (28), wherein $R^8$ is a hydrogen atom or a methyl group, a salt thereof, a solvate thereof, or a cocrystal thereof, and the like.

Advantageous Effects of the Invention

The compound of the present invention is useful as preventive and/or therapeutic agent for KCNQ2-5 channel-related diseases.

DESCRIPTION OF EMBODIMENTS

Hereinafter, the present invention is described in detail.

In the present invention, the C1-4 alkyl group means a straight or a branched C1-4 alkyl group. Examples of the C1-4 alkyl group include methyl, ethyl, propyl, isopropyl, butyl, sec-butyl, and tert-butyl.

In the present invention, the C2-4 alkyl group means a straight or a branched C2-4 alkyl group. Examples of the C2-4 alkyl group include ethyl, propyl, isopropyl, butyl, sec-butyl, and tert-butyl.

In the present invention, the C1-6 alkyl group means a straight or a branched C1-6 alkyl group. Examples of the C1-6 alkyl group include methyl, ethyl, propyl, isopropyl, butyl, sec-butyl, tert-butyl, pentyl, isopentyl, tert-pentyl, neopentyl, hexyl, isohexyl, 3-methyl pentyl, and the like.

In the present invention, the C2-5 acyl group means a straight or a branched C2-5 acyl group. Examples of the C2-5 acyl group include acetyl, propionyl, butanoyl, pentanoyl, and the like.

In the present invention, the C2-6 alkenyl group means a straight or a branched C2-6 alkenyl group having at least one carbon-carbon double bond. Examples of the C2-6 alkenyl group include ethenyl, 1-propene-1-yl, 1-propene-2-yl, 2-propene-1-yl, 1-butene-1-yl, 1-butene-2-yl, 3-butene-1-yl, 3-butene-2-yl, 2-butene-1-yl, 2-butene-2-yl, 2-methyl-1-propene-1-yl, 2-methyl-2-propene-1-yl, 1,3-butadiene-1-yl, 1,3-butadiene-2-yl, and the like.

In the present invention, the C2-6 alkynyl group means a straight or a branched C2-6 alkynyl group having at least one carbon-carbon triple bond. Examples of the C2-6 alkynyl group include ethynyl, 1-propyne-1-yl, 2-propyne-1-yl, 1-butyne-1-yl, 3-butyne-1-yl, 3-butyne-2-yl, 2-butyne-1-yl, and the like.

In the present invention, the C1-4 alkylene group means a straight or a branched C1-4 alkylene group. Examples of the C1-4 alkylene group include methylene, ethylene, methyl methylene, ethyl methylene, propylene, butylene, isopropylene, isobutylene, sec-butylene, tert-butylene, and the like.

In the present invention, the C2-4 alkenylene group means a straight or a branched C2-4 alkenylene group. Examples of the C2-4 alkenylene group include ethenylene, 1-propenylene, 2-propenylene, 1-butenylene, 2-butenylene, 3-butenylene, and the like.

In the present invention, the C2-4 alkynylene group means a straight or a branched C2-4 alkynylene group. Examples of the C2-4 alkynylene group include ethynylene, 1-propynylene, 2-propynylene, 1-buthynylene, 2-buthynylene, 3-buthynylene, and the like.

In the present invention, the C1-4 alkoxy group means a straight or a branched C1-4 alkoxy group. Examples of the C1-4 alkoxy group include methoxy, ethoxy, propoxy, isopropoxy, butoxy, isobutyloxy, tert-butoxy, and the like.

In the present invention, C1-6 alkoxy group means a straight or a branched C1-6 alkoxy group. Examples of the C1-6 alkoxy group include methoxy, ethoxy, propoxy, isopropoxy, butoxy, isobutyloxy, tert-butoxy, pentyloxy, isopentyloxy, tert-pentyloxy, neopentyloxy, hexyloxy, and the like.

In the present invention, halogen means fluorine, chlorine, bromine, iodine, and the like.

In the present invention, the C3-8 cycloalkane is a C3-8 saturated hydrocarbon ring, and may include a spiro bond or cross-linking. Examples of the C3-8 cycloalkane include cyclopropane, cyclobutane, cyclopentane, cyclohexane, bicyclo[2.2.1]heptane, bicyclo[3.1.1]heptane, bicyclo[2.2.2]octane, cycloheptane, cyclooctane, perhydropentalene, cubane, and the like.

In the present invention, specific examples of the C3-8 monocyclic cycloalkane include cyclopropane, cyclobutane, cyclopentane, cyclohexane, cycloheptane, and cyclooctane.

In the present invention, specific examples of the C3-6 monocyclic cycloalkane include cyclopropane, cyclobutane, cyclopentane, and cyclohexane.

In the present invention, the 3- to 8-membered heterocycloalkane is a 3- to 8-membered saturated heterocycle including one to three heteroatoms selected from an oxygen atom, a nitrogen atom and a sulfur atom, and may include a spiro bond or cross-linking. Specific examples of the 3- to 8-membered heterocycloalkane include aziridine, oxirane, thiirane, azetidine, oxetane, thietane, pyrrolidine, tetrahydrofuran, tetrahydrothiophene, piperidine, tetrahydropyran, tetrahydrothiopyran, azabicyclo[2.2.1]heptane, oxabicyclo[2.2.1]heptane, azabicyclo[3.1.1]heptane, azabicyclo[2.2.2]octane, perhydroazepine, perhydrooxepin, perhydrothiepin, azabicyclo[3.2.1]octane, oxabicyclo[3.2.1]octane, imidazolidine, pyrazolidine, tetrahydro-oxazole (oxazolidine), tetrahydroisoxazole (isoxazolidine), tetrahydrothiazole (thiazolidine), tetrahydro-isothiazole (isothiazolidine), dioxolane, dithiolane, piperazine, perhydropyrimidine, perhydropyridazine, tetrahydroxazine, tetrahydrothiazine, morpholine, thiomorpholine, oxathiane, dioxane, dithiane, diazabicyclo[2.2.2]octane, perhydrodiazepine, perhydrooxazepine, perhydrothiazepine, triazolidine, tetrahydrofurazan, tetrahydrooxadiazole (oxadiazolidine), tetrahydrothiadiazole (thiadiazolidine), tetrahydro-oxadiazine, tetrahydrothiadiazine, perhydro-oxadiazepine, perhydrothiadiazepine, and the like.

In the present invention, specific examples of the 3- to 7-membered monocyclic heterocycloalkane including one oxygen atom as the heteroatom include oxirane, oxetane, tetrahydrofuran, tetrahydropyran, perhydrooxepin, and the like.

In the present invention, specific examples of the 3- to 7-membered monocyclic heterocycloalkane including one oxygen atom or nitrogen atom as the heteroatom include aziridine, oxirane, azetidine, oxetane, pyrrolidine, tetrahydrofuran, piperidine, tetrahydropyran, perhydroazepine, perhydrooxepin, and the like.

In the present invention, specific examples of the 3- to 7-membered monocyclic heterocycloalkane including one nitrogen atom as the heteroatom include aziridine, azetidine, pyrrolidine, piperidine, perhydroazepine, and the like.

In the present invention, specific examples of the "C3-12 monocyclic or bicyclic unsaturated carbocyclic ring, or which may be partially saturated" include cyclopropene, cyclobutene, cyclopentene, cyclopentadiene, cyclohexene, cyclohexadiene, benzene, cycloheptene, cycloheptadiene, cyclooctene, cyclooctadiene, pentalene, indene, indan, dihydronaphthalene, tetrahydronaphthalene, azulene, naphthalene, heptalene, and the like.

In the present invention, specific examples of the "C5-12 monocyclic or bicyclic unsaturated carbocyclic ring or which may be partially saturated" include cyclopentene, cyclopentadiene, cyclohexene, cyclohexadiene, benzene, cycloheptene, cycloheptadiene, cyclooctene, cyclooctadiene, pentalene, indene, indan, dihydronaphthalene, tetrahydronaphthalene, azulene, naphthalene, heptalene, and the like.

In the present invention, specific examples of the "C3-7 monocyclic unsaturated carbocyclic ring or which may be partially saturated" include cyclopropene, cyclobutene, cyclopentene, cyclopentadiene, cyclohexene, cyclohexadiene, benzene, cycloheptene, cycloheptadiene, and the like.

In the present invention, specific examples of the "C5-7 monocyclic unsaturated carbocyclic ring or which may be partially saturated" include cyclopentene, cyclopentadiene, cyclohexene, cyclohexadiene, benzene, cycloheptene, cycloheptadiene, and the like.

In the present invention, specific examples of the "C5-6 monocyclic unsaturated carbocyclic ring or which may be partially saturated" include cyclopentene, cyclopentadiene, cyclohexene, cyclohexadiene, benzene, and the like.

In the present invention, specific examples of the "C8-10 bicyclic unsaturated carbocyclic ring or which may be partially saturated" include pentalene, indene, indan, dihydronaphthalene, tetrahydronaphthalene, azulene, naphthalene, and the like.

In the present invention, specific examples of the "3- to 12-membered monocyclic or bicyclic unsaturated heterocycle including one to four heteroatoms selected from an oxygen atom, a nitrogen atom, and a sulfur atom, or which may be partially saturated" include azirine, oxirene, thiirene, azete, pyrroline, imidazoline, triazoline, tetrazoline, pyrazoline, dihydrofuran, dihydrothiophene, dihydrooxazole, dihydroisoxazole, dihydrothiazole, dihydroisothiazole, dihydrofurazan, dihydrooxadiazole, dihydrothiadiazole, pyrrole, imidazole, triazol, tetrazole, pyrazole, furan, thiophene, oxazole, isoxazole, thiazole, isothiazole, furazan, oxadiazole, thiadiazole, pyran, thiopyran, oxazine, oxadiazine, thiazine, thiadiazine, dihydropyridine, tetrahydropyridine, dihydropyrazine, tetrahydropyrazine, dihydropyrimidine, tetrahydropyrimidine, dihydropyridazine, tetrahydropyridazine, dihydropyran, dihydrothiopyran, dihydrooxazine, dihydrooxadiazine, dihydrothiazine, dihydrothiadiazine, pyridine, pyrazine, pyrimidine, pyridazine, azepine, diazepine, oxepin, thiepin, oxazepine, oxadiazepine, thiazepine, thiadiazepin, dihydroazepine, tetrahydroazepine, dihydrodiazepine, tetrahydrodiazepine, dihydrooxepin, tetrahydrooxepin, dihydrothiepin, tetrahydrothiepin, dihydrooxazepine, tetrahydrooxazepine, dihydrooxadiazepine, tetrahydrooxadiazepine, dihydrothiazepine, tetrahydrothiazepine, dihydrothiadiazepine, tetrahydrothiadiazepine, indolizine, indoline, isoindoline, dihydrobenzofuran, dihydroisobenzofuran, dihydrobenzothiophene, dihydroisobenzothiophene, dihydroindazole, dihydrobenzoxazole, dihydrobenzothiazole, dihydrobenzimidazole, dioxaindan, benzodithiolane, indole, isoindole, benzofuran, isobenzofuran, benzothiophene, isobenzothiophene, indazole, purine, benzoxazole, benzothiazole, benzimidazole, benzofurazan, benzothiadiazole, benzotriazol, dithianaphthalene, quinolizine, chromene, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzooxathiane, dihydrobenzooxazine, dihydrobenzothiazine, pyrazinomorpholine, benzodioxan, chroman, benzodithiane, quinoline, isoquinoline, phthalazine, pteridine, naphthyridine, quinoxaline, quinazoline, cinnoline, benzooxepin, benzooxazepine, benzooxadiazepine, benzothiepin, benzothiazepine, benzothiadiazepine, benzoazepine, benzodiazepine, dihydrobenzoazepine, tetrahydrobenzoazepine, dihydrobenzodiazepine, tetrahydrobenzodiazepine, benzodioxepane, dihydrobenzooxazepine, tetrahydrobenzooxazepine, and the like.

In the present invention, specific examples of the "5- to 12-membered monocyclic or bicyclic unsaturated heterocycle including one to four heteroatoms selected from an oxygen atom, a nitrogen atom and a sulfur atom, or which may be partially saturated" include pyrroline, imidazoline, triazoline, tetrazoline, pyrazoline, dihydrofuran, dihydrothiophene, dihydrooxazole, dihydroisoxazole, dihydrothiazole, dihydroisothiazole, dihydrofurazan, dihydrooxadiazole, dihydrothiadiazole, pyrrole, imidazole, triazol, tetrazole, pyrazole, furan, thiophene, oxazole, isoxazole, thiazole, isothiazole, furazan, oxadiazole, thiadiazole, pyran, thiopyran, oxazine, oxadiazine, thiazine, thiadiazine, dihydropyridine, tetrahydropyridine, dihydropyrazine, tetrahydropyrazine, dihydropyrimidine, tetrahydropyrimidine, dihydropyridazine, tetrahydropyridazine, dihydropyran, dihydrothiopyran, dihydrooxazine, dihydrooxadiazine, dihydrothiazine, dihydrothiadiazine, pyridine, pyrazine, pyrimidine, pyridazine, azepine, diazepine, oxepin, thiepin, oxazepine, oxadiazepine, thiazepine, thiadiazepine, dihydroazepine, tetrahydroazepine, dihydrodiazepine, tetrahydrodiazepine, dihydrooxepin, tetrahydrooxepin, dihydrothiepin, tetrahydrothiepin, dihydrooxazepine, tetrahydrooxazepine, dihydrooxadiazepine, tetrahydrooxadiazepine, dihydrothiazepine, tetrahydrothiazepine, dihydrothiadiazepine, tetrahydrothiadiazepine, indolizine, indoline, isoindoline, dihydrobenzofuran, dihydroisobenzofuran, dihydrobenzothiophene, dihydroisobenzothiophene, dihydroindazole, dihydrobenzoxazole, dihydrobenzothiazole, dihydrobenzimidazole, dioxaindan, benzodithiolane, indole, isoindole, benzofuran, isobenzofuran, benzothiophene, isobenzothiophene, indazole, purine, benzoxazole, benzothiazole, benzimidazole, benzofurazan, benzothiadiazole, benzotriazol, dithianaphthalene, quinolizine, chromene, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzooxathiane, dihydrobenzooxazine, dihydrobenzothiazine, pyrazinomorpholine, benzodioxan, chroman, benzodithiane, quinoline, isoquinoline, phthalazine, pteridine, naphthyridine, quinoxaline, quinazoline, cinnoline, benzooxepin, benzooxazepine, benzooxadiazepine, benzothiepin, benzothiazepine, benzothiadiazepine, benzoazepine, benzodiazepine, dihydrobenzoazepine, tetrahydrobenzoazepine, dihydrobenzodiazepine, tetrahydrobenzodiazepine, benzodioxepane, dihydrobenzooxazepine, tetrahydrobenzooxazepine, and the like.

In the present invention, specific examples of the "3- to 7-membered monocyclic unsaturated heterocycle including one to three heteroatoms selected from an oxygen atom, a nitrogen atom, and a sulfur atom, or which may be partially saturated" include azirine, oxirene, thiirene, azete, pyrroline, dihydrofuran, dihydrothiophene, pyrrole, furan, thiophene, pyran, thiopyran, dihydropyridine, tetrahydropyridine, dihydropyran, dihydrothiopyran, pyridine, azepine, oxepin, thiepin, dihydroazepine, tetrahydroazepine, dihydrooxepin, tetrahydrooxepin, dihydrothiepin, tetrahydrothiepin, imidazoline, pyrazoline, dihydrooxazole, dihydroisoxazole, dihydrothiazole, dihydroisothiazole, imidazole, pyrazole, oxazole, isoxazole, thiazole, isothiazole, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, pyrazine, pyrimidine, pyridazine, diazepine, oxazepine, thiazepine, dihydrodiazepine, tetrahydrodiazepine, dihydrooxazepine, tetrahydrooxazepine, dihydrothiazepine, tetrahydrothiazepine, triazoline, dihydrofurazan, dihydrooxadiazole, dihydrothiadiazole, triazol, furazan, oxadiazole, thiadiazole, oxadiazine, thiadiazine, dihydrooxadiazine, dihydrothiadiazine, oxadiazepine, thiadiazepine, dihydrooxadiazepine, tetrahydrooxadiazepine, dihydrothiadiazepine, tetrahydrothiadiazepine, and the like.

In the present invention, specific examples of the "5- to 7-membered monocyclic unsaturated heterocycle including one to three heteroatoms selected from an oxygen atom, a nitrogen atom and a sulfur atom, or which may be partially saturated" include pyrroline, dihydrofuran, dihydrothiophene, pyrrole, furan, thiophene, pyran, thiopyran, dihydropyridine, tetrahydropyridine, dihydropyran, dihydrothiopyran, pyridine, azepine, oxepin, thiepin, dihydroazepine, tetrahydroazepine, dihydrooxepin, tetrahydrooxepin, dihydrothiepin, tetrahydrothiepin, imidazoline, pyrazoline, dihydrooxazole, dihydroisoxazole, dihydrothiazole, dihydroisothiazole, imidazole, pyrazole, oxazole, isoxazole, thiazole, isothiazole, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, pyrazine, pyrimidine, pyridazine, diazepine, oxazepine, thiazepine, dihydrodiazepine, tetrahydrodiazepine, dihydrooxazepine, tetrahydrooxazepine, dihydrothiazepine, tetrahydrothiazepine, triazoline, dihydrofurazan, dihydrooxadiazole, dihydrothiadiazole, triazol, furazan, oxadiazole, thiadiazole, oxadiazine, thiadiazine, dihydrooxadiazine, dihydrothiadiazine, oxadiazepine, thiadiazepine, dihydrooxadiazepine, tetrahydrooxadiazepine, dihydrothiadiazepine, tetrahydrothiadiazepine, and the like.

In the present invention, specific examples of the "5- to 6-membered monocyclic unsaturated heterocycle including one to three heteroatoms selected from an oxygen atom, a nitrogen atom and a sulfur atom, or which may be partially saturated" include pyrroline, dihydrofuran, dihydrothiophene, imidazoline, pyrazoline, dihydrooxazole, dihydroisoxazole, dihydrothiazole, dihydroisothiazole, triazoline, dihydrofurazan, dihydrooxadiazole, dihydrothiadiazole, pyran, thiopyran, dihydropyridine, tetrahydropyridine, dihydropyran, dihydrothiopyran, oxazine, thiazine, dihydropyrazine, tetrahydropyrazine, dihydropyrimidine, tetrahydropyrimidine, dihydropyridazine, tetrahydropyridazine, dihydrooxazine, dihydrothiazine, oxadiazine, thiadiazine, dihydrooxadiazine, dihydrothiadiazine, pyrrole, furan, thiophene, imidazole, pyrazole, oxazole, isoxazole, thiazole, isothiazole, triazol, furazan, oxadiazole, thiadiazole, pyridine, pyrazine, pyrimidine, pyridazine, and the like.

In the present invention, specific examples of the "5- to 6-membered unsaturated heterocycle including one to three heteroatoms selected from an oxygen atom, a nitrogen atom and a sulfur atom" include pyrrole, furan, thiophene, imidazole, pyrazole, oxazole, isoxazole, thiazole, isothiazole, triazol, furazan, oxadiazole, thiadiazole, pyridine, pyrazine, pyrimidine, pyridazine, and the like.

In the present invention, specific examples of the "5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom" include pyrrole, oxazole, isoxazole, thiazole, isothiazole, pyridine, imidazole, pyrazole, furazan, oxadiazole, thiadiazole, pyrazine, pyrimidine, pyridazine, triazol, and the like.

In the present invention, specific examples of the "9- to 10-membered bicyclic unsaturated heterocycle including one to four heteroatoms selected from an oxygen atom, a nitrogen atom, and a sulfur atom, or which may be partially saturated" include indolizine, indoline, isoindoline, dihydrobenzofuran, dihydroisobenzofuran, dihydrobenzothiophene, dihydroisobenzothiophene, dihydroindazole, dihydrobenzoxazole, dihydrobenzothiazole, dihydrobenzimidazole, dioxaindan, benzodithiolane, quinolizine, chromene, dihydroquinoline, tetrahydroquinoline, dihydroisoquinoline, tetrahydroisoquinoline, chroman, dithianaphthalene, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzooxathiane, dihydrobenzooxazine, dihydrobenzothiazine, benzodioxan, benzodithiane, pyrazinomorpholine, indole, isoindole, benzofuran, isobenzofuran, benzothiophene, isobenzothiophene, indazole, benzoxazole, benzothiazole, benzimidazole, benzofurazan, benzothiadiazole, benzotriazol, purine, quinoline, isoquinoline, phthalazine, naphthyridine, quinoxaline, quinazoline, cinnoline, pteridine, and the like.

In the present invention, "9- to 10-membered bicyclic unsaturated heterocycle including one to three heteroatoms selected from an oxygen atom, a nitrogen atom, and a sulfur atom, in which 5- or 6-membered heterocycle is condensed to benzene, or which may be partially saturated" include indole, isoindole, benzofuran, isobenzofuran, benzothiophene, isobenzothiophene, quinoline, isoquinoline, indazole, benzoxazole, benzothiazole, benzimidazole, phthalazine, quinoxaline, quinazoline, cinnoline, benzofurazan, benzothiadiazole, benzotriazol, indoline, isoindoline, dihydrobenzofuran, dihydroisobenzofuran, dihydrobenzothiophene, dihydroisobenzothiophene, chromene, dihydroquinoline, tetrahydroquinoline, dihydroisoquinoline, tetrahydroisoquinoline, chroman, dihydroindazole, dihydrobenzoxazole, dihydrobenzothiazole, dihydrobenzimidazole, dioxaindan, benzodithiolane, dithianaphthalene, dihydrophthalazine, tetrahydrophthalazine, dihydroquinoxaline, tetrahydroquinoxaline, dihydroquinazoline, tetrahydroquinazoline, dihydrocinnoline, tetrahydrocinnoline, benzooxathiane, dihydrobenzooxazine, dihydrobenzothiazine, benzodioxan, benzodithiane, and the like.

In the present invention, when the number of substituents is not specified, the number of substituents, if present, is intended to be one or more.

In the present invention, each substituent is independently defined for each occurrence in the definition in the general formula. For example, when more than one substituents $R^{10}$ are present on the "ring A" or the "ring B" and/or the "ring C", respectively, each substituent is selected independently for each occurrence, substituents may be the same as or different from each other.

In the present invention, the KCNQ2-5 channels mean a KCNQ channel in which four of each of the subtypes KCNQ2 to KCNQ5 are gathered to form a homotetramer or a heterotetramer. Examples thereof include homotetramers such as KCNQ2, KCNQ3, KCNQ4, and KCNQ5 channel, or heterotetramers such as KCNQ2/3, KCNQ3/4, KCNQ3/5 channel, and the like. Preferable examples include KCNQ2/3, KCNQ4 and/or KCNQ5 channel.

In the present invention, the KCNQ2-5 channel activator refers to a compound having an opening action with respect to the KCNQ2-5 channels (preferably, KCNQ2/3, KCNQ4 and/or KCNQ5 channel). In the present invention, a KCNQ channel activation action has the same meaning as that of a KCNQ channel opening action.

In the present invention, $X^1$ is preferably C—$R^6$.

In the present invention, $X^2$ is preferably C—$R^7$.

In the present invention, $R^{11}$ is preferably O$R^1$. Furthermore, OH and $NH_2$ are also preferable.

In the present invention, Y is preferably —NH— or a bond, and more preferably —NH—.

In the present invention, $R^1$ is preferably a hydrogen atom or a methyl group, and more preferably a hydrogen atom.

In the present invention, $R^2$ is preferably a hydrogen atom or a C1-2 alkyl group which may be substituted with halogen, more preferably a hydrogen atom or a methyl group which may be substituted with halogen, and further more preferably a methyl group or a trifluoromethyl group.

In the present invention, $R^3$ is preferably a hydrogen atom or a C1-2 alkyl group which may be substituted with halogen, more preferably a hydrogen atom or a methyl group which may be substituted with halogen, and further more preferably a hydrogen atom, a methyl group or a trifluoromethyl group.

In the present invention, the combination of $R^2$ and $R^3$ is preferably a combination in which at least one of $R^2$ and $R^3$ is a methyl group which may be substituted with halogen, and the other is a hydrogen atom or a methyl group which may be substituted with halogen, and more preferably a combination in which at least one of $R^2$ and $R^3$ is a trifluoromethyl group, and the other is a hydrogen atom or a methyl group.

In the present invention, $R^4$ is preferably a hydrogen atom, a halogen, a C1-4 alkyl group or a C1-4 alkoxy group, more preferably a hydrogen atom, halogen, or a C1-4 alkyl group, further preferably halogen or a methyl group, and particularly preferably halogen.

In the present invention, $R^5$ is preferably a hydrogen atom, a halogen, a C1-4 alkyl group or a C1-4 alkoxy group, more preferably a hydrogen atom, halogen, or a C1-4 alkyl group, further preferably halogen or a methyl group, and particularly preferably halogen.

In the present invention, $R^6$ is preferably a hydrogen atom or a halogen, and further preferably a hydrogen atom.

In the present invention, $R^7$ is preferably a hydrogen atom or a halogen, and further preferably a hydrogen atom.

In the present invention, it is preferable that at least one of $R^6$ and $R^7$ is a hydrogen atom, and more preferable that both of $R^6$ and $R^7$ are a hydrogen atom.

In the present invention, $R^8$ is preferably a hydrogen atom or a methyl group, and more preferably a hydrogen atom.

In the present invention, $R^9$ is preferably (1) a ring A, (2) a C2-4 alkyl group which may be substituted with halogen or a hydroxy group, (3) -ring B-ring C, (4) -ring B-methylene-ring C, or (5) -ring B-O-ring C. Herein, the rings each independently may be substituted with one to five $R^{10}$. $R^9$ is more preferably a ring A substituted with one to five $R^{10}$; further preferably a 5- to 6-membered monocyclic unsaturated heterocycle including one to three heteroatoms selected from an oxygen atom, a nitrogen atom, and a sulfur atom, which may be substituted with one to three substituents (preferably one substituent) each selected from the group consisting of (1) halogen, (2) a C1-4 alkyl group which may be substituted with halogen, and (3) a C1-4 alkoxy group which may be substituted with halogen (preferably selected from the group consisting of halogen and a C1-4 alkyl group which may be substituted with halogen); and particularly preferably a 5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom, which is substituted with a single substituent of halogen or a C1-4 alkyl group which may be substituted with halogen (preferably with halogen or a trifluoromethyl group).

In the present invention, the ring A is preferably (1) C3-8 monocyclic cycloalkane, (2) 3- to 7-membered monocyclic heterocycloalkane including one oxygen atom as a heteroatom, (3) a C5-7 monocyclic unsaturated carbocyclic ring, or which may be partially saturated, (4) a C8-10 bicyclic unsaturated carbocyclic ring, or which may be partially saturated, (5) a 5- to 7-membered monocyclic unsaturated heterocycle including one to three heteroatoms selected from an oxygen atom, a nitrogen atom, and a sulfur atom, or which may be partially saturated, (6) a 9- to 10-membered bicyclic unsaturated heterocycle including one to four heteroatoms selected from an oxygen atom, a nitrogen atom, and a sulfur atom, or which may be partially saturated (herein, the rings each independently may be substituted with one to five $R^{10}$); more preferably (1) a C3-6 monocyclic cycloalkane, (2) a 5- to 6-membered monocyclic heterocycloalkane including one oxygen atom as a heteroatom (tetrahydrofuran and tetrahydropyran), (3) a C5-6 monocyclic unsaturated carbocyclic ring or which may be partially saturated, (4) a 5- to 6-membered monocyclic unsaturated heterocycle including one to three heteroatoms selected from an oxygen atom, a nitrogen atom and a sulfur atom, or which may be partially saturated, (5) 9- to 10-membered bicyclic unsaturated heterocycle including one to three heteroatoms selected from an oxygen atom, a nitrogen atom, and a sulfur atom in which 5- or 6-membered heterocycle is condensed to benzene (herein, the rings each independently may be substituted with one to five $R^{10}$); further preferably, a 5- to 6-membered monocyclic unsaturated heterocycle including one to three heteroatoms selected from an oxygen atom, a nitrogen atom, and a sulfur atom, which may be substituted with one to three substituents (preferably one substituent) each selected from the group consisting of (1) halogen, (2) a C1-4 alkyl group which may be substituted with halogen, and (3) a C1-4 alkoxy group which may be substituted with halogen (preferably selected from the group consisting of halogen and a C1-4 alkyl group which may be substituted with halogen); and particularly preferably 5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom, which is substituted with a single substituent of halogen or a C1-4 alkyl group which may be substituted with halogen (preferably with halogen or a trifluoromethyl group).

In the present invention, the ring B is preferably (1) C3-8 monocyclic cycloalkane, (2) 3- to 7-membered monocyclic heterocycloalkane including one oxygen atom as a heteroatom, (3) a C5-7 monocyclic unsaturated carbocyclic ring, or which may be partially saturated, or (4) 5- to 7-membered monocyclic unsaturated heterocycle including one to three heteroatoms selected from an oxygen atom, a nitrogen atom and a sulfur atom, or which may be partially saturated (herein the rings each independently may be substituted with one to five $R^{10}$); more preferably 5- to 6-membered monocyclic unsaturated heterocycle including one to three heteroatoms selected from an oxygen atom, a nitrogen atom, and a sulfur atom, which may be substituted with one to three substituents (preferably one substituent) selected from the group consisting of (1) halogen, (2) a C1-4 alkyl group which may be substituted with halogen, (3) a C1-4 alkoxy group which may be substituted with halogen (preferably each selected from the group consisting of halogen and a C1-4 alkyl group which may be substituted with halogen); further preferably 5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom, which may be substituted with a single substituent of halogen or a C1-4 alkyl group which may be substituted with halogen (preferably with halogen or a trifluoromethyl group); and particularly preferably 5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom, and which does not include more than the substituents described in the formula.

In the present invention, the ring C is preferably (1) C3-8 monocyclic cycloalkane, (2) 3- to 7-membered monocyclic heterocycloalkane including one oxygen atom or a nitrogen atom as a heteroatom, (3) a C5-7 monocyclic unsaturated carbocyclic ring, or which may be partially saturated, or (4) 5- to 7-membered monocyclic unsaturated heterocycle including one to three heteroatoms selected from an oxygen atom, a nitrogen atom and a sulfur atom, or which may be partially saturated (herein the rings each independently may be substituted with one to five $R^{10}$); more preferably (1) C3-8 monocyclic cycloalkane, (2) 3- to 7-membered monocyclic heterocycloalkane including one nitrogen atom as heteroatom, or (3) a C5-7 monocyclic unsaturated carbocyclic ring or which may be partially saturated (herein, the rings each independently may be substituted with one to five $R^{10}$); further preferably C3-8 monocyclic cycloalkane which may be substituted with one to five $R^{10}$, or benzene which may be substituted with one to three $R^{10}$; and particularly preferably C3-8 monocyclic cycloalkane or benzene.

In the present invention, $R^{10}$ is preferably (1) halogen, (2) a hydroxy group, (3) a cyano group, (4) a C1-4 alkyl group which may be substituted with halogen or a hydroxy group, or (5) a C1-4 alkoxy group which may be substituted with halogen or a hydroxy group; more preferably (1) halogen, (2) a C1-4 alkyl group which may be substituted with halogen, or (3) a C1-4 alkoxy group which may be substituted with halogen; further preferably (1) halogen or (2) a C1-4 alkyl group which may be substituted with halogen; and particularly preferably halogen or a trifluoromethyl group.

In the present invention, a compound of the general formula (I) including the aforementioned preferable combination is preferable.

In the present invention, a preferable compound includes a compound represented by the general formula (I-1):

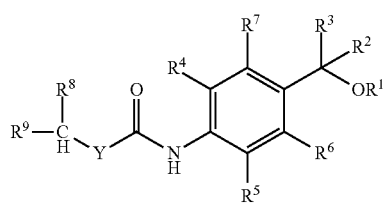

(I-1)

(wherein the symbols represent the same meanings as defined above), a salt thereof, a solvate thereof, or a cocrystal thereof.

In the present invention, a preferable compound includes a compound represented by the general formula (II):

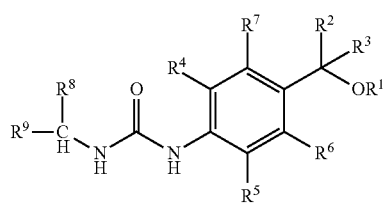

(II)

(wherein the symbols represent the same meanings as defined above), a salt thereof, a solvate thereof, or a cocrystal thereof.

Furthermore, in the present invention, a preferable compound includes a compound represented by the general formula (III):

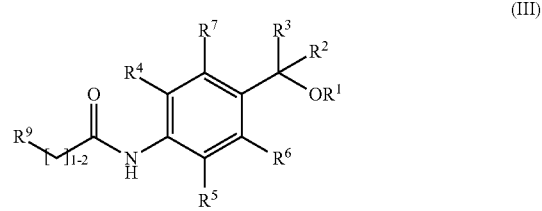

(III)

(wherein the symbols represent the same meanings as defined above), a salt thereof, a solvate thereof, or a cocrystal thereof.

The definitions of preferable groups (single or any combination thereof) mentioned above are also applied to the general formula (I-1), (II) or (III).

In the present invention, the compounds of the general formula (I-1), (II) or (III) including the combinations of the above-listed preferable groups are preferable.

In the present invention, a more preferable compound includes a compound represented by the general formula (II-1):

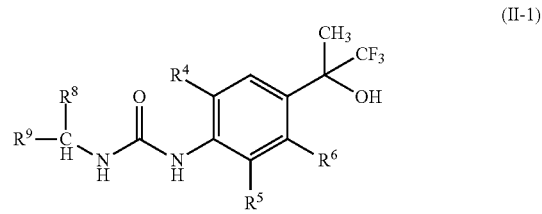

(II-1)

(wherein $R^6$ is a hydrogen atom or halogen, and the other symbols represent the same meanings as defined above), a salt thereof, a solvate thereof, or a cocrystal thereof.

Furthermore, in the present invention, a more preferable compound includes a compound represented by the general formula (II-2):

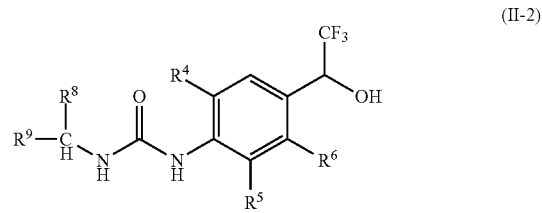

(II-2)

(wherein $R^6$ is a hydrogen atom or halogen, and the other symbols represent the same meanings as defined above), a salt thereof, a solvate thereof, or a cocrystal thereof.

The definitions of preferable groups (single or any combination thereof) mentioned above are also applied to the general formula (II-1) or (II-2).

In the present invention, the compounds of the general formula (II-1) or (II-2) including the combinations of the above-listed preferable groups are preferable.

In the present invention, a further preferable compound includes a compound represented by the general formula (II-1-1):

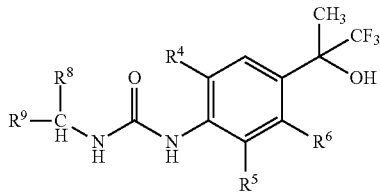

(II-1-1)

(wherein $R^4$ and $R^5$ are each independently (1) a hydrogen atom, (2) halogen, (3) a C1-4 alkyl group, or (4) a C1-4 alkoxy group (preferably, $R^4$ and $R^5$ are each independently a hydrogen atom, halogen or a C1-4 alkyl group), wherein both $R^4$ and $R^5$ are not simultaneously a hydrogen atom; $R^6$ is a hydrogen atom or halogen; $R^8$ is (1) a hydrogen atom or (2) a C1-4 alkyl group which may be substituted with halogen or a hydroxy group (preferably, a hydrogen atom or a methyl group); $R^9$ is preferably (1) a ring A, (2) a C2-4 alkyl group which may be substituted with halogen or a hydroxy group, (3) -ring B-ring C, (4) -ring B-methylene-ring C, or (5) -ring B-O-ring C ($R^9$ is preferably a ring A); the ring A is (1) C3-8 monocyclic cycloalkane, (2) 3- to 7-membered monocyclic heterocycloalkane including one oxygen atom as a heteroatom, (3) a C5-7 monocyclic unsaturated carbocyclic ring, or which may be partially saturated, (4) a C8-10 bicyclic unsaturated carbocyclic ring, or which may be partially saturated, (5) 5- to 7-membered monocyclic unsaturated heterocycle including one to three heteroatoms selected from an oxygen atom, a nitrogen atom and a sulfur atom, or which may be partially saturated, or (6) 9- to 10-membered bicyclic unsaturated heterocycle including one to four heteroatoms selected from an oxygen atom, a nitrogen atom and a sulfur atom, or which may be partially saturated; the ring B is (1) C3-8 monocyclic cycloalkane, (2) 3- to 7-membered monocyclic heterocycloalkane including one oxygen atom as a heteroatom, (3) a C5-7 monocyclic unsaturated carbocyclic ring or which may be partially saturated, or (4) 5- to 7-membered monocyclic unsaturated heterocycle including one to three heteroatoms selected from an oxygen atom, a nitrogen atom and a sulfur atom, or which may be partially saturated; the ring C is (1) C3-8 monocyclic cycloalkane, (2) a 3- to 7-membered monocyclic heterocycloalkane including one oxygen atom or one nitrogen atom as a heteroatom, (3) a C5-7 monocyclic unsaturated carbocyclic ring, or which may be partially saturated, or (4) 5- to 7-membered monocyclic unsaturated heterocycle including one to three heteroatoms selected from an oxygen atom, a nitrogen atom and a sulfur atom, or which may be partially saturated; herein the ring A, ring B or ring C each independently may be substituted with one to five $R^{10}$, and when a plurality of $R^{10}$ is present, the plurality of $R^{10}$ may be the same as or different from each other; $R^{10}$ is (1) halogen, (2) a hydroxy group, (3) a cyano group, (4) a C1-4 alkyl group which may be substituted with halogen or a hydroxy group, or (5) a C1-4 alkoxy group which may be substituted with halogen or a hydroxy group), a salt thereof, a solvate thereof, or a cocrystal thereof.

In the present invention, a further preferable compound includes a compound represented by the general formula (II-2-1):

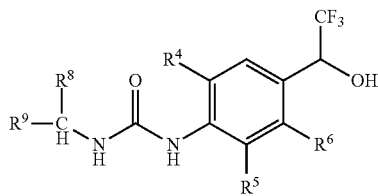

(II-2-1)

(wherein $R^4$ and $R^5$ are each independently (1) a hydrogen atom, (2) halogen, (3) a C1-4 alkyl group, or (4) a C1-4 alkoxy group (preferably, $R^4$ and $R^5$ are each independently a hydrogen atom, halogen or a C1-4 alkyl group), wherein both $R^4$ and $R^5$ are not simultaneously a hydrogen atom; $R^6$ is a hydrogen atom or halogen; $R^8$ is (1) a hydrogen atom or (2) a C1-4 alkyl group which may be substituted with halogen or a hydroxy group (preferably, a hydrogen atom or a methyl group); $R^9$ is preferably (1) a ring A, (2) a C2-4 alkyl group which may be substituted with halogen or a hydroxy group, (3) -ring B-ring C, (4) -ring B-methylene-ring C, or (5) -ring B-O-ring C ($R^9$ is preferably a ring A); the ring A is (1) C3-8 monocyclic cycloalkane, (2) 3- to 7-membered monocyclic heterocycloalkane including one oxygen atom as a heteroatom, (3) a C5-7 monocyclic unsaturated carbocyclic ring, or which may be partially saturated, (4) a C8-10 bicyclic unsaturated carbocyclic ring, or which may be partially saturated, (5) 5- to 7-membered monocyclic unsaturated heterocycle including one to three heteroatoms selected from an oxygen atom, a nitrogen atom and a sulfur atom, or which may be partially saturated, or (6) 9- to 10-membered bicyclic unsaturated heterocycle including one to four heteroatoms selected from an oxygen atom, a nitrogen atom and a sulfur atom, or which may be partially saturated; the ring B is (1) C3-8 monocyclic cycloalkane, (2) 3- to 7-membered monocyclic heterocycloalkane including one oxygen atom as a heteroatom, (3) a C5-7 monocyclic unsaturated carbocyclic ring or which may be partially saturated, or (4) 5- to 7-membered monocyclic unsaturated heterocycle including one to three heteroatoms selected from an oxygen atom, a nitrogen atom and a sulfur atom, or which may be partially saturated; the ring C is (1) C3-8 monocyclic cycloalkane, (2) a 3- to 7-membered monocyclic heterocycloalkane including one oxygen atom or one nitrogen atom as a heteroatom, (3) a C5-7 monocyclic unsaturated carbocyclic ring, or which may be partially saturated, or (4) 5- to 7-membered monocyclic unsaturated heterocycle including one to three heteroatoms selected from an oxygen atom, a nitrogen atom and a sulfur atom, or which may be partially saturated; herein the ring A, ring B or ring C each independently may be substituted with one to five $R^{10}$, and when a plurality of $R^{10}$ is present, the plurality of $R^{10}$ may be the same as or different from each other; $R^{10}$ is (1) halogen, (2) a hydroxy group, (3) a cyano group, (4) a C1-4 alkyl group which may be substituted with halogen or a hydroxy group, or (5) a C1-4 alkoxy group which may be substituted with halogen or a hydroxy group), a salt thereof, a solvate thereof, or a cocrystal thereof.

In the present invention, a particularly preferable compound is a compound represented by the general formula (II-1-2):

(II-1-2)

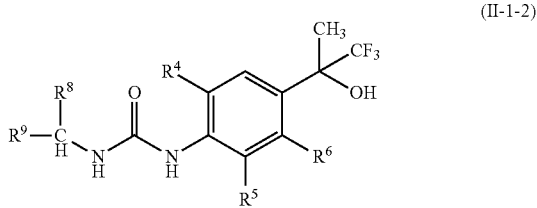

(wherein $R^4$ and $R^5$ are each independently halogen or a methyl group (preferably, $R^4$ and $R^5$ are each independently halogen); $R^6$ is a hydrogen atom or halogen (preferably, a hydrogen atom); $R^8$ is a hydrogen atom or a methyl group (preferably, a hydrogen atom); $R^9$ is a 5- to 6-membered monocyclic unsaturated heterocycle including one to three heteroatoms selected from an oxygen atom, a nitrogen atom, and a sulfur atom, which may be substituted with one to three substituents (preferably one substituent) each selected from the group consisting of (1) halogen, (2) a C1-4 alkyl group which may be substituted with halogen, and (3) a C1-4 alkoxy group which may be substituted with halogen (preferably selected from the group consisting of halogen and a C1-4 alkyl group which may be substituted with halogen) ($R^9$ is preferably a 5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom, which is substituted with a single substituent of halogen or a C1-4 alkyl group which may be substituted with halogen (preferably with halogen or a trifluoromethyl group)), a salt thereof, a solvate thereof, or a cocrystal thereof.

In the present invention, a particularly preferable compound is a compound represented by the general formula (II-2-2):

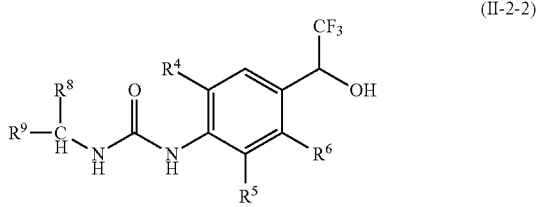

(wherein $R^4$ and $R^5$ are each independently halogen or a methyl group (preferably, $R^4$ and $R^5$ are each independently halogen); $R^6$ is a hydrogen atom or halogen (preferably, a hydrogen atom); $R^8$ is a hydrogen atom or a methyl group (preferably, a hydrogen atom); $R^9$ is a 5- to 6-membered monocyclic unsaturated heterocycle including one to three heteroatoms selected from an oxygen atom, a nitrogen atom, and a sulfur atom, which may be substituted with one to three substituents (preferably one substituent) each selected from the group consisting of (1) halogen, (2) a C1-4 alkyl group which may be substituted with halogen, and (3) a C1-4 alkoxy group which may be substituted with halogen (preferably selected from the group consisting of halogen and a C1-4 alkyl group which may be substituted with halogen) ($R^9$ is preferably a 5- to 6-membered monocyclic unsaturated nitrogen-containing heterocycle including one to three heteroatoms selected from an oxygen atom, a nitrogen atom, and a sulfur atom, wherein the said 5- to 6-membered monocyclic unsaturated nitrogen-containing heterocycle contains at least one nitrogen atom, which is substituted with a single substituent of halogen or a C1-4 alkyl group which may be substituted with halogen (preferably with halogen or a trifluoromethyl group)), a salt thereof, a solvate thereof, or a cocrystal thereof.

In the present invention, a preferable compound is:
(1) 1-{2,6-dichloro-4-[(2R)-1,1,1-trifluoro-2-hydroxy-2-propanyl]phenyl}-3-{[5-(trifluoromethyl)-2-pyridinyl]methyl}urea,
(2) 1-{2,6-dichloro-4-[(2R)-1,1,1-trifluoro-2-hydroxy-2-propanyl]phenyl}-3-{[5-(trifluoromethyl)-2-pyrimidinyl]methyl}urea,
(3) 1-{2,6-dichloro-4-[(2R)-1,1,1-trifluoro-2-hydroxy-2-propanyl]phenyl}-3-{[6-(trifluoromethyl)-3-pyridinyl]methyl}urea,
(4) 1-[(5-chloro-2-pyridinyl)methyl]-3-{2,6-dichloro-4-[(2R)-1,1,1-trifluoro-2-hydroxy-2-propanyl]phenyl}urea,
(5) 1-{2,6-dichloro-4-[(2R)-1,1,1-trifluoro-2-hydroxy-2-propanyl]phenyl}-3-{[3-(trifluoromethyl)-1,2,4-oxadiazole-5-yl]methyl}urea,
(6) 1-{2,6-dichloro-4-[(2S)-1,1,1-trifluoro-2-hydroxy-2-propanyl]phenyl}-3-{[5-(trifluoromethyl)-2-pyrimidinyl]methyl}urea,
(7) 1-{2,6-dichloro-4-[(2S)-1,1,1-trifluoro-2-hydroxy-2-propanyl]phenyl}-3-{[6-(trifluoromethyl)-3-pyridinyl]methyl}urea,
(8) 1-[(5-chloro-2-pyridinyl)methyl]-3-{2,6-dichloro-4-[(2S)-1,1,1-trifluoro-2-hydroxy-2-propanyl]phenyl}urea,
(9) 1-{2,6-dichloro-4-[(2S)-1,1,1-trifluoro-2-hydroxy-2-propanyl]phenyl}-3-{[3-(trifluoromethyl)-1,2,4-oxadiazole-5-yl]methyl}urea,
(10) 1-{2,6-dichloro-4-[(1R)-2,2,2-trifluoro-1-hydroxyethyl]phenyl}-3-{[3-(trifluoromethyl)-1,2,4-oxadiazole-5-yl]methyl}urea,
(11) 1-{2,6-dichloro-4-[(1R)-2,2,2-trifluoro-1-hydroxyethyl]phenyl}-3-{[2-(trifluoromethyl)-5-pyrimidinyl]methyl}urea,
(12) 1-{2,6-dichloro-4-[(1R)-2,2,2-trifluoro-1-hydroxyethyl]phenyl}-3-{[5-(trifluoromethyl)-2-pyrimidinyl]methyl}urea,
(13) 1-{2,6-dichloro-4-[(1R)-2,2,2-trifluoro-1-hydroxyethyl]phenyl}-3-{[2-(trifluoromethyl)-1,3-thiazole-5-yl]methyl}urea,
(14) 1-{2,6-dichloro-4-[(1S)-2,2,2-trifluoro-1-hydroxyethyl]phenyl}-3-{[3-(trifluoromethyl)-1,2,4-oxadiazole-5-yl]methyl}urea,
(15) 1-{2,6-dichloro-4-[(1S)-2,2,2-trifluoro-1-hydroxyethyl]phenyl}-3-{[2-(trifluoromethyl)-5-pyrimidinyl]methyl}urea,
(16) 1-{2,6-dichloro-4-[(1S)-2,2,2-trifluoro-1-hydroxyethyl]phenyl}-3-{[2-(trifluoromethyl)-1,3-thiazole-5-yl]methyl}urea,
(17) 1-{2,6-dichloro-4-[(2S)-1,1,1-trifluoro-2-hydroxy-2-propanyl]phenyl}-3-{[5-(trifluoromethyl)-2-pyridinyl]methyl}urea,
(18) 1-{2,6-dichloro-4-[(1S)-2,2,2-trifluoro-1-hydroxyethyl]phenyl}-3-{[5-(trifluoromethyl)-2-pyrimidinyl]methyl}urea, or a stereoisomer thereof, or a salt thereof, a solvate thereof, or a cocrystal thereof.

The compound of the present invention is preferably a compound in which the opening action with respect to the KCNQ2/3 is 100 μM or less, more preferably 10 μM or less, further preferably 1 μM or less, and particularly preferably 0.1 μM or less in terms of $EC_{50}$ value (or ECrtg50 (see (1) Biological Example 1 described later)). The compound of the present invention is further preferably a compound having the opening action with respect to all the KCNQ2/3, KCNQ4, and KCNQ5 channels (in any channels, the $EC_{50}$ value (or ECrtg 50) is preferably 100 μM or less, more preferably 10 μM or less, and further preferably 1 μM or less). A method for determining the $EC_{50}$ value (or ECrtg 50) is well known to a person skilled in the art (see, for example, Neuropharmacology, Vol. 40, 2001, pp. 888-898, European Journal of Pharmacology, Vol. 437, 2002, pp. 129-137). The $EC_{50}$ value is determined preferably by a fluorescence measurement method, and more preferably by the method described in the section of (1) Biological Example 1 described later.

The compound of the present invention is preferably a compound having excellent solubility. In the present invention, the solubility can be evaluated as solubility to a second solution (pH=6.8) of the Pharmacopoeia of Japan elution test by, for example, a dimethyl sulfoxide (DMSO) precipitation method (see, the section of (3) Solubility test described later). A compound having the solubility of 20 μM or more is preferable, more preferably 40 μM or more, further preferably 60 μM or more, and particularly preferably 80 μM or more is preferable.

The compound of the present invention is preferably a compound having excellent metabolic stability. The metabolic stability can be verified by a general measurement method using, for example, a liver microsome of human or other animal species (preferably, human). The stability of the compound in a human liver microsome can be evaluated by, for example, reacting a commercially available human liver microsome and the compound of the present invention with each other for a predetermined time (for example, 5 to 30 minutes), and calculating the residual rate in comparison between the reacted sample and unreacted sample (see, (4) Evaluation of Stability in Human Liver Microsome, described later).

The compound of the present invention is preferably a compound that is excellent in safety. For example, the compound of the present invention includes a compound which does not acts on hERG (human ether-a-go-go related gene) channel, or a compound which has a weak hERG channel inhibition action. The hERG channel inhibition action (hERG test) can be evaluated by well-known methods, for example, a rubidium method for measuring flow of rubidium ion (Rb+) in hERG expression cell, and a patch clamp test for measuring HERG current by a patch clamp technique (see, (5) Evaluation of Activity with respect to hERG IKr Current, described later).

In the present invention, unless specifically noted, all of the stereoisomers are included. For example, all of geometrical isomers of double bonds, rings, and fused rings (E-, Z-, cis-, trans-isomers), optical isomers by the presence of an asymmetric carbon atom (R-, S-isomer, α-, β-configurations, enantiomers, diastereomers), optical active isomers having optical rotation property (D, L, d, 1-isomers), polar isomers according to chromatographic separation (high-polarity isomer and low-polarity isomer), equilibrium compound, rotamers, mixtures thereof at any rate, and racemic mixtures are included in the present invention. Furthermore, the present invention also encompasses all isomers by tautomers.

In the present invention, unless specifically noted, as is apparent to a person skilled in the art, a symbol:  represents a binding to the far side of the paper (that is to say, the α-configuration),  represents a binding to the front of the paper (that is to say, the β-configuration), and  represents α-configuration, β-configuration or an arbitrary mixture thereof.

Furthermore, the optically active compound of the present invention is not limited to a compound having purity of 100%, but may include other enantiomer or diastereomer having purity of less than 50%. Specific examples of the racemic mixture include Example 5:1-[2,6-dichloro-4-(1,1,1-trifluoro-2-hydroxy-2-propanyl)phenyl]-3-{[5-(trifluoromethyl)-2-pyridinyl]methyl}urea that is a mixture of Example 22(1):1-{2,6-dichloro-4-[(2R)-1,1,1-trifluoro-2-hydroxy-2-propanyl]phenyl}-3-{[5-(trifluoromethyl)-2-pyridinyl]methyl}urea and Example 25(4):1-{2,6-dichloro-4-[(2S)-1,1,1-trifluoro-2-hydroxy-2-propanyl]phenyl}-3-{[5-(trifluoromethyl)-2-pyridinyl]methyl}urea, and the like.

In the present invention, all the mentions about the compound of the present invention include a compound represented by the general formula (I), a salt thereof, a solvate thereof, or a cocrystal thereof, and a solvate of the salt of the compound represented by the general formula (I), or a cocrystal thereof.

The compound represented by the general formula (I) is converted into a corresponding salt by a well-known method. As the salt, pharmaceutically acceptable salts are preferable. Furthermore, water-soluble salt is preferable. Appropriate salts include acid addition salts (inorganic acid salts (hydrochloride, hydrobromide, hydroiodide, sulfate, phosphate, nitrate, and the like), organic acid salts (formate, acetate, propionate, trifluoro acetate, lactate, tartrate, oxalate, malonate, succinate, fumarate, malate, maleate, benzoate, citrate, methanesulfonate, ethanesulfonate, benzenesulfonate, toluenesulfonate, isethionate, glucuronate, gluconate, aspartate, glutamate, and the like).

The compound represented by the general formula (I) and a salt thereof may be present in a not-solvation form, or in a solvation form with pharmaceutically acceptable solvent such as water and ethanol. Preferable solvates is hydrate. The compound represented by the general formula (I) and a salt thereof can be converted into a solvate by a well-known method.

The compound represented by the general formula (I) can form a cocrystal with an appropriate cocrystal former. As the cocrystal, pharmaceutically acceptable cocrystal that is formed with a pharmaceutically acceptable cocrystal former is preferable. The cocrystal is typically defined as a crystal that is formed of two or more different molecules by intermolecular interaction that is different from ionic bond. Furthermore, the cocrystal may be a composite of a neutral molecule and a salt. The cocrystal can be prepared by a well-known method, for example, melting crystallization, recrystallization from a solvent, or physically pulverizing the components together. Appropriate cocrystal formers include ones described in WO2006/007448.

The compound of the present invention can be administered as a prodrug. For example, a prodrug of the compound represented by the general formula (I) denotes a compound which is converted to the compound represented by the general formula (I) by a reaction with an enzyme, gastric acid, and the like, in a living body. Prodrugs of the compound represented by the general formula (I) include: compounds in which the hydroxyl group is acylated, alkylated, phosphorylated, or borated, when the compounds represented by the general formula (I) have a hydroxyl group (for example, the compounds represented by the general formula (I) in which the hydroxyl group is acetylated, palmitoylated, propanoylated, pivaloylated, succinylated, fumarylated, alanylated, or dimethylaminomethylcarbonylated). These compounds can be produced by well-known methods. Furthermore, the prodrug of the compound represented by the general formula (I) may be hydrate or non-hydrate. Furthermore, the prodrug of the compound represented by the general formula (I) may be a compound which is changed into the compound represented by the general formula (I) under the physiological condition, as described in "Development of Medicaments", vol. 7 "Molecular Design", pp. 163-198, published by Hirokawa Shoten in 1990.

The compound represented by the general formula (I) includes all isotopes. That is, includes the compounds, wherein at least one atom is replaced by an atom which having atomic number same as the original atom but atomic mass or mass number different from the atomic mass or mass number dominant in the natural world. Examples of the isotopes included in the compound represented by the general formula (I) include $^2H$, $^3H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like.

[Method for Producing Compound of the Present Invention]

The compound represented by the general formula (I) can be produced by the well-known methods, for example, the methods described below, the methods conforming to these methods, methods described in Examples, or the method described in "Comprehensive Organic Transformations: A Guide to Functional Group Preparations, 2nd Edition (Richard C. Larock, John Wiley & Sons Inc, 1999)", or the like, with appropriate modification and in combination thereof. Note here that in the following each production methods, each raw material compound may be used as a salt. Such a salt include salts described as above-mentioned pharmaceutically acceptable salts of the general formula (I).

A compound represented by the general formula (I-1) in which $R^{11}$ is $OR^1$ among the compound represented by the general formula (I) can be produced by the method shown in the following reaction scheme 1 or 2 using a compound represented by the general formula (SM1):

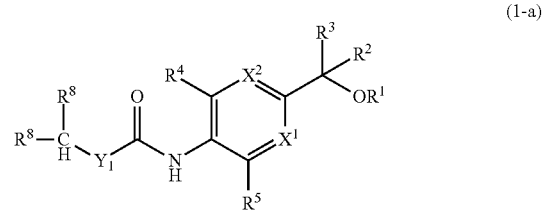

(SM1)

(wherein T represents $R^1$ or a protective group for a hydroxyl group, and the other symbols represent the same meanings as mentioned above) as a starting material.

Examples of the protective group for a hydroxyl group in T include a methyl group, an ethyl group, a propyl group, a butyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a tert-butyldimethylsilyl (TBDMS) group, a tert-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, and the like. The protective groups are not particularly limited to the above-described groups, and may include, in addition to the above-mentioned groups, groups that can be detached easily and selectively. For example, those described in "Protective Groups in Organic Synthesis (T. W. Greene, John Wiley & Sons Inc, 1999)" may be used.

A compound in which Y is —NH— or —O— among the compound represented by the general formula (I), that is, a compound represented by the general formula (1-a):

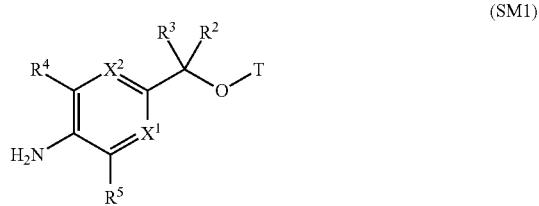

(1-a)

(wherein $Y_1$ represents —NH— or —O—, and the other symbols represent the same meanings as mentioned above) can be produced by a method shown in the reaction scheme 1:

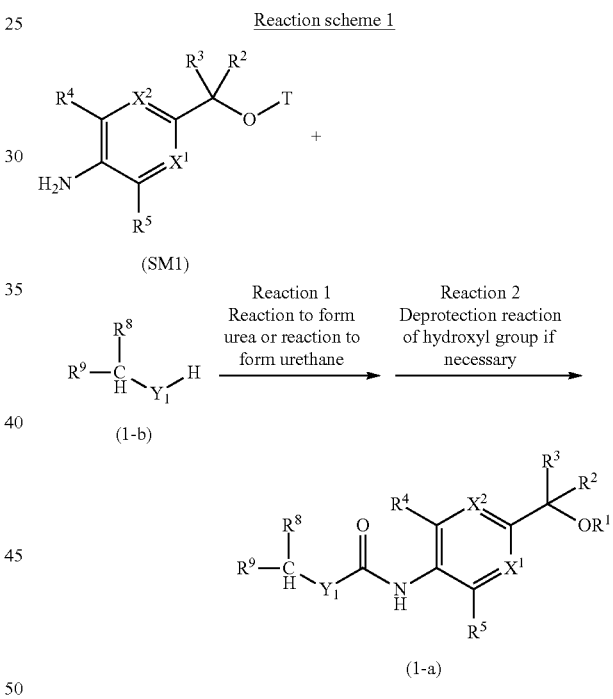

(wherein all of the symbols represent the same meanings as mentioned above).

The reaction to form urea or urethane shown in the reaction 1 in the reaction scheme 1 is carried out by, for example, reacting a compound represented by the general formula (SM1) with triphosgene at temperatures from room temperature to 40° C. in an organic solvent (tetrahydrofuran, N-methyl-2-pyrrolidinone, N,N-dimethylformamide, dichloromethane, and the like) in the presence of a base (triethylamine, diisopropyl ethyl amine, and the like) so as to form a corresponding isocyanate, and then reacting with the compound represented by the general formula (1-b) in an organic solvent (tetrahydrofuran, N-methyl-2-pyrrolidinone, dichloromethane, and the like) at temperatures from room temperature to 60° C. in the presence or absence of a base (triethylamine, diisopropyl ethyl amine, and the like). Alternatively, the reaction for generating isocyanate from the compound represented by the general formula (SM1) and the reaction for reacting the compound represented by the general formula (1-b) may be carried out in the opposite order. Furthermore, the reaction is carried out, for example, in the organic solvent (dichloromethane, N,N-dimethylformamide), in the presence of 1,1'-carbonylbis-1H-imidazole (CDI), in the presence or absence of base (triethylamine, N-methyl morpholine, and the like) at about 0 to 80° C. It is desirable that any of these reactions be carried out under the atmosphere of inert gas (argon, nitrogen, and the like) in the anhydrous condition.

Herein, in the reaction scheme 1, deprotection of a hydroxyl group shown in the reaction 2 is carried out if necessary. In the compound represented by the general formula (1-a), when T is $R^1$, the compound represented by the general formula (1-a) can be produced without carrying out the deprotection reaction.

The deprotection reaction of the protective group for the hydroxyl group is well known, and can be carried out by the methods mentioned below. Examples thereof include:

(1) a deprotection reaction by alkaline hydrolysis,
(2) a deprotection reaction in acidic conditions,
(3) a deprotection reaction by hydrogenolysis,
(4) a deprotection reaction of a silyl group,
(5) a deprotection reaction using metal,
(6) a deprotection reaction using a metal complex, and the like.

These methods will be specifically described:

(1) The deprotection reaction by alkaline hydrolysis condition is carried out, for example, in an organic solvent (methanol, tetrahydrofuran, dioxane, and the like) using hydroxide of alkaline metal (sodium hydroxide, potassium hydroxide, lithium hydroxide, and the like), hydroxide of alkaline earth metal (barium hydroxide, calcium hydroxide, and the like), or carbonate (sodium carbonate or potassium carbonate, and the like), or an aqueous solution thereof or a mixture thereof at temperatures of about 0 to 40° C.

(2) The deprotection reaction in acidic conditions is carried out, for example, in an organic solvent (dichloromethane, chloroform, dioxane, ethyl acetate, anisole, and the like), in organic acid (acetic acid, trifluoroacetic acid, methanesulfonic acid, p-toluenesulfonic acid, and the like), or inorganic acid (hydrochloric acid, sulfuric acid, and the like) or a mixture thereof (hydrogen bromide/acetic acid, and the like) at temperatures of about 0 to 100° C.

(3) The deprotection reaction by hydrogenolysis is carried out, for example, in a solvent (ethers (tetrahydrofuran, dioxane, dimethoxyethane, diethyl ether, and the like), alcohols (methanol, ethanol, and the like), benzenes (benzene, toluene, and the like), ketones (acetone, methyl ethyl ketone, and the like), nitriles (acetonitrile, and the like), amides (dimethylformamide, and the like), water, ethyl acetate, acetic acid, or a mixture of two or more thereof, etc.) in the presence of a catalyst (palladium-carbon, palladium black, palladium hydroxide, platinum oxide, Raney nickel, and the like) under hydrogen atmosphere at normal pressure or elevated pressure, or in the presence of ammonium formate at temperatures of about 0 to 200° C.

(4) The deprotection reaction of a silyl group is carried out, for example, in a water-miscible organic solvent (tetrahydrofuran, acetonitrile, and the like), by using tetrabutylammonium fluoride at temperatures of about 0 to 40° C.

(5) The deprotection reaction using metal is carried out, for example, in an acidic solvent (acetic acid, a buffer solution of pH 4.2 to 7.2 or a mixture thereof and an organic solvent such as tetrahydrofuran, and the like), in the presence of a zinc powder, if necessary under sonication, at temperatures of about 0 to 40° C.

(6) The deprotection reaction using a metal complex is carried out, for example, in an organic solvent (dichloromethane, dimethylformamide, tetrahydrofuran, ethyl acetate, acetonitrile, dioxane, ethanol, and the like), water or a mixture thereof, in the presence of a trap reagent (tributyltin hydride, triethylsilane, dimedone, morpholine, diethylamine, pyrrolidine, and the like), an organic acid (acetic acid, formic acid, 2-ethylhexanic acid, and the like) and/or an organic acid salt (sodium 2-ethylhexanate, potassium 2-ethylhexanate, and the like), in the presence or absence of a phosphine reagent (triphenylphosphine, and the like), using a metal complex (tetrakis(triphenylphosphine)palladium(O), dichlorobis(triphenylphosphine)palladium (II), palladium acetate (II), chlorotris(triphenylphosphine)rhodium (I), and the like) at temperatures of about 0 to 40° C.

In addition to the above-mentioned methods, the deprotection reaction can be carried out by, for example, the method described in "Protective Groups in Organic Synthesis (T. W. Greene, John Wiley&Sons Inc, 1999)".

As those skilled in the art can easily understand, the objective compound of the present invention can be easily produced by appropriately using these deprotection reactions.

A compound in which Y is a bond among the compounds represented by the general formula (I), that is, a compound represented by the general formula (2-a):

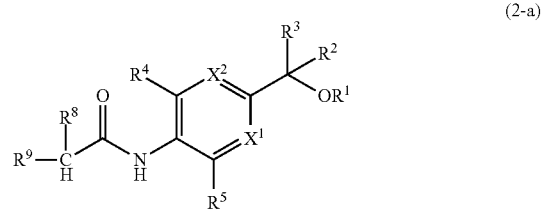

(wherein all of the symbols represent the same meanings as mentioned above) can be produced by a method shown in the reaction scheme 2:

Reaction scheme 2

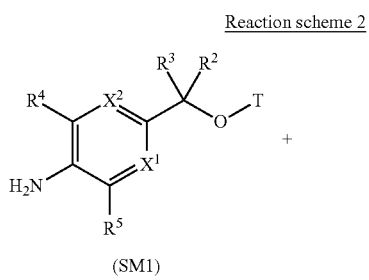

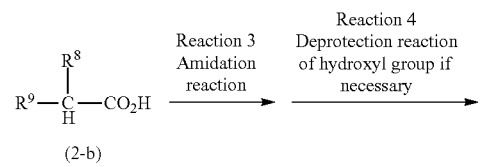

-continued

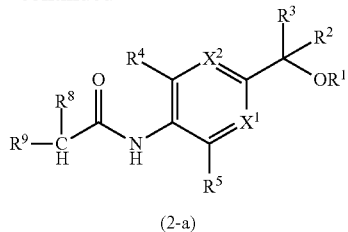

(2-a)

(wherein all of the symbols represent the same meanings as mentioned above).

That is to say, the objective compound can be produced by subjecting the compound represented by the general formula (SM1) and the compound represented by the general formula (2-b) to the reaction 3: amidation reaction, and to the reaction 4: deprotection reaction of a hydroxyl group if necessary.

The amidation reaction is well known, and examples thereof include:
(1) a method using an acid halide,
(2) a method using a mixed acid anhydride, and
(3) a method using a condensing agent.
These methods are specifically described below:

(1) The method using an acid halide is carried out, for example, by reacting a carboxylic acid with an acid halogenating agent (oxalyl chloride, thionyl chloride, and the like) in an organic solvent (chloroform, dichloromethane, diethyl ether, tetrahydrofuran, and the like) or in the absence of any solvent at −20° C. to reflux temperature, and then reacting the obtained acid halide with an amine in the presence of a base (pyridine, triethylamine, dimethylaniline, dimethylaminopyridine, diisopropylethylamine, and the like) in an organic solvent (chloroform, dichloromethane, diethyl ether, tetrahydrofuran, and the like) at 0 to 40° C. Furthermore, the method can be also carried out by reacting the obtained acid halide with an amine, at 0 to 40° C. by using an alkaline aqueous solution (sodium bicarbonate water or a sodium hydroxide solution, and the like) in an organic solvent (dioxane, tetrahydrofuran, and the like).

(2) The method using a mixed acid anhydride is carried out, for example, by reacting carboxylic acid with an acid halide (pivaloyl chloride, tosyl chloride, mesyl chloride, and the like) or an acid derivative (ethyl chloroformate, isobutyl chloroformate, and the like) in an organic solvent (chloroform, dichloromethane, diethyl ether, tetrahydrofuran, and the like) or in the absence of any solvent in the presence of a base (pyridine, triethylamine, dimethylaniline, dimethylaminopyridine, diisopropylethylamine, and the like) at 0 to 40° C., and then reacting the obtained mixed acid anhydride with an amine in an organic solvent (chloroform, dichloromethane, diethyl ether, tetrahydrofuran, and the like) at 0 to 40° C.

(3) The method using a condensing agent is carried out, for example, by reacting a carboxylic acid with an amine in an organic solvent (chloroform, dichloromethane, dimethyl formamide, diethyl ether, tetrahydrofuran, and the like) or in the absence of any solvent in the presence or absence of a base (pyridine, triethylamine, dimethylaniline, dimethylaminopyridine, and the like), using a condensing agent (1,3-dicyclohexylcarbodiimide (DCC), 1-ethyl-3-[3-(dimethylamino)propyl]carbodiimide (EDC), 1,1'-carbonylbis-1H-imidazole (CDI), 2-chloro-1-methylpyridinium iodine, 1-propylphosphonic acid cyclic anhydride (1-propanephosphonic acid cyclic anhydride, PPA), and the like), and in the presence or absence of 1-hydroxybenztriazole (HOBt) at 0 to 40° C.

These reactions (1), (2), and (3) are desirably carried out under the atmosphere of an inert gas (argon, nitrogen, and the like) in anhydrous conditions.

Herein, deprotection of a hydroxyl group is carried out if necessary. In the compound represented by the general formula (2-a), when T is $R^1$, the compound represented by the general formula (2-a) can be produced without carrying out the deprotection reaction.

The deprotection reaction of a hydroxyl group can be carried out in the same manner as in the deprotection reaction of a hydroxyl group described in the reaction scheme 1.

The compound represented by the general formula (SM1) can be produced using the compound represented by the general formula (3-a):

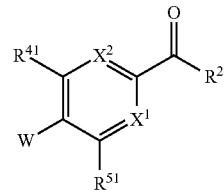

(3-a)

(wherein W represents halogen (Cl, Br, I) or a Tf (trifluoromethanesulphonyl) O group, or a Ts (toluenesulphonyl) O group, $R^{41}$ and $R^{51}$ each represent the same meaning as those of $R^4$ and $R^5$ (wherein, both $R^{41}$ and $R^{51}$ may be simultaneously a hydrogen atom), and the other symbols represent the same meanings as mentioned above); and the compound represented by the general formula (3-b):

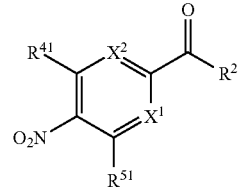

(3-b)

(wherein all of the symbols represent the same meanings as mentioned above), or the compound represented by the general formula (3-g):

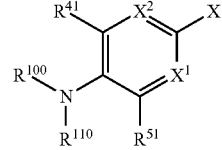

(3-g)

(wherein X represents halogen (Cl, Br, I), $R^{100}$ and $R^{110}$ each independently represent a hydrogen atom or a protective group of an amino group, the other symbols represent the same meanings as mentioned above), as starting materials, by a method shown in the reaction scheme 3:

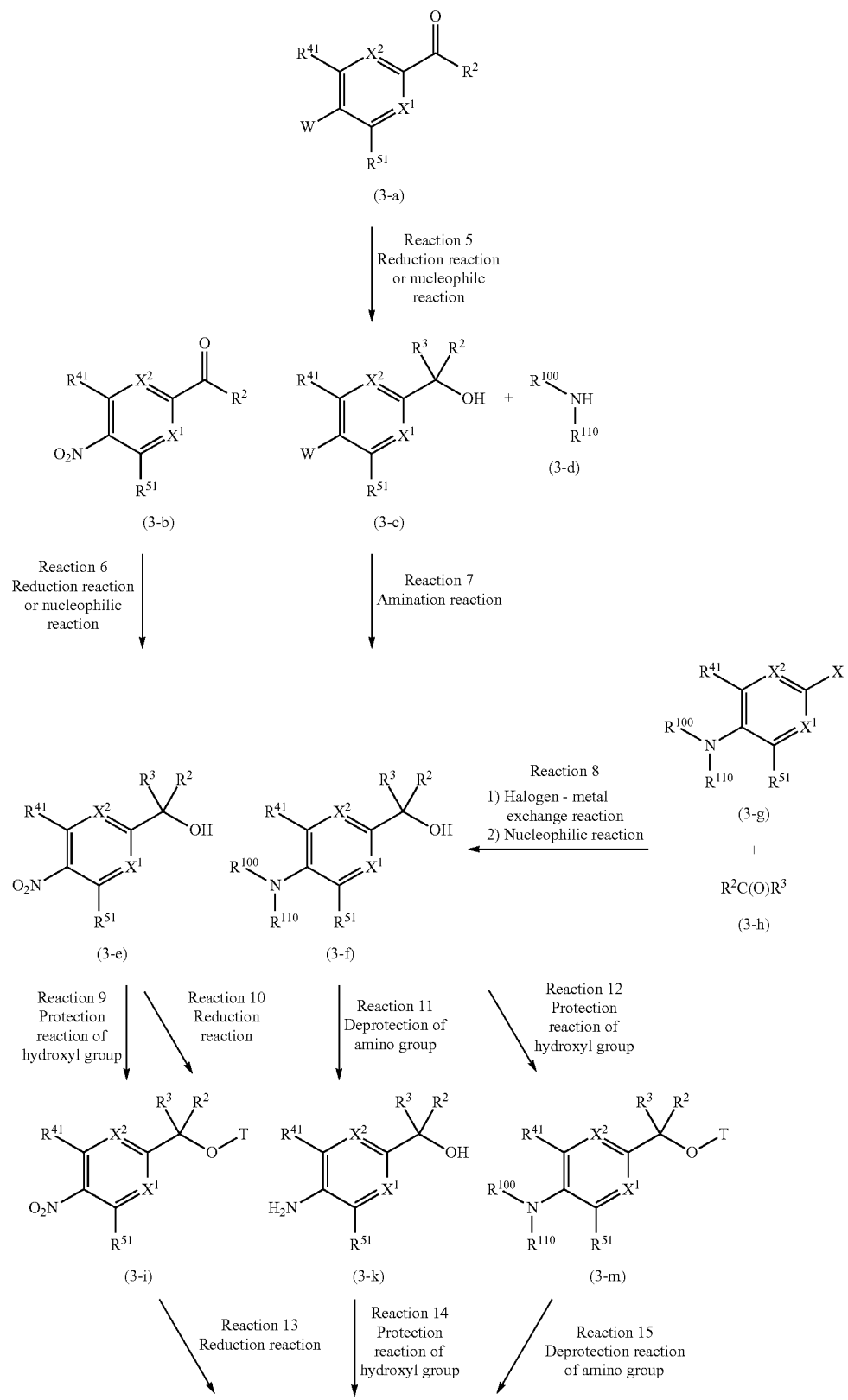

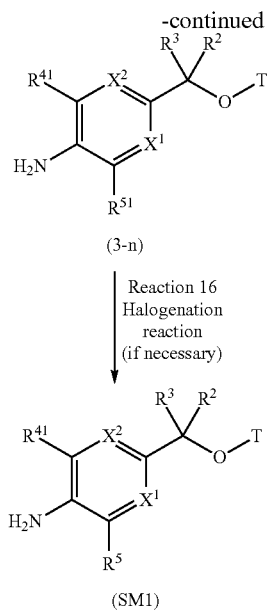

(3-n)

Reaction 16
Halogenation reaction
(if necessary)

(SM1)

(wherein all of the symbols represent the same meanings as mentioned above).

The compounds represented by the general formula (3-a) in which W is a TfO group or a TsO group, can be produced from a compound in which W is a hydroxyl group by a well-known method, for example, the method described in "Comprehensive Organic Transformations: A Guide to Functional Group Preparations, second edition (Richard C. Larock, John Wiley & Sons Inc, 1999)" and the like. Furthermore, they can be produced by the method described in Example 37.

Examples of the protective group for an amino group in $R^{100}$ and $R^{110}$ include a benzyloxycarbonyl group, a tert-butoxycarbonyl (Boc) group, an allyloxycarbonyl (Alloc) group, a 1-methyl-1-(4-biphenyl)ethoxycarbonyl (Bpoc) group, a trifluoroacetyl group, a 9-fluororenylmethoxycarbonyl group (Fmoc), a benzyl (Bn) group, a p-methoxybenzyl group, a benzyloxymethyl (BOM) group, a 2-(trimethylsilyl)ethoxymethyl (SEM) group, and the like.

The protective groups are not particularly limited to the above-described groups, and may include, in addition to the above-mentioned groups, groups that can be detached easily and selectively. For example, those described in "Protective Groups in Organic Synthesis (T. W. Greene, John Wiley & Sons Inc, 1999)" may be used.

In the reaction scheme 3, the nucleophilic reaction shown in the reactions 5 and 6 is carried out by reacting the compound represented by the general formula (3-a) or the general formula (3-b) with an organic metal reagent corresponding to $R^3$, for example, alkyl($R^3$) magnesium bromide, alkyl($R^3$) lithium in an organic solvent (tetrahydrofuran, diethyl ether, and the like) in the presence or absence of cerium chloride at temperatures from −78° C. to room temperature. Furthermore, the reaction is carried out also by reacting Rupert reagent (trifluoromethyl trimethyl silane) in the organic solvent (tetrahydrofuran, diethyl ether, and the like) in the presence of tetrabutyl ammonium fluoride at temperatures from −78° C. to room temperature.

In the reaction scheme 3, the reduction reaction shown in the reactions 5 and 6 is carried out by reacting the compound represented by the general formula (3-a) (wherein $R^2$ is other than hydrogen) with a reducing agent (sodium borohydride, lithium borohydride, lithium aluminum hydride, diisobutylaluminum hydride, and the like) in an organic solvent (methanol, ethanol, tetrahydrofuran, hexane, and the like) at temperatures from −78° C. to 80° C.

In the reaction scheme 3, the amination reaction shown in the reaction 7 is carried out by reacting the compound represented by the general formula (3-c) and the compound represented by the general formula (3-d) at temperatures from room temperature to −120° C., in an organic solvent (ethyl acetate, isopropyl acetate, benzene, toluene, xylene, heptane, cyclohexane, tetrahydrofuran, dioxane, dimethoxyethane, ethanol, isopropanol, polyethylene glycol, dimethyl sulfoxide, N,N-dimethylformamide, N,N-dimethyl acetamide, N-methyl-2-pyrrolidinone, methylene chloride, chloroform, acetone, acetonitrile, water, or the mixture thereof, or the like), in the presence of base (diethylamine, triethylamine, propyl amine, diisopropyl amine, diisopropyl ethyl amine, dibutyl amine, tributyl amine, pyrrolidine, piperidine, N-methyl piperidine, 1,4-diazabicyclo[2.2.2]octane (DABCO), pyridine, sodium hydroxide, sodium hydrogencarbonate, sodium carbonate, potassium carbonate, cesium carbonate, sodium phosphate, potassium phosphate, potassium fluoride, or the like), and a catalyst (palladium catalyst (for example, tetrakis(triphenylphosphine) palladium (Pd (PPh$_3$)$_4$), bis(triphenylphosphine)palladium dichloride (PdCl$_2$(PPh$_3$)$_2$), palladium acetate (Pd(OAc)$_2$), palladium dichloride (PdCl$_2$), palladium black, 1,1'-bis(diphenylphosphino ferrocene)dichloropalladium (PdCl$_2$(dppf)$_2$), diallyl dichloride palladium (PdCl$_2$(allyl)$_2$), phenylbis(triphenylphosphine)palladium iodide (PhPdI(PPh$_3$)$_2$), tris(dibenzylideneacetone)dipalladium (Pd$_2$(DBA)$_3$), bis(tri-tert-butyl phosphine)palladium (Pd(tBu$_3$P)$_2$), and the like), and in the presence of ligand (for example, 4,5-bis(diphenylphosphino)-9,9-dimethyl xanthene, and the like).

In the reaction scheme 3, the halogen-metal exchange reaction of aryl halide, and subsequent nucleophilic reaction shown in reaction 8 are carried out by reacting the compound represented by the general formula (3-g) with an organic metal reagent (n-butyllithium, tert-butyllithium, isopropylmagnesium bromide, isopropylmagnesium chloride)

in an organic solvent (tetrahydrofuran, diethyl ether, and the like) at temperatures from −78 to 60° C., and then reacting the compound represented by the general formula (3-h) in an organic solvent (tetrahydrofuran, diethyl ether, and the like) at temperatures from −78 to 60° C.

In the reaction scheme 3, protection reactions of a hydroxyl group shown in the reactions 9, 12, and 14 are carried out if necessary. The protection reaction is carried out by, for example, reacting the compounds represented by the general formulae (3-e), (3-f), and (3-k) with a silylating agent (chlorotrimethylsilane, chlorotriethylsilane, chloro-tert-butyl dimethylsilane, chloro-tert-butyl diphenylsilane, and the like) in an organic solvent (tetrahydrofuran, dichloromethane, and the like) in the presence of a base (imidazole, triethylamine, and the like) at temperatures from 0° C. to room temperature.

The protective groups are not particularly limited to the above-described groups, and may include, in addition to the above-mentioned groups, groups that can be detached easily and selectively. For example, those described in "Protective Groups in Organic Synthesis (T. W. Greene, John Wiley & Sons Inc, 1999)" may be used.

In the reaction scheme 3, the reduction reactions of a nitro group shown in the reactions 10 and 13 are carried out with respect to the compound represented by the general formula (3-e) or (3-i) in a solvent (ethers (tetrahydrofuran, dioxane, dimethoxyethane, diethyl ether, and the like), alcohols (methanol, ethanol, and the like), benzenes (benzene, toluene, and the like), ketones (acetone, methyl ethyl ketone, and the like), nitriles (acetonitrile, and the like), amides (dimethylformamide, and the like), water, ethyl acetate, acetic acid, or a mixture of two or more thereof, etc.) in the presence of a catalyst (palladium-carbon, palladium black, palladium hydroxide, platinum oxide, Raney nickel, etc.) under hydrogen atmosphere at normal pressure or elevated pressure, or in the presence of ammonium formate at temperatures of about 0 to 200° C. Alternatively, the reaction is carried out using a metal reagent (zinc, iron, tin, tin chloride, iron chloride, samarium, indium, sodium borohydride-nickel chloride and the like) in a water-miscible solvent (ethanol, methanol, tetrahydrofuran, and the like), in the presence or absence of acids (hydrochloric acid, hydrobromic acid, ammonium chloride, acetic acid, ammonium formate, and the like) at temperatures of about 0 to 150° C.

In the reaction scheme 3, the deprotection reaction of an amino group shown in the reactions 11 and 15 can be carried out by the following method.

The deprotection reaction of an amino group is well known, and can be carried out by the methods mentioned below. Examples thereof include:
(1) a deprotection reaction by alkaline hydrolysis,
(2) a deprotection reaction in acidic conditions,
(3) a deprotection reaction by hydrogenolysis,
(4) a deprotection reaction of a silyl group,
(5) a deprotection reaction using metal,
(6) a deprotection reaction using a metal complex, and the like.

These deprotection reaction can be carried out in the same manner as in the deprotection of a hydroxyl group described above.

The protective groups are not particularly limited to the above-described groups, and may include, in addition to the above-mentioned groups, groups that can be detached easily and selectively. For example, those described in "Protective Groups in Organic Synthesis (T. W. Greene, John Wiley & Sons Inc, 1999)" may be used.

Herein, in the compound represented by the general formula (3-n), when any one of $R^{41}$ and $R^{51}$ is a hydrogen atom, if necessary, or when both of $R^{41}$ and $R^{51}$ are simultaneously a hydrogen atom, the compound represented by the general formula (3-n) is subjected to the halogenation reaction shown in the reaction 16.

In the reaction scheme 3, the halogenation reaction shown in the reaction 16 is carried out by reacting the compound represented by the general formula (3-n) with a halogenation reagent (N-chlorosuccinimide, 1,3-dichloro-5,5-dimethylhydantoin, N-bromosuccinimide, N-iodosuccinimide, and the like) in an organic solvent (acetonitrile, N,N-dimethylformamide, and the like) at temperatures from 0 to 80° C.

A compound represented by the general formula (I) in which $R^{11}$ is $NH_2$, and Y is —NH— or —O—, that is, a compound represented by the general formula (4-a) (wherein $Y_1$ is —NH— or —O—, the other symbols represent the same meanings as mentioned above) can be produced by a method shown in the reaction scheme 4 (wherein all of the symbols represent the same meanings as mentioned above) using the compound represented by the general formula (SM2).

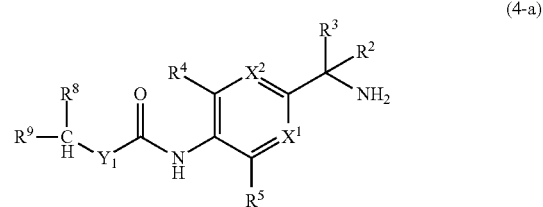
(4-a)

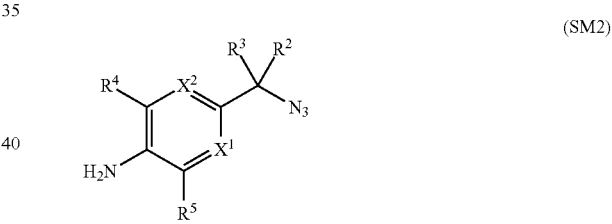
(SM2)

Reaction scheme 4

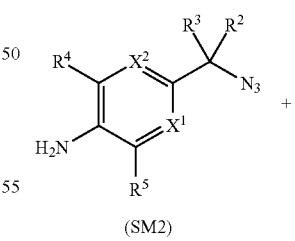
(SM2)

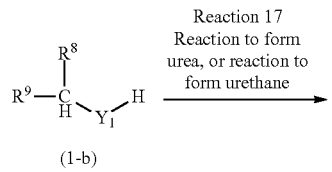
Reaction 17
Reaction to form urea, or reaction to form urethane (1-b)

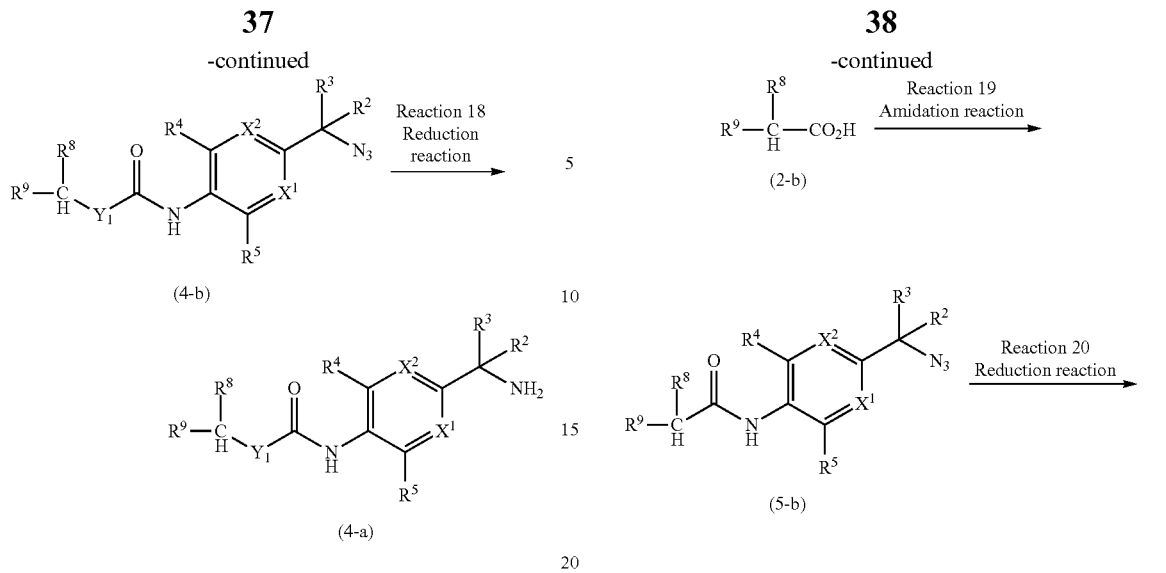

In the reaction scheme 4, the reaction to form urea, or the reaction to form urethane shown in the reaction 17 can be carried out by the same method as in the reaction 1 described in the reaction scheme 1 above.

In the reaction scheme 4, the reduction reaction of an azide group shown in the reaction 18 is carried out by reacting triphenylphosphine in a mixed solvent of an organic solvent (tetrahydrofuran, dimethyl ethyl ether, and the like) and water at room temperature. Furthermore, the reaction is also carried out by reacting lithium aluminum hydride in the organic solvent (tetrahydrofuran, and the like) while heating and refluxing from 0° C.

A compound represented by the general formula (I) in which $R^{11}$ is $NH_2$, and Y is a bond, that is, a compound represented by the general formula (5-a) (wherein all of the symbols represent the same meanings as mentioned above) can be produced by a method shown in the reaction scheme 5 (wherein all of the symbols represent the same meanings as mentioned above) using the compound represented by the general formula (SM2).

In the reaction scheme 5, the amidation reaction shown by the reaction 19 can be carried out by the same method as in the reaction 3 described in the reaction scheme 2 described above.

In the reaction scheme 5, the reduction reaction shown by the reaction 20 can be carried out by the same method as in the reaction 18 described in the reaction scheme 4 above.

The compound represented by the general formula (SM2) can be produced by the method shown by the reaction scheme 6 (wherein all of the symbols represent the same meanings as mentioned above) using the compound represented by general formula (SM1) as a starting material.

Reaction scheme 5

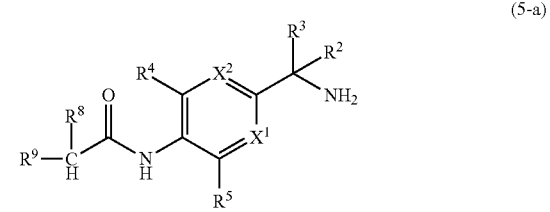

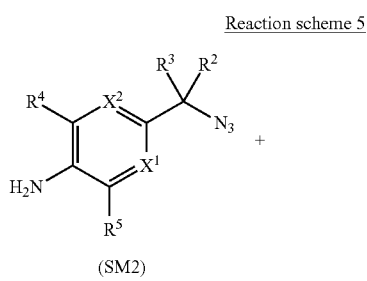

Reaction scheme 6

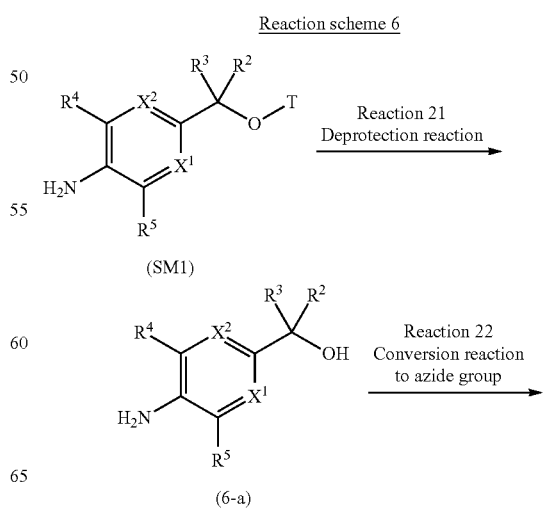

-continued

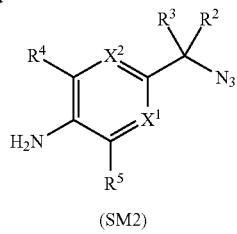

(SM2)

In the reaction scheme 6, the deprotection reaction of a hydroxyl group shown by the reaction 21 can be carried out in the same manner as in the deprotection reaction of a hydroxyl group shown by the reaction scheme 1 above.

In the reaction scheme 6, the conversion reaction of a hydroxyl group into an azide group is carried out by reacting the compound represented by the general formula (6-a) with sodium azide or potassium azide in an organic solvent (chloroform, dichloromethane, and the like), in the presence of trifluoroacetic acid, at room temperature. Furthermore, the reaction is also carried out by reacting diphenyl phosphorazidate and 2,3,4,6,7,8,9,10-octahydropyrimido[1,2-a]azepine in the organic solvent (toluene, tetrahydrofuran, and the like) at temperatures from 0° C. to room temperature.

An optically active substance of the compound represented by the general formula (I) can be produced by a routine procedure (for example, an optical resolution method using a chiral column, and the like). Furthermore, the optically active substance of the compound represented by the general formula (I) can also be produced by the method shown in the above reaction scheme by using the optical isomer of the compounds represented by the general formulae (3-c), (3-e), (3-f), (3-i), (3-k), (3-m), (3-n), (SM1), (4-b), (5-b), (6-a), and (SM2) separated in advance by an optical resolution method such as a routine procedure (for example, an optical resolution method using a chiral column, and the like) or the method described in the Examples of the present specification.

In each reaction of the present specification, the compounds represented by the general formulae (1-b), (2-b), (3-a), (3-b), (3-d), (3-g), and (3-h) used as a starting material or a reagent are well-known in itself, or can be easily produced by Examples described in the present specification or by a well-known methods.

In each reaction in the present specification, as is apparent to a skilled person in the art, the reactions involving heating can be carried out using a water bath, an oil bath, a sand bath or a microwave.

In each reaction in the present specification, a solid-supported reagent which is supported on a high molecular polymer (for example, polystyrene, polyacrylamide, polypropylene, polyethylene glycol, and the like) may be appropriately used.

In each reaction in the present specification, reaction products can be purified by usual purification methods, for example, by distillation at normal or reduced pressure, by high performance liquid chromatography using silica gel or magnesium silicate, thin layer chromatography, ion-exchange resin, scavenger resin, or column chromatography, or washing, recrystallization, or the like. The purification may be carried out after each reaction or after several reactions.

[Toxicity]

The compound of the present invention has sufficiently low toxicity, and can be safely used as pharmaceuticals.

[Application to Pharmaceuticals]

The compound of the present invention is suitable for preventing and/or treating KCNQ2-5 channel-related diseases.

The compound of the present invention can be used for preventing and/or treating KCNQ2-5 channel-related diseases. Examples of the diseases include epilepsy, pain disorders (for example, neurogenic pain, and migraine), diabetic peripheral nerve disorders, anxiety disorder, mood adjustment disorders, schizophrenic disorder, drug dependence, attention adjustment disorders, sleep disorders, cerebral stroke, tinnitus, memory disorders (for example, Alzheimer's disease, and dementia), amyotrophic lateral sclerosis, movement disorders (for example, Parkinson's disease, and dystonia-related movement disorder), dysuria (for example, overactive urinary bladder, urinary frequency, nocturia, urinary urgency, urge urinary incontinence, stress urinary incontinence, interstitial cystitis, chronic prostatitis, and benign prostatic hypertrophy), hardness of hearing, asthma, chronic obstructive pulmonary disease, coughing, pulmonary hypertension, neurodegenerative disease of visual organ (for example, glaucoma, progressive diabetic retinopathy, maculopathy with aging, retinal pigmentary degeneration), Diabetes Mellitus, and the like.

The compound of the present invention is suitable for preventing and/or treating preferably dysuria.

The compound of the present invention is suitable for preventing and/or treating more preferably overactive urinary bladder.

The overactive urinary bladder is symptoms syndromes involving certainly urinary urgency, usually urinary frequency and nocturia, and sometimes urine incontinence.

When the compound of the present invention is used for preventing and/or treating dysuria, in order to avoid central nervous system adverse effects such as dizziness and sleepiness, it is preferable that the intracerebral migration of the compound of the present invention is low. Therefore, the compound of the present invention is preferably a compound having the reduced intracerebral migration. The intracerebral migration can be evaluated by, for example, intracerebral content or the calculated intracerebral migration rate (intracerebral content/plasma concentration) obtained by administering a test substance to mammals (for example, rat and mouse) by oral administration or intravenous administration, and measuring the plasma concentration and/or the intracerebral content after the administration (for example, one hour after the administration).

The compound of the present invention may be administered as a combination drug in combination with other drugs in order to accomplish the following purposes:
1) to supplement and/or enhance the preventive and/or therapeutic effect;
2) to improve the kinetics, improvement of absorption, and to reduce the dose; and/or
3) to eliminate the adverse effects.

A combination drug of the compound of the present invention and one or more of other drugs may be administered in the form of a compounding agent including all the components mixed into one formulation, or may be administered in separate formulations. Administration as separate formulations includes simultaneous administration and administration at different times. In the administration at different times, the compound of the present invention may be administered before the other drug. Alternatively, the other drug may be administered before the compound of the present invention. The method for the administration of these drugs may be the same as or different from each other.

Diseases on which the preventive and/or therapeutic effect of the above-mentioned combination drug works are not particularly limited but may be those in which the preventive and/or therapeutic effect of the compound of the present invention is supplemented and/or enhanced.

Examples of other drugs to supplement and/or enhancement for preventive and/or therapeutic effect for overactive urinary bladder by the compound of the present invention include: (1) muscarinic receptor antagonists (for example, tolterodine, oxybutynin, hyoscyamine, propantheline, propiverine, trospium, solifenacin, dalifenacin, imidafenacin, fesoterodine, temiverine, flavoxate, tarafenacin, afacifenacin, THVD-101, THVD-201, and the like), (2) β3 adrenergic receptor agonist (Mirabegron, KRP-114V, Solabegron, TRK-380, and the like), (3) NK-1 or -2 antagonist (for example, aprepitant, cizolirtine, and the like), (4) genetically modified botulinus toxin (senrebotase, and the like), (5) opioid μ receptor agonist (TRK-130 or the like), (6) α4β2 nicotinic acetylcholine receptor antagonist (dexmecamylamine or the like), (7) C-fiber inhibitor (Besipirdine, or the like), (8) TRPV1 antagonist (XEN-D0501, or the like), (9) EP1 antagonist (KEA-0447, or the like), (10) central nervous system drug (REC-1819, or the like), (11) al adrenergic receptor antagonist (for example, Tamsulosin, Silodosin, Naftopidil, Urapidil, and the like), (12) 5α reductase inhibitor (Dutasteride, finasteride, and the like), (13) phosphodiesterase 5 inhibitor (Sildenafil, Tadalafil, Vardenafil), (14) vasopressinV2 receptor agonist (desmopressin), or the like.

A dosage of the other drugs can be appropriately selected on the basis of the clinical dose. Further, a mixing proportion of the compound of the present invention and the other drugs can be appropriately selected on the basis of age and body weight of a subject, medication method, administration period, disease, symptoms or combination thereof, and the like. For example, 0.01 to 100 parts by mass of the other drugs for one part by mass of the compound of the present invention may be used. Any two or more other drugs may be administered in combination at a suitable proportion. Furthermore, the other drugs include not only drugs which have been found to date but also drugs that will be found in the future.

When the compound of the present invention or combination agents of the compound of the present invention and other agents are used for the above-mentioned purposes, they are usually administered systemically or locally, usually by oral or parenteral administration after, usually, they are formulated together with pharmaceutically acceptable carrier in an appropriate pharmaceutical composition.

The compound of the present invention is administered to mammal (preferably, human, and more preferably, patient) in an effective amount.

Since doses of the compound of the present invention are dependent on ages, body weight, symptoms, desired therapeutic effect, administration route, treatment time, and the like, it inevitably varies. The doses per patient are generally from 0.1 mg to 1000 mg per dose, once to several times per day, by oral administration, or from 0.01 mg to 100 mg per dose, once or several times per day, by parenteral administration, or continuous administration for 1 to 24 hours per day intravenously.

Needless to say, as mentioned above, the doses to be used vary dependent upon various conditions. Therefore, doses lower than the ranges specified above may be sufficient in some cases, and doses higher than the ranges specified above are needed in some cases.

When the compound of the present invention or the combined preparation of the compound of the present invention and other pharmaceutical is administered, it is used as internal solid composition and internal liquid composition for oral administration, sustained release preparation and controlled release preparation for oral administration, and injection, external preparation, inhalant, suppository for parenteral administration, or the like.

Examples of the internal solid composition for oral administration includes tablets, pills, capsules, powder and granules. The capsules include hard capsules and soft capsules.

In such a solid composition, one or more active substance(s) is used by itself or by being mixed with vehicle (for example, lactose, mannitol, glucose, microcrystalline cellulose, and starch, and the like), binding agent (for example, hydroxypropylcellulose, polyvinyl pyrrolidone, and magnesium aluminometasilicate, and the like), disintegrator (for example, calcium carboxymethylcellulose and the like), lubricant (for example, magnesium stearate and the like), stabilizer, a dissolution aid (for example, glutamic acid, aspartic acid, and the like), and the like, and being pharmaceutically manufactured by a conventional method. The solid composition may be coated with coating (for example, saccharose, gelatin, hydroxypropylcellulose or hydroxypropylmethylcellulose phthalate, and the like), if necessary, or may be coated with two or more layers. Capsule of a substance that can be absorbed, such as gelatin, is also included.

The internal liquid composition for oral administration includes pharmaceutically acceptable solution, suspension, emulsum, syrup and elixir, and the like. In the liquid composition, one or more active substance(s) is dissolved, suspended or emulsified in a commonly used inert diluent (for example, purified water, ethanol or the mixture thereof, and the like). The composition may contain humectant, suspending agent, emulsifying agent, sweetener, flavor, aromatic agent, preservative and buffer, and the like.

Furthermore, the sustained release preparation in oral administration is also effective. A gel formation substance to be used for these sustained release preparation is a substance that is swelled by including a solvent, the colloid particles thereof are linked to each other to form a three-dimensional network structure, and can form a jelly-like substance which has lost fluidity. In preparation, it is mainly used as a binding agent, a thickener, and sustained release base material. For example, gum arabic, agar, polyvinyl pyrrolidone, sodium alginate, propylene glycol alginate, carboxyvinyl polymer, carboxymethyl cellulose, sodium carboxymethylcellulose, guar gum, gelatin, hydroxypropylmethyl cellulose, hydroxypropyl cellulose, polyvinyl alcohol, methyl cellulose, or hydroxyethyl methyl cellulose, can be used.

The injection agents for parenteral administration include solutions, suspensions, emulsions and solid injection agents to be dissolved in a solvent before use. The injection agent is used by dissolving, suspending or emulsifying one or more active substance(s) in a solvent. Examples of the solvent include distilled water for injection, physiological saline, vegetable oils, alcohols such as propylene glycol, polyethylene glycol, ethanol, and mixtures thereof. Furthermore, the injection agent may contain a stabilizer, a dissolution aid (glutamic acid, aspartic acid, and Polysorbate 80 (registered trademark), and the like), a suspending agent, an emulsifying agent, a soothing agent, a buffer, a preservative, and the like. Such an injection agent is produced by sterilizing at the final step or employing an aseptic process. Furthermore, it is also possible to employ as an aseptic solid product (for example, produced freeze-dried product is dissolved in distilled water for injection or other solvent, wherein the said distilled water for injection or other solvent are aseptic or are sterilized before use).

Examples of the external preparation for parenteral administration includes a nebulizer, an inhalant, a spray agent, an aerosol agent, ointments, gels, creams, poultices, plasters, liniments, and nasal agents. These may contain one or more active substance(s) and may be prepared by well-known methods or conventional methods.

The nebulizer, an inhalant, and a spray agent may contain a stabilizer such as sodium hydrogen sulfite, a buffer agent that provides isotonicity, and an isotonic agent, for example, sodium chloride, sodium citrate, or citric acid, other than a generally used diluent. The method for producing a spray agent is described in detail in, for example, U.S. Pat. No. 2,868,691 and U.S. Pat. No. 3,095,355.

The inhalation agent for parenteral administration includes aerosol preparation, powder for inhalation and liquid for inhalation. The liquid for inhalation may be a form such as the ingredient is dissolved or suspended in water or in other appropriate medium at time of use.

Those inhalation agents are prepared according to well-known methods.

For example, in the case of liquid for inhalation, an antiseptic agent (for example, benzalkonium chloride, paraben, and the like), a coloring agent, a buffer (for example, sodium phosphate, sodium acetate, and the like), an isotonizing agent (for example, sodium chloride, concentrated glycerol, and the like), a thickener (carboxyvinyl polymer and the like), an absorption promoter, and the like, are appropriately selected and prepared if necessary.

In the case of powder for inhalation, lubricant (for example, stearic acid, salt thereof, and the like), a binder (for example, starch, dextrin, and the like), an excipient (for example, lactose, cellulose, and the like), a coloring agent, antiseptic (for example, benzalkonium chloride or paraben, and the like), or absorption promoter, and the like, are appropriately selected and prepared if necessary.

In the administration of the liquid for inhalation, a spraying device (for example, atomizer, nebulizer, or the like) is usually used. In the administration of the powder for inhalation, an administering device for inhalation of powdery pharmaceutical is usually used.

An ointment is produced by well-known methods or generally used prescriptions. For example, an ointment is produced by mixing or melting of one or more active substance(s) into base material. The ointment base material is selected from well-known material or generally used material. For example, a single material or a mixture of two or more of materials are selected from higher fatty acids and higher fatty acid esters (for example, adipic acid, myristic acid, palmitic acid, stearic acid, oleic acid, adipate esters, myristate esters, palmitate esters, stearate esters, and oleate esters), waxes (for example, beeswax, spermaceti, and ceresin), surfactants (for example, polyoxyethylene alkyl ether phosphate esters), higher alcohols (for example, cetanol, stearyl alcohol, and cetostearyl alcohol), silicone oils (for example, dimethylpolysiloxane), hydrocarbons (for example, hydrophilic petrolatum, white petrolatum, purified lanolin, and liquid paraffin), glycols (for example, ethylene glycol, diethylene glycol, propylene glycol, polyethylene glycol, and macrogol), plant oils (for example, castor oil, olive oil, sesame oil, and turpentine oil), animal oils (for example, mink oil, egg yolk oil, squalane, and squalene), water, absorption promoters, and anti-rash agents. Furthermore, a humectant, preservative, stabilizer, anti-oxidant, an aromatizing agent, and the like, may be included.

The gel is prepared by well-known methods or usually used methods. For example, it may be prepared by melting one or more active substance(s) into a base. The gel base is chosen from well-known or usually used ones. For example, it is used by mixing with one or more base(s) chosen from lower alcohol (for example, ethanol and isopropyl alcohol, and the like), gelatinizer (for example, carboxymethylcellulose, hydroxyethylcellulose, hydroxypropylcellulose or ethylcellulose, etc.), neutralizer (for example, triethanolamine or diisopropanolamine, etc.), surfactant (for example, polyethylene glycol monostearate etc.), gums, water, absorption promoter and anti-rash agents. Further, it may include preservative, anti-oxidant or flavor, etc.

The cream is prepared by known or commonly used formulation. For example, a cream is produced by melting or emulsifying one or more active substance(s) in a base. The cream base is selected from known or commonly used bases. Examples of the cream base include higher fatty acid esters, lower alcohols, hydrocarbons, polyhydric alcohols (such as propylene glycol and 1,3-butylene glycol), higher alcohols (such as 2-hexyldecanol and cetanol), emulsifying agents (such as polyoxyethylene alkyl ethers and fatty acid esters), water, absorption enhancers, and anti-rash agents. From these bases, one base is selected and used singly or two or more bases are selected and used in admixture. The cream may further contain a preservative, an anti-oxidant, an aromatizing agent, or the like.

The poultice is produced according to a known or commonly used formulation. For example, a poultice is produced by melting one or more active substance(s) in a base to form a kneaded material, followed by applying and spreading the kneaded material on a support. The poultice base is selected from known or commonly used bases. Examples of the poultice base include viscosity increasing agents (for example, polyacrylic acid, polyvinylpyrrolidone, gum arabic, starch, gelatin, and methyl cellulose), humectants (for example, urea, glycerin, and propylene glycol), fillers (for example, kaolin, zinc oxide, talc, calcium, and magnesium), water, dissolution aids, tackifiers, and anti-rash agents. From these bases, one base is selected and used singly or two or more bases are selected and used in admixture. The poultice may further contain a preservative, an anti-oxidant, an aromatizing agent, or the like.

The plaster is produced according to a known or commonly used formulation. For example, a plaster is produced by melting one or more active substance(s) in a base and applying and spreading the melt on a support. The plaster base is selected from known or commonly used bases. Examples of the plaster base include polymeric bases, oils and fats, higher fatty acids, tackifiers, and anti-rash agents. From these bases, one base is selected and used alone or two or more bases are selected and used in admixture. The plaster may further contain a preservative, an antioxidant, an aromatizing agent, or the like.

The liniment is produced according to a known or commonly used formulation. For example, a liniment is prepared by dissolving, suspending, or emulsifying one or more active substances in one or more materials selected from water, an alcohol (for example, ethanol or polyethylene glycol), a higher fatty acid, glycerin, a soap, an emulsifying agent, and a suspending agent. The liniment may further contain a preservative, an anti-oxidant, an aromatizing agent, or the like.

Examples of the other compositions for parenteral administration include suppositories for intrarectal administration, pessaries for intravaginal administration, and the like, each containing one or more active substance(s) and formulated according to routine procedure.

The entire contents of all Patent Literature and Non Patent Literature or Reference Literature explicitly cited in this description can be incorporated herein by reference as a part of this description.

EXAMPLES

Hereinafter, the present invention will be described in detail by Examples. However, the present invention is not limited to the Examples.

The solvents in the parenthesis indicated in the separated portion by the chromatography and TLC represent eluting or developing solvents used and their ratio is volume ratio.

In the present invention, for column chromatography on silica gel, CHROMATOREX (registered trademark) manufactured by Fuji Silysia Chemical LTD., Yamazen High flash column (product name) and the like were used, as a purifier, for example, a medium-pressure preparative liquid chromatograph, W-prep 2XY (product name) manufactured by Yamazen Corporation was used.

NMR data is the data of $^1$H-NMR unless otherwise stated.

Inside parentheses of NMR represents a solvent used for measurement.

Name of the compounds used in the present specification are named by using ACD/Name (registered trademark) manufactured by Advanced Chemistry Development Inc., which is a computer program for naming compounds according to the regulation of IUPAC, or named according to the naming method of IUPAC.

In the present invention, retention time of an analysis by liquid chromatography (LC) was measured by using the following instruments and in the following conditions.
Analyzer: ACQUITY UPLC I-Class system (manufactured by Waters)
Detector: UV (PDA), ELSD, MS
Condition 1
  Column: ACQUITY UPLC BEH C18 Column (manufactured by Waters, 1.7 μm, 2.1 mm×30 mm)
  Mobile phase: Liquid A: 0.1% formic acid aqueous solution; Liquid B: 0.1% formic acid-acetonitrile solution
  Gradient: 0 min (Liquid A/Liquid B=95/5); 0.1 min (Liquid A/Liquid B=95/5); 1.2 min (Liquid A/Liquid B=5/95); 1.4 min (Liquid A/Liquid B=5/95); 1.5 min (Liquid A/Liquid B=95/5)
  Flow rate: 1 mL/min,
  Detection method: 254 nm,
  Column temperature: 30° C.,
  Filling amount: 2 μL
Condition 2
  Column: ACQUITY UPLC BEH C18 Column (manufactured by Waters, 1.7 μm, 2.1 mm×30 mm)
  Mobile phase: Liquid A: 0.1% trifluoroacetic acid aqueous solution; Liquid B: 0.1% trifluoroacetic acid-acetonitrile solution
  Gradient: 0 min (Liquid A/Liquid B=95/5); 0.1 min (Liquid A/Liquid B=95/5); 1.2 min (Liquid A/Liquid B=5/95); 1.4 min (Liquid A/Liquid B=5/95); 1.5 min (Liquid A/Liquid B=95/5)
  Flow rate: 1 mL/min,
  Detection method: 254 nm,
  Column temperature: 30° C.,
  Filling amount: 2 μL
Condition 3
  Column: YMC Triart C18 (manufactured by YMC, 1.9 μm, 2.1 mm×30 mm)
  Mobile phase: Liquid A: 0.1% trifluoroacetic acid aqueous solution; Liquid B: 0.1% trifluoroacetic acid-acetonitrile solution
  Gradient: 0 min (Liquid A/Liquid B=95/5); 0.1 min (Liquid A/Liquid B=95/5); 1.2 min (Liquid A/Liquid B=5/95); 1.4 min (Liquid A/Liquid B=5/95); 1.5 min (Liquid A/Liquid B=95/5)
  Flow rate: 1 mL/min,
  Detection method: 254 nm,
  Column temperature: 30° C.,
  Filling amount: 2 μL Example 1

1,1,1-trifluoro-2-(4-nitrophenyl)-2-propanol

To a tetrahydrofuran solution (16 mL) of 1-(4-nitrophenyl)ethanone (1.65 g) (CAS registry number: 100-19-6) and (trifluoromethyl)trimethylsilane (4.26 g), tetrabutyl ammonium fluoride (1 M tetrahydrofuran solution, 1 mL) was added under ice-cooling. The resulting solution was stirred at room temperature for two hours. A saturated ammonium chloride aqueous solution was added to the reaction mixture, followed by extraction with ethyl acetate. The organic layer was washed sequentially with water and saturated brine, and dried over anhydrous sodium sulfate, followed by concentration under reduced pressure. The resulting residue was dissolved in tetrahydrofuran (16 mL), and tetrabutyl ammonium fluoride (1 M tetrahydrofuran solution, 12 mL) was added thereto under ice-cooling. The reaction mixture was stirred for ten minutes under ice-cooling, and then concentrated under reduced pressure. The resulting residue was purified by column chromatography on silica gel (hexane:ethyl acetate=85:15→80:20) to obtain the title compound (2.28 g) having the following physical property values.

TLC: Rf 0.47 (hexane:ethyl acetate=3:1);
$^1$H-NMR (CDCl$_3$): δ 1.83-1.84, 7.78-7.81, 8.23-8.28.

Example 2

2-(4-aminophenyl)-1,1,1-trifluoro-2-propanol

The compound (2.28 g) produced in Example 1 was suspended in ethanol (50 mL) and water (10 mL), and powder zinc (3.17 g) and acetic acid (2.82 mL) were added thereto. The reaction mixture was stirred over night at 50° C. The reaction mixture was cooled to room temperature. A saturated sodium hydrogencarbonate aqueous solution was added to the mixture, and the resulting mixture solution was stirred for 30 minutes. To the reaction mixture, ethyl acetate was added. The resulting mixture was filtered through a Celite (product name), and the filtrate was extracted with ethyl acetate. The organic layer was washed with saturated brine, was dried over anhydrous magnesium sulfate, and then concentrated under reduced pressure. The resulting residue was purified by column chromatography on silica gel (hexane:ethyl acetate=80:20→20:80) to obtain the title compound (1.20 g) having the following physical property values.

TLC: Rf 0.37 (hexane:ethyl acetate=2:1);

$^1$H-NMR (CDCl$_3$): δ 1.72-1.73, 2.32, 6.65-6.70, 7.33-7.35.

Example 3

2-(4-amino-3,5-dichlorophenyl)-1,1,1-trifluoro-2-propanol

To an N,N-dimethylformamide solution (12 mL) of the compound (1.20 g) produced in Example 2, N-chlorosuccinimide (1.56 g) was added, and the resulting solution was stirred at room temperature for 15 hours. Water was added to reaction mixture, followed by extraction with ethyl acetate. The organic layer was dried over anhydrous magnesium sulfate, and then concentrated under reduced pressure. The resulting residue was purified by column chromatography on silica gel (hexane:ethyl acetate=80:20→40:60) to obtain the title compound (867 mg) having the following physical property values.

TLC: Rf 0.72 (hexane:ethyl acetate=2:1);
$^1$H-NMR (CDCl$_3$): δ 1.72-1.73, 2.40, 7.39.

Example 4

2,6-dichloro-4-{1,1,1-trifluoro-2-[(trimethylsilyl)oxy]-2-propanyl}aniline

To a tetrahydrofuran solution (17 mL) of the compound (860 mg) produced in Example 3, imidazole (1.07 g) and chlorotrimethylsilane (2 mL) were added. The reaction mixture was stirred at room temperature for 2.5 hours, and water was added thereto, followed by extraction with ethyl acetate. The organic layer was washed with water, dried over anhydrous sodium sulfate, and then concentrated under reduced pressure. The resulting residue was purified by column chromatography on silica gel (hexane:ethyl acetate=100:0→60:40) to obtain the title compound (1.05 g) having the following physical property values.

TLC: Rf 0.68 (hexane:ethyl acetate=8:1);
$^1$H-NMR (CDCl$_3$): δ 0.15, 1.74-1.75, 4.51, 7.33.

Example 5

1-[2,6-dichloro-4-(1,1,1-trifluoro-2-hydroxy-2-propanyl)phenyl]-3-{[5-(trifluoromethyl)-2-pyridinyl]methyl}urea

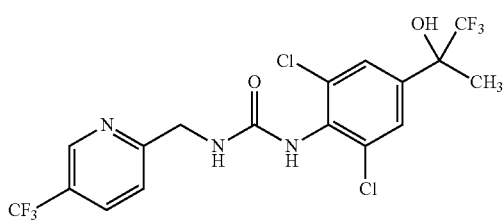 [SMILES: CC(O)(c1cc(Cl)c(NC(=O)NCc2ccc(C(F)(F)F)cn2)c(Cl)c1)C(F)(F)F]

To a tetrahydrofuran solution (9.5 mL) of the compound (475 mg) produced in Example 4, N,N-diisopropyl ethyl amine (261 µL) and triphosgene (447 mg) were added. The reaction mixture was stirred at room temperature for 2.5 hours, followed by concentration under reduced pressure. The resulting residue was dissolved in tetrahydrofuran (1.4 mL), and 1-[5-(trifluoromethyl)-2-pyridinyl]methanamine hydrochloride (583 mg) (CAS registry number: 164341-39-3) and triethylamine (401 µL) were added to the resulting mixture. The resulting mixture was stirred at room temperature overnight. Water was added to the reaction mixture, followed by extraction with ethyl acetate. The organic layer was dried over anhydrous magnesium sulfate, and concentrated under reduced pressure. The resulting residue was dissolved in methanol (10 mL) and dichloromethane (10 mL), and trifluoroacetic acid (4 mL) was added thereto. The reaction mixture was stirred at room temperature overnight, and then stirred at 50° C. for two hours. The reaction mixture was concentrated under reduced pressure, and a saturated sodium hydrogencarbonate aqueous solution was added thereto, followed by extraction with ethyl acetate. The organic layer was dried over anhydrous magnesium sulfate, and concentrated under reduced pressure. The resulting residue was purified by column chromatography on silica gel (hexane:ethyl acetate=60:40→30:70) to obtain the title compound (447 mg) having the following physical property values.

TLC: Rf 0.31 (hexane:ethyl acetate=1:1);
$^1$H-NMR (DMSO-d$_6$): δ 1.69, 4.47, 6.93, 7.14, 7.58, 7.64, 8.24, 8.43, 8.89.

Examples 5(1) to (35)

The corresponding amine instead of 1-[5-(trifluoromethyl)-2-pyridinyl] methanamine hydrochloride was used and subjected to the same procedure as in Example 5 to obtain the title compound having the following physical property values.

Example 5(1)

1-[2,6-dichloro-4-(1,1,1-trifluoro-2-hydroxy-2-propanyl)phenyl]-3-(4-fluorobenzyl)urea TLC: Rf 0.54 (hexane:ethyl acetate=1:1);
$^1$H-NMR (DMSO-d$_6$): δ 1.69, 4.26, 6.89, 6.92, 7.10-7.19, 7.28-7.37, 7.63, 8.15.

Example 5(2)

1-[2,6-dichloro-4-(1,1,1-trifluoro-2-hydroxy-2-propanyl)phenyl]-3-[(5-fluoro-2-pyridinyl)methyl]urea TLC: Rf 0.44 (hexane:ethyl acetate=1:2);
$^1$H-NMR (DMSO-d$_6$): δ 1.69, 4.37, 6.93, 7.05, 7.41, 7.64, 7.74, 8.36, 8.50.

Example 5(3)

1-[2,6-dichloro-4-(1,1,1-trifluoro-2-hydroxy-2-propanyl)phenyl]-3-{[6-(1-piperidinyl)-2-pyridinyl]methyl}urea TLC: Rf 0.89 (ethyl acetate);
$^1$H-NMR (DMSO-d$_6$): δ 1.50-1.65, 1.69, 3.49-3.52, 4.19, 6.55, 6.65, 6.81, 6.93, 7.46, 7.64, 8.31.

Example 5(4)

1-[2,6-dichloro-4-(1,1,1-trifluoro-2-hydroxy-2-propanyl)phenyl]-3-(3,3-dimethyl-2-butanyl)urea TLC: Rf 0.38 (hexane:ethyl acetate=1:1);
$^1$H-NMR (DMSO-d$_6$): δ 0.87, 0.95, 1.69, 3.44-3.54, 6.24, 6.91, 7.61, 7.83.

Example 5(5)

1-[2,6-dichloro-4-(1,1,1-trifluoro-2-hydroxy-2-propanyl)phenyl]-3-[(2,2-dimethyl tetrahydro-2H-pyran-4-yl) methyl]urea TLC: Rf 0.19 (hexane:ethyl acetate=1:1);
$^1$H-NMR (DMSO-$d_6$): δ 0.91-1.05, 1.11, 1.50-1.54, 1.69, 1.75-1.87, 2.98-2.96, 3.46-3.54, 3.58-3.63, 6.43, 6.92, 7.62, 7.94.

Example 5(6)

1-[2,6-dichloro-4-(1,1,1-trifluoro-2-hydroxy-2-propanyl)phenyl]-3-[(4,4-difluoro-1-hydroxy cyclohexyl) methyl]urea TLC: Rf 0.25 (hexane:ethyl acetate=1:1);
$^1$H-NMR (DMSO-$d_6$): δ 1.43-1.66, 1.69, 1.76-2.15, 3.10, 4.70, 6.50, 6.92, 7.62, 8.16.

Example 5(7)

1-[2,6-dichloro-4-(1,1,1-trifluoro-2-hydroxy-2-propanyl)phenyl]-3-[(3-methyl-2-pyridinyl)methyl]urea TLC: Rf 0.15 (hexane:ethyl acetate=1:1);
$^1$H-NMR (DMSO-$d_6$): δ 1.70, 2.28, 4.40, 6.92, 7.10, 7.25, 7.61, 7.63, 8.39, 8.53.

Example 5(8)

1-[(5-chloro-2-thienyl)methyl]-3-[2,6-dichloro-4-(1,1,1-trifluoro-2-hydroxy-2-propanyl)phenyl]urea TLC: Rf 0.53 (hexane:ethyl acetate=1:1);
$^1$H-NMR (DMSO-$d_6$): δ 1.70, 4.34, 6.82, 6.93-6.94, 7.01, 7.64, 8.21.

Example 5(9)

1-[2,6-dichloro-4-(1,1,1-trifluoro-2-hydroxy-2-propanyl)phenyl]-3-{[3-(trifluoromethyl)-2-pyridinyl]methyl}urea TLC: Rf 0.35 (hexane:ethyl acetate=1:1);
$^1$H-NMR (DMSO-$d_6$): δ 1.69, 4.60, 6.93, 7.11, 7.57, 7.63, 8.19, 8.51, 8.86.

Example 5(10)

1-(cyclohexyl methyl)-3-[2,6-dichloro-4-(1,1,1-trifluoro-2-hydroxy-2-propanyl)phenyl]urea TLC: Rf 0.59 (hexane:ethyl acetate=1:1);
$^1$H-NMR (DMSO-$d_6$): δ 0.80-1.78, 2.91, 6.38, 6.91, 7.61, 7.90.

Example 5(11)

1-[(5-bromo-2-pyridinyl)methyl]-3-[2,6-dichloro-4-(1,1,1-trifluoro-2-hydroxy-2-propanyl)phenyl]urea TLC: Rf 0.50 (hexane:ethyl acetate=1:2);
$^1$H-NMR (DMSO-$d_6$): δ 1.69, 4.34, 6.93, 7.05, 7.34, 7.64, 8.06, 8.37, 8.63.

Example 5(12)

1-[(1-benzyl-1H-imidazole-2-yl)methyl]-3-[2,6-dichloro-4-(1,1,1-trifluoro-2-hydroxy-2-propanyl)phenyl]urea TLC: Rf 0.64 (hexane:ethyl acetate=1:1);
$^1$H-NMR (DMSO-$d_6$): δ 1.69, 4.31, 5.23, 6.87, 6.92, 6.96, 7.16-7.19, 7.28-7.37, 7.62, 8.24.

Example 5(13)

1-[2,6-dichloro-4-(1,1,1-trifluoro-2-hydroxy-2-propanyl)phenyl]-3-[(5-fluoro-1H-indole-2-yl)methyl]urea TLC: Rf 0.53 (dichloromethane:methanol=9:1);
$^1$H-NMR (DMSO-$d_6$): δ 1.70, 4.39, 6.29, 6.81-6.90, 6.93, 7.19-7.23, 7.28-7.33, 7.64, 8.19, 11.02.

Example 5(14)

1-[2,6-dichloro-4-(1,1,1-trifluoro-2-hydroxy-2-propanyl)phenyl]-3-[(2R)-tetrahydro-2-furanyl methyl]urea TLC: Rf 0.43 (hexane:ethyl acetate=1:3);
$^1$H-NMR (DMSO-$d_6$): δ 1.47-1.62, 1.69, 1.72-1.95, 3.01-3.12, 3.13-3.28, 3.59-3.66, 3.75-3.86, 6.45, 6.92, 7.62, 8.08.

Example 5(15)

1-[2,6-dichloro-4-(1,1,1-trifluoro-2-hydroxy-2-propanyl)phenyl]-3-[(2S)-tetrahydro-2-furanyl methyl]urea TLC: Rf 0.43 (hexane:ethyl acetate=1:3);
$^1$H-NMR (DMSO-$d_6$): δ 1.47-1.62, 1.69, 1.72-1.95, 3.01-3.12, 3.13-3.28, 3.59-3.66, 3.75-3.86, 6.45, 6.92, 7.62, 8.08.

Example 5(16)

1-[2,6-dichloro-4-(1,1,1-trifluoro-2-hydroxy-2-propanyl)phenyl]-3-[(5-phenyl-1,2-oxazole-3-yl)methyl]urea TLC: Rf 0.37 (hexane:ethyl acetate=1:1);
$^1$H-NMR (DMSO-$d_6$): δ 1.70, 4.37, 6.85, 6.93, 7.03, 7.43-7.58, 7.65, 7.82, 8.30.

Example 5(17)

1-[2,6-dichloro-4-(1,1,1-trifluoro-2-hydroxy-2-propanyl)phenyl]-3-{[5-(trifluoromethyl)-2-furyl]methyl}urea TLC: Rf 0.58 (hexane:ethyl acetate=1:1);
$^1$H-NMR (DMSO-$d_6$): δ 1.69, 4.33, 6.44, 6.94, 6.97, 7.16, 7.64, 8.25.

Example 5(18)

1-[2,6-dichloro-4-(1,1,1-trifluoro-2-hydroxy-2-propanyl)phenyl]-3-{[5-(trifluoromethyl)-1,2,4-oxadiazole-3-yl]methyl}urea TLC: Rf 0.65 (hexane:ethyl acetate=1:1);
$^1$H-NMR (DMSO-$d_6$): δ 1.69, 4.54, 6.94, 7.14, 7.63, 8.43.

Example 5(19)

1-[2,6-dichloro-4-(1,1,1-trifluoro-2-hydroxy-2-propanyl)phenyl]-3-(3,3,3-trifluoropropyl)urea TLC: Rf 0.28 (hexane:ethyl acetate=1:1);
$^1$H-NMR (DMSO-$d_6$): δ 1.69, 2.26-2.44, 3.27-3.29, 6.55, 6.93, 7.63, 8.22.

Example 5(20)

1-[(1R)-1-cyclopropyl ethyl]-3-[2,6-dichloro-4-(1,1,1-trifluoro-2-hydroxy-2-propanyl)phenyl]urea TLC: Rf 0.30 (hexane:ethyl acetate=1:1);
$^1$H-NMR (DMSO-$d_6$): δ 0.15-0.41, 0.82-0.89, 1.12, 1.69, 3.18-3.25, 6.30, 6.91, 7.61, 7.85.

Example 5(21)

1-[2,6-dichloro-4-(1,1,1-trifluoro-2-hydroxy-2-propanyl)phenyl]-3-[(2R)-3-methyl-2-butanyl]urea TLC: Rf 0.30 (hexane:ethyl acetate=1:1);
$^1$H-NMR (DMSO-$d_6$): δ 0.84-0.88, 1.01, 1.61-1.70, 3.46-3.53, 6.24, 6.91, 7.61, 7.82.

Example 5(22)

1-[(3-cyclopropyl-1,2,4-oxadiazole-5-yl)methyl]-3-[2,6-dichloro-4-(1,1,1-trifluoro-2-hydroxy-2-propanyl)phenyl]urea TLC: Rf 0.17 (hexane:ethyl acetate=1:1);
$^1$H-NMR (DMSO-$d_6$): δ 0.82-0.87, 1.01-1.08, 1.69, 2.05-2.14, 4.47, 6.93, 7.10, 7.63, 8.46.

Example 5(23)

1-[2,6-dichloro-4-(1,1,1-trifluoro-2-hydroxy-2-propanyl)phenyl]-3-{[5-(trifluoromethyl)-1,2-oxazole-3-yl]methyl}urea TLC: Rf 0.45 (hexane:ethyl acetate=1:1);
$^1$H-NMR (DMSO-$d_6$): δ 1.69, 4.42, 6.94, 7.08, 7.18, 7.64, 8.41.

Example 5(24)

1-[(5-chloro-2-pyrimidinyl)methyl]-3-[2,6-dichloro-4-(1,1,1-trifluoro-2-hydroxy-2-propanyl)phenyl]urea TLC: Rf 0.60 (hexane:ethyl acetate=1:3);
$^1$H-NMR (DMSO-$d_6$): δ 1.69, 4.49, 6.92, 7.01, 7.62, 8.42, 8.92.

Example 5(25)

1-[2,6-dichloro-4-(1,1,1-trifluoro-2-hydroxy-2-propanyl)phenyl]-3-{[5-(trifluoromethyl)-2-pyrazinyl]methyl}urea TLC: Rf 0.38 (hexane:ethyl acetate=1:1);
$^1$H-NMR (DMSO-$d_6$): δ 1.69, 4.55, 6.94, 7.21, 7.64, 8.51, 8.78, 9.13.

Example 5(26)

1-[2,6-dichloro-4-(1,1,1-trifluoro-2-hydroxy-2-propanyl)phenyl]-3-{[5-(trifluoromethyl)-2-thienyl]methyl}urea TLC: Rf 0.54 (hexane:ethyl acetate=1:1);
$^1$H-NMR (DMSO-$d_6$): δ 1.70, 4.48, 6.94, 7.05, 7.14, 7.54, 7.64, 8.31.

Example 5(27)

1-[2,6-dichloro-4-(1,1,1-trifluoro-2-hydroxy-2-propanyl)phenyl]-3-{[3-(2-methyl-2-propanyl)-1,2,4-oxadiazole-5-yl]methyl}urea TLC: Rf 0.41 (hexane:ethyl acetate=1:1);
$^1$H-NMR (DMSO-$d_6$): δ 1.29, 1.69, 4.52, 6.93, 7.13, 7.63, 8.47.

Example 5(28)

1-[2,6-dichloro-4-(1,1,1-trifluoro-2-hydroxy-2-propanyl)phenyl]-3-{[5-(2-methyl-2-propanyl)-1,2,4-oxadiazole-3-yl]methyl}urea TLC: Rf 0.36 (hexane:ethyl acetate=1:1);
$^1$H-NMR (DMSO-$d_6$): δ 1.37, 1.69, 4.37, 6.92, 6.99, 7.63, 8.29.

Example 5(29)

1-[2,6-dichloro-4-(1,1,1-trifluoro-2-hydroxy-2-propanyl)phenyl]-3-[4-(trifluoromethyl)benzyl]urea LC retention time (min), LC condition 2: 0.96;
$^1$H-NMR (DMSO-$d_6$): δ 1.68, 4.36, 6.91, 7.00, 7.49-7.51, 7.63, 7.68-7.71, 8.24.

Example 5(30)

1-(cyclopropyl methyl)-3-[2,6-dichloro-4-(1,1,1-trifluoro-2-hydroxy-2-propanyl)phenyl]urea TLC: Rf 0.53 (hexane:ethyl acetate=1:1);
$^1$H-NMR (DMSO-$d_6$): δ 0.16-0.21, 0.38-0.44, 0.89-0.97, 1.70, 2.97, 6.45, 6.93, 7.63, 7.99.

Example 5(31)

1-[2,6-dichloro-4-(1,1,1-trifluoro-2-hydroxy-2-propanyl)phenyl]-3-[(2,2-difluorocyclopropyl)methyl]urea TLC: Rf 0.29 (hexane:ethyl acetate=1:1);
$^1$H-NMR (DMSO-$d_6$): δ 1.24-1.34, 1.51-1.62, 1.70, 1.86-1.99, 3.08-3.29, 6.63, 6.94, 7.64, 8.13.

Example 5(32)

1-[2,6-dichloro-4-(1,1,1-trifluoro-2-hydroxy-2-propanyl)phenyl]-3-(1,2-oxazole-3-yl methyl)urea TLC: Rf 0.34 (hexane:ethyl acetate=1:1);
$^1$H-NMR (DMSO-d$_6$): δ 1.70, 4.35, 6.45, 6.94, 6.99, 7.65, 8.29, 8.83.

Example 5(33)

1-[2,6-dichloro-4-(1,1,1-trifluoro-2-hydroxy-2-propanyl)phenyl]-3-(1,3-thiazole-2-yl methyl)urea TLC: Rf 0.12 (hexane:ethyl acetate=1:1);
$^1$H-NMR (DMSO-d$_6$): δ 1.71, 4.56, 6.95, 7.27, 7.61, 7.65, 7.72, 8.40.

Example 5(34)

1-[2,6-dichloro-4-(1,1,1-trifluoro-2-hydroxy-2-propanyl)phenyl]-3-[(3,3-difluorocyclobutyl)methyl]urea TLC: Rf 0.42 (hexane:ethyl acetate=1:1);
$^1$H-NMR (DMSO-d$_6$): δ 1.70, 2.27-2.65, 3.19, 6.60, 6.93, 7.63, 8.07.

Example 5(35)

1-[2,6-dichloro-4-(1,1,1-trifluoro-2-hydroxy-2-propanyl)phenyl]-3-[4-(trifluoromethoxy)benzyl]urea TLC: Rf 0.55 (hexane:ethyl acetate=1:1);
$^1$H-NMR (CD$_3$OD): δ 1.72, 4.42, 7.22-7.25, 7.43-7.46, 7.66.

Example 6

[2-(2-methyl-2-propanyl)-1,3-oxazole-5-yl]methanol

To a methanol solution (1.3 mL) of [2-(2-methyl-2-propanyl)-1,3-oxazole-5-yl] methyl acetate (52 mg) (Tetrahedron Letters, 2010, vol. 51, p. 2247-2250), potassium carbonate (54 mg) was added under ice-cooling. The reaction mixture was stirred at room temperature for 30 minutes, and then water was added to the mixture, followed by extraction with ethyl acetate. The organic layer was washed sequentially with water and saturated brine, and dried over anhydrous sodium sulfate, followed by concentration under reduced pressure to obtain the title compound (40 mg) having the following physical property values.
TLC: Rf 0.31 (hexane:ethyl acetate=1:1);
$^1$H-NMR (CDCl$_3$): δ 1.39, 1.71, 4.65, 6.88.

Example 7

2-{[2-(2-methyl-2-propanyl)-1,3-oxazole-5-yl]methyl}-1H-isoindole-1,3(2H)-dione

Under argon atmosphere, triphenylphosphine (135 mg) and phthalimide (75 mg) were added to a tetrahydrofuran solution (1 mL) of the compound (40 mg) produced in Example 6. Diethyl azodicarboxylate (230 μL) was added to the reaction mixture under ice-cooling, and the resulting mixture was stirred at room temperature for one hour. The reaction mixture was concentrated. The resulting residue was purified by column chromatography on silica gel (hexane:ethyl acetate=80/20→55/45) to obtain the title compound (93 mg) having the following physical property values.
TLC: Rf 0.64 (hexane:ethyl acetate=1:1);
$^1$H-NMR (CDCl$_3$): δ 1.34, 4.87, 6.93, 7.73-7.78, 7.86-7.90.

Example 8

1-[2-(2-methyl-2-propanyl)-1,3-oxazole-5-yl]methanamine

Under argon atmosphere, hydrazine 1-hydrate (129 mg) was added to an ethanol solution (1.7 mL) of the compound (73 mg) produced in Example 7. The reaction mixture was stirred at 80° C. for 30 minutes, and then cooled to room temperature. To the reaction mixture, a mixed solvent of ethyl acetate and ethanol was added. The resulting mixture solution was filtered. The filtrate was concentrated under reduced pressure to obtain the title compound (40 mg) having the following physical property values.
$^1$H-NMR (CDCl$_3$): δ 1.37, 3.85, 6.74.

Example 9

1-[2,6-dichloro-4-(1,1,1-trifluoro-2-hydroxy-2-propanyl)phenyl]-3-{[2-(2-methyl-2-propanyl)-1,3-oxazole-5-yl]methyl}urea

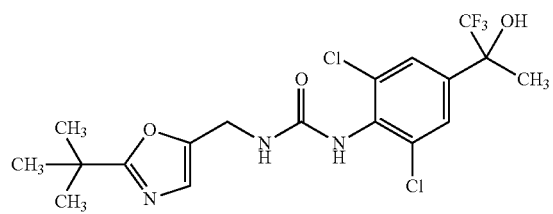 [SMILES: CC(C)(C)c1ncc(CNC(=O)Nc2c(Cl)cc(C(C)(O)C(F)(F)F)cc2Cl)o1]

The compound produced in Example 8 instead of 1-[5-(trifluoromethyl)-2-pyridinyl]methanamine hydrochloride was used and subjected to the same procedure as in Example 5 to obtain the title compound having the following physical property values.
TLC: Rf 0.40 (hexane:ethyl acetate=1:2);
$^1$H-NMR (DMSO-d$_6$): δ 1.29, 1.69, 4.28, 6.78, 6.84, 6.93, 7.64, 8.17.

Example 10

1-[2-(trifluoromethyl)-1,3-thiazole-5-yl]methanamine (2-(trifluoromethyl)thiazole-5-yl)methanol (CAS registry number: 131748-97-5) instead of the compound produced in Example 6 was used and subjected to the same procedure as in Example 7→Example 8 to obtain the title compound having the following physical property values.
$^1$H-NMR (DMSO-d$_6$): δ 2.27, 4.00, 7.91.

Example 11

1-[2,6-dichloro-4-(1,1,1-trifluoro-2-hydroxy-2-propanyl)phenyl]-3-{[2-(trifluoromethyl)-1,3-thiazole-5-yl]methyl}urea

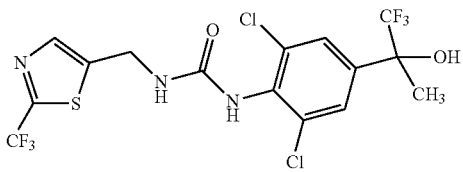 [SMILES: CC(O)(c1cc(Cl)c(NC(=O)NCc2cnc(C(F)(F)F)s2)c(Cl)c1)C(F)(F)F]

The compound produced in Example 10 instead of 1-[5-(trifluoromethyl)-2-pyridinyl]methanamine hydrochloride was used and subjected to the same procedure as in Example 5 to obtain the title compound having the following physical property values.

TLC: Rf 0.26 (hexane:ethyl acetate=1:1);
$^1$H-NMR (DMSO-$d_6$): δ 1.70, 4.53, 6.94, 7.19, 7.65, 7.96, 8.40.

Example 12

1-[5-(2-methyl-2-propanyl)-1,2-oxazole-3-yl]methanamine (5-tert-butyl-1,2-oxazole-3-yl)methanol (CAS registry number: 202817-06-9) instead of the compound produced in Example 6 was used and subjected to the same procedure as in Example 7→Example 8 to obtain the title compound having the following physical property values.

$^1$H-NMR (DMSO-$d_6$): δ 1.27, 3.63, 6.20.

Example 13

1-[2,6-dichloro-4-(1,1,1-trifluoro-2-hydroxy-2-propanyl)phenyl]-3-{[5-(2-methyl-2-propanyl)-1,2-oxazole 3-yl]methyl}urea

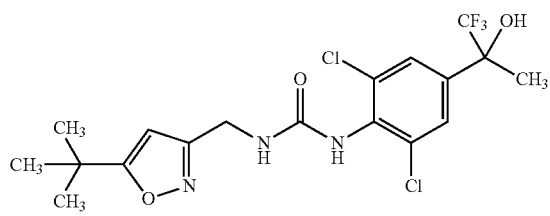 [SMILES: CC(C)(C)c1cc(CNC(=O)Nc2c(Cl)cc(C(C)(O)C(F)(F)F)cc2Cl)no1]

The compound produced in Example 12 instead of 1-[5-(trifluoromethyl)-2-pyridinyl]methanamine hydrochloride was used and subjected to the same procedure as in Example 5 to obtain the title compound having the following physical property values.

TLC: Rf 0.53 (hexane:ethyl acetate=1:1);
$^1$H-NMR (DMSO-$d_6$): δ 1.27, 1.69, 4.26, 6.10, 6.91-6.99, 7.64, 8.27.

Example 14

2-(4-bromophenyl)-1,1,1-trifluoro-2-propanol

Under argon atmosphere, cerium chloride (51 g), which had been heated and dried under reduced pressure, was suspended in tetrahydrofuran (316 mL), stirred at room temperature for one hour, and the resulting mixture was cooled to −70° C. Methyllithium (3.0 M diethyl ether solution, 185 mL) was added dropwise, stirred at −70° C. for 30 minutes. A tetrahydrofuran solution (30 mL) of 1-(4-bromophenyl)-2,2,2-trifluoroethanone (40 g) (CAS registry number: 16184-89-7) was added to the resulting mixture. The resulting solution was stirred at room temperature for 1.5 hours. The reaction solution was poured into a mixed solution of a saturated ammonium chloride aqueous solution (500 mL) and ice water (500 mL), and 1 N hydrochloric acid was added to the resulting solution until the mixture became light yellow, followed by extraction with ethyl acetate. The organic layer was washed sequentially with water and saturated brine, and dried over anhydrous magnesium sulfate, followed by concentration under reduced pressure to obtain the title compound (51 g) having the following physical property values.

TLC: Rf 0.59 (hexane:ethyl acetate=4:1);
$^1$H-NMR (CDCl$_3$): δ 1.77, 2.42, 7.44-7.47, 7.52-7.55.

Examples 15a and 15b (2R)-2-(4-bromophenyl)-1,1,1-trifluoro-2-propanyl [(1S)-1-(1-naphthyl)ethyl]carbamate (15a) and (2S)-2-(4-bromophenyl)-1,1,1-trifluoro-2-propanyl[(1S)-1-(1-naphthyl)ethyl]carbamate (15b)

To a dichloromethane solution (237 mL) of the compound (43 g) produced in Example 14, dimethyl amino pyridine (23.2 g) and 4-nitrophenyl chloroformate (35.1 g) were added under ice-cooling, and the resulting mixture was stirred at room temperature for one hour. The reaction solution was cooled with ice, (1S)-1-(1-naphthyl)ethyl amine (33.2 mL) (CAS registry number: 10420-89-0) was added thereto. The resulting solution was stirred at room temperature for one hour. To the reaction mixture, tert-butyl methyl ether (500 mL) was added, and the precipitate was separated by filtration. The precipitate washed with hexane/ethyl acetate (1/1). The filtrate and the washing solution were combined together, and concentrated under reduced pressure until the amount became the half. The resulting product was washed with 1 N sodium hydroxide aqueous solution (150 mL×four times), 1N hydrochloric acid (200 mL), water (150 mL), and saturated brine, sequentially, dried over anhydrous magnesium sulfate, and concentrated under reduced pressure. The resulting residue was purified by column chromatography on silica gel (hexane:ethyl acetate=90:10→80:20) to obtain a diastereomer mixture of the title compound (70 g). The diastereomer mixture was separated and purified by column chromatography on silica gel (hexane:tert-butyl methyl ether=80:20) to obtain the title compounds 15a (28 g) and 15b (33 g) having the following physical property values.

15a
TLC: Rf 0.39 (hexane:diisopropyl ether=2:1);
$^1$H-NMR (CDCl$_3$): δ 1.63, 2.07, 5.35, 5.50-5.60, 7.32-7.35, 7.42-7.58, 7.78-7.90, 8.02-8.07.

15b
TLC: Rf 0.58 (hexane:diisopropyl ether=2:1);
$^1$H-NMR (CDCl$_3$): δ 1.69, 2.17, 5.25, 5.49-5.58, 7.22-7.25, 7.43-7.58, 7.80-7.95.

Example 16

(2R)-2-(4-bromophenyl)-1,1,1-trifluoro-2-propanol

To a 1,4-dioxane solution (475 mL) of the compound (44 g) produced in Example 15a, an aqueous solution (237 mL)

of lithium hydroxide 1 hydrate (40 g) was added. The resulting solution was stirred at 55° C. for one hour. The reaction mixture was cooled to 10° C., and then 2N hydrochloric acid (520 mL) was added to the mixture so that pH was 2, followed by extraction with ethyl acetate. The organic layer was washed sequentially with a sodium hydrogencarbonate aqueous solution, water, an ammonium chloride aqueous solution, and saturated brine, then dried over anhydrous magnesium sulfate, and then concentrated under reduced pressure. The resulting residue was purified by column chromatography on silica gel (hexane:ethyl acetate=90:10→80:20) to obtain the title compound (27 g) having the following physical property values.

TLC: Rf 0.59 (hexane:ethyl acetate=4:1);
$^1$H-NMR (CDCl$_3$): δ 1.78, 2.42, 7.43-7.56.

Example 17

2-methyl-2-propanyl{4-[(2R)-1,1,1-trifluoro-2-hydroxy-2-propanyl]phenyl}carbamate A mixture of the compound (27 g) produced in Example 16, tert-butyl carbamate (15 g), palladium acetate (II) (2.2 g), 4,5-bis(diphenylphosphino)-9,9-dimethyl xanthene (8.6 g), cesium carbonate (49 g), 1,4-dioxane (200 mL) was stirred under argon atmosphere at 100° C. for two hours. The reaction mixture was cooled to room temperature, and then, water (250 mL) and ethyl acetate (250 mL) were added thereto. The resulting mixture was filtered through a Celite (product name). Water (250 mL) was added to the filtrate to separate two layers. Thereafter, the water layer was extracted with ethyl acetate. The extract layer was combined with the organic layer. It was washed sequentially with an ammonium chloride aqueous solution and saturated brine, dried over anhydrous magnesium sulfate, and concentrated under reduced pressure. The resulting residue was purified by column chromatography on silica gel (hexane:ethyl acetate=90:10→50:50) to obtain the title compound (26g) having the following physical property values.

TLC: Rf 0.31 (hexane:ethyl acetate=4:1);
$^1$H-NMR (CDCl$_3$): δ 1.52, 1.77, 2.56, 6.57, 7.37-7.40, 7.48-7.51.

Example 18

(2R)-2-(4-aminophenyl)-1,1,1-trifluoro-2-propanol

To a dichloromethane solution (170 mL) of the compound (26 g) produced in Example 17, trifluoroacetic acid (85 mL) was added. The resulting mixture was stirred at room temperature for 1.5 hours. To the reaction mixture, toluene was added, followed by concentration under reduced pressure. To the resulting residue, a saturated sodium hydrogencarbonate aqueous solution (300 mL) was added, followed by extraction with ethyl acetate. The organic layer was washed sequentially with an ammonium chloride aqueous solution and saturated brine, then dried over anhydrous magnesium sulfate, and concentrated under reduced pressure. The resulting residue was dissolved in tert-butyl methyl ether-hexane (1:1, 30 mL) at 60° C. The resulting solution was cooled to 5° C., and precipitate solids were filtered. The filtrate was concentrated to obtain the title compound (9.8 g) having the following physical property values.

TLC: Rf 0.34 (hexane:ethyl acetate=3:2);
$^1$H-NMR (CDCl$_3$): δ 1.74, 2.38, 3.77, 6.67-6.70, 7.33-7.36.

Example 19

(2R)-2-(4-aminophenyl)-1,1,1-trifluoro-2-propanol hydrochloride

A tert-butyl methyl ether solution (96 mL) of the compound (9.8 g) produced in Example 18 was cooled in ice bath, and 4 N hydrogen chloride/1,4-dioxane solution (15 mL) was added thereto. The resulting mixture was stirred. The generated precipitate was collected by filtration and washed with tert-butyl methyl ether. To the resulting solid, acetonitrile (200 mL) was added, followed by stirring at 80° C. After dissolving, the resulting solution was cooled to room temperature and was stirred overnight. The precipitated crystal was collected by filtration, and washed sequentially with acetonitrile and ethyl acetate, and then dried to obtain the title compound (7.8 g) having the following physical property values.

TLC: Rf 0.34 (hexane:ethyl acetate=3:2);
$^1$H-NMR (DMSO-d$_6$): δ 1.64, 3.57, 6.61, 7.19-7.22, 7.58-7.61.

Example 20

4-{(2R)-1,1,1-trifluoro-2-[(trimethylsilyl)oxy]-2-propanyl}aniline

The compound produced in Example 19 (7.8 g) was dissolved in methanol (10 mL) and ethyl acetate (50 mL), and a saturated sodium hydrogencarbonate aqueous solution (150 mL) was added in several portions while stirring. Then, the reaction mixture was extracted with ethyl acetate. The organic layer was washed with saturated brine, dried over anhydrous magnesium sulfate, and concentrated under reduced pressure. To the resulting residue, a tetrahydrofuran solution (130 mL) was added. The resulting mixture was cooled in ice water bath, and imidazole (11 g) and chlorotrimethylsilane (20 mL) were added thereto, followed by stirring at 30° C. for one hour. The reaction mixture was poured into water (300 mL), the water layer was separated. A saturated sodium hydrogencarbonate aqueous solution was added thereto so as to make pH at 7 or more, followed by extraction with ethyl acetate. The organic layer was washed sequentially with water and saturated brine, dried over anhydrous magnesium sulfate, and concentrated under reduced pressure to obtain the title compound (9.4 g) having the following physical property values.

TLC: Rf 0.54 (hexane:ethyl acetate=2:1);
$^1$H-NMR (CDCl$_3$): δ 0.12, 1.77, 3.69, 6.64-6.67, 7.29-7.32.

Example 21

2,6-dichloro-4-{(2R)-1,1,1-trifluoro-2-[(trimethylsilyl)oxy]-2-propanyl}aniline

To an N,N-dimethylformamide solution (100 mL) of the compound (9.4 g) produced in Example 20, N-chlorosuccinimide (9.1 g) was added. The resulting mixture was stirred at room temperature for 15 hours, and was further stirred at 40° C. for two hours. The reaction mixture was poured into water (300 mL), followed by extraction with hexane-ethyl acetate (1:1, 100 mL×three times). The organic layer was washed with saturated brine, dried over anhydrous magnesium sulfate, and concentrated under reduced pressure. The resulting residue was purified by column chromatography on silica gel (hexane:ethyl acetate=90:10→50:50) to obtain the title compound (9.0 g) having the following physical property values.

TLC: Rf 0.55 (hexane:ethyl acetate=4:1);
$^1$H-NMR (CDCl$_3$): δ 0.15, 1.75, 4.51, 7.33.

Example 22

1-{2,6-dichloro-4-[(2R)-1,1,1-trifluoro-2-hydroxy-2-propanyl]phenyl}-3-[(5-methyl-1,2-oxazole 3-yl)methyl]urea

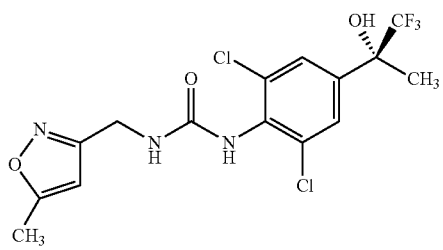 [SMILES: Cc1cc(CNC(=O)Nc2c(Cl)cc([C@@](C)(O)C(F)(F)F)cc2Cl)no1]

To a tetrahydrofuran solution (5 mL) of the compound produced in Example 21 (300 mg), N,N-diisopropyl ethyl amine (160 μL) and triphosgene (283 mg) were added. The reaction mixture was stirred at room temperature for 30 minutes, and concentrated under reduced pressure. The resulting residue was dissolved in tetrahydrofuran (5 mL), and 1-(5-methyl-1,2-oxazole-3-yl)methanamine hydrochloride (154 mg) (CAS registry number: 1050590-34-5) and triethylamine (290 μL) were added to the solution. The resulting solution was stirred at 50° C. for one hour. Water was added to the reaction mixture, followed by extraction with ethyl acetate. The organic layer was washed sequentially with water and saturated brine, dried over anhydrous sodium sulfate, and then concentrated under reduced pressure. Methanol (4 mL) and trifluoroacetic acid (1.8 mL) were added to the resulting residue, followed by stirring at room temperature for one hour. The reaction mixture was concentrated under reduced pressure, and a saturated sodium hydrogencarbonate aqueous solution was added thereto, followed by extraction with ethyl acetate. The organic layer was washed sequentially with water and saturated brine, dried over anhydrous sodium sulfate, and then concentrated under reduced pressure. The resulting residue was purified by column chromatography on silica gel (hexane:ethyl acetate=90:10→70/30→50:50) to obtain the title compound (310 mg) having the following physical property values.

TLC: Rf 0.27 (hexane:ethyl acetate=1:1);
$^1$H-NMR (DMSO-d$_6$): δ 1.69, 2.37, 4.26, 6.10, 6.90-6.97, 7.64, 8.24.

Examples 22(1) to (17)

Amine produced in Example 10 or the corresponding amine instead of 1-(5-methyl-1,2-oxazole-3-yl)methanamine hydrochloride was used and subjected to the same procedure as in Example 22 to obtain the title compound having the following physical property values.

Example 22(1)

1-{2,6-dichloro-4-[(2R)-1,1,1-trifluoro-2-hydroxy-2-propanyl]phenyl}-3-{[5-(trifluoromethyl)-2-pyridinyl]methyl}urea

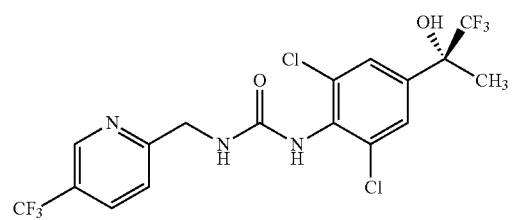 [SMILES: C[C@@](O)(c1cc(Cl)c(NC(=O)NCc2ccc(C(F)(F)F)cn2)c(Cl)c1)C(F)(F)F]

TLC: Rf 0.16 (hexane:ethyl acetate=1:1);
$^1$H-NMR (CDCl$_3$): δ 1.75, 2.77, 4.65, 5.76, 6.60, 7.49, 7.61, 7.91-7.95, 8.78.

Example 22(2)

1-{2,6-dichloro-4-[(2R)-1,1,1-trifluoro-2-hydroxy-2-propanyl]phenyl}-3-{[5-(trifluoromethyl)-2-pyrimidinyl]methyl}urea

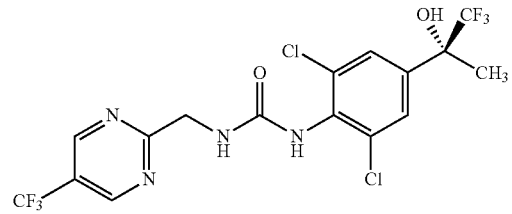 [SMILES: C[C@@](O)(c1cc(Cl)c(NC(=O)NCc2ncc(C(F)(F)F)cn2)c(Cl)c1)C(F)(F)F]

TLC: Rf 0.34 (hexane:ethyl acetate=1:1);
$^1$H-NMR (DMSO-d$_6$): δ 1.69, 4.61, 6.92, 7.08, 7.62, 8.46, 9.25.

Example 22(3)

1-{2,6-dichloro-4-[(2R)-1,1,1-trifluoro-2-hydroxy-2-propanyl]phenyl}-3-{[6-(trifluoromethyl)-3-pyridinyl]methyl}urea

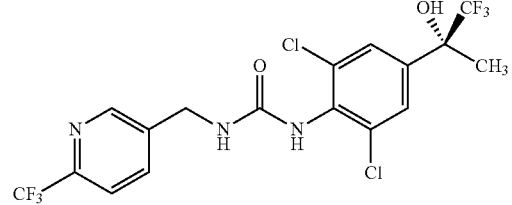 [SMILES: C[C@@](O)(c1cc(Cl)c(NC(=O)NCc2ccc(C(F)(F)F)nc2)c(Cl)c1)C(F)(F)F]

TLC: Rf 0.31 (hexane:ethyl acetate=1:1);
$^1$H-NMR (DMSO-d$_6$): δ 1.69, 4.40, 6.93, 7.08, 7.64, 7.87-7.99, 8.35, 8.68.

Example 22(4)

1-{2,6-dichloro-4-[(2R)-1,1,1-trifluoro-2-hydroxy-2-propanyl]phenyl}-3-{[2-(trifluoromethyl)-5-pyrimidinyl]methyl}urea TLC: Rf 0.23 (hexane:ethyl acetate=1:1);
$^1$H-NMR (DMSO-$d_6$): δ 1.69, 4.42, 6.94, 7.12, 7.64, 8.46, 8.95.

Example 22(5)

1-[(5-chloro-2-pyridinyl)methyl]-3-{2,6-dichloro-4-[(2R)-1,1,1-trifluoro-2-hydroxy-2-propanyl]phenyl}urea

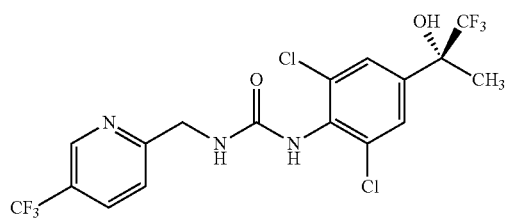 [SMILES: C[C@@](O)(c1cc(Cl)c(NC(=O)NCc2ccc(C(F)(F)F)cn2)c(Cl)c1)C(F)(F)F]

TLC: Rf 0.20 (hexane:ethyl acetate=1:1);
$^1$H-NMR (DMSO-$d_6$): δ 1.69, 4.36, 6.93, 7.06, 7.39, 7.64, 7.94, 8.37, 8.55.

Example 22(6)

1-{2,6-dichloro-4-[(2R)-1,1,1-trifluoro-2-hydroxy-2-propanyl]phenyl}-3-{[6-(2,2,2-trifluoro ethoxy)-3-pyridinyl]methyl}urea TLC: Rf 0.38 (hexane:ethyl acetate=1:1);
$^1$H-NMR (DMSO-$d_6$): δ 1.70, 4.25, 4.93-5.02, 6.93-6.98, 7.64, 7.74, 8.11, 8.19.

Example 22(7)

1-{2,6-dichloro-4-[(2R)-1,1,1-trifluoro-2-hydroxy-2-propanyl]phenyl}-3-[4-(trifluoromethyl)benzyl]urea TLC: Rf 0.60 (hexane:ethyl acetate=1:1);
$^1$H-NMR (DMSO-$d_6$): δ 1.70, 4.38, 6.94, 7.02, 7.50-7.53, 7.65, 7.69-7.72, 8.26.

Example 22(8)

1-benzyl-3-{2,6-dichloro-4-[(2R)-1,1,1-trifluoro-2-hydroxy-2-propanyl]phenyl}urea LC retention time (min), LC condition 3: 0.90;
$^1$H-NMR (DMSO-$d_6$): δ 1.70, 4.29, 6.89, 6.95, 7.20-7.35, 7.64, 8.14.

Example 22(9)

1-{2,6-dichloro-4-[(2R)-1,1,1-trifluoro-2-hydroxy-2-propanyl]phenyl}-3-(4-methoxybenzyl)urea LC retention time (min), LC condition 3: 0.90;
$^1$H-NMR (DMSO-$d_6$): δ 1.69, 3.72, 4.21, 6.79, 6.87-6.92, 7.20-7.23, 7.63, 8.07.

Example 22(10)

1-{2,6-dichloro-4-[(2R)-1,1,1-trifluoro-2-hydroxy-2-propanyl]phenyl}-3-(4-methyl benzyl)urea LC retention time (min), LC condition 3: 0.95;
$^1$H-NMR (DMSO-$d_6$): δ 1.70, 2.27, 4.24, 6.82, 6.94, 7.14-7.20, 7.64, 8.10.

Example 22(11)

1-{2,6-dichloro-4-[(2R)-1,1,1-trifluoro-2-hydroxy-2-propanyl]phenyl}-3-[4-(2-methyl-2-propanyl)benzyl]urea LC retention time (min), LC condition 3: 1.05;
$^1$H-NMR (DMSO-$d_6$): δ 1.27, 1.70, 4.25, 6.84, 6.92, 7.21-7.24, 7.34-7.36, 7.64, 8.09.

Example 22(12)

1-{2,6-dichloro-4-[(2R)-1,1,1-trifluoro-2-hydroxy-2-propanyl]phenyl}-3-(4-phenoxybenzyl)urea LC retention time (min), LC condition 3: 1.03;
$^1$H-NMR (DMSO-$d_6$): δ 1.70, 4.28, 6.87-6.91, 6.96-7.00, 7.09-7.15, 7.31-7.41, 7.64, 8.14.

Example 22(13)

1-{2,6-dichloro-4-[(2R)-1,1,1-trifluoro-2-hydroxy-2-propanyl]phenyl}-3-[4-(difluoromethoxy)benzyl]urea LC retention time (min), LC condition 3: 0.94;
$^1$H-NMR (DMSO-$d_6$): δ 1.70, 4.28, 6.88-6.94, 7.13-7.16, 7.20, 7.33-7.36, 7.64, 8.16.

Example 22(14)

1-{2,6-dichloro-4-[(2R)-1,1,1-trifluoro-2-hydroxy-2-propanyl]phenyl}-3-[4-(4-morpholinyl)benzyl]urea LC retention time (min), LC condition 3: 0.73;
$^1$H-NMR (DMSO-$d_6$): δ 1.70, 3.07-3.11, 3.72-3.75, 4.19, 6.77, 6.92-6.95, 7.17-7.20, 7.64, 8.07.

Example 22(15)

1-(4-cyanobenzyl)-3-{2,6-dichloro-4-[(2R)-1,1,1-trifluoro-2-hydroxy-2-propanyl]phenyl}urea LC retention time (min), LC condition 3: 0.87;
$^1$H-NMR (DMSO-$d_6$): δ 1.70, 4.37, 6.93, 7.02, 7.47-7.50, 7.65, 7.80-7.82, 8.28.

Example 22(16)

1-{2,6-dichloro-4-[(2R)-1,1,1-trifluoro-2-hydroxy-2-propanyl]phenyl}-3-[4-(4-fluorophenoxyl)benzyl]urea LC retention time (min), LC condition 3: 1.03;
$^1$H-NMR (DMSO-$d_6$): δ 1.70, 4.27, 6.86-7.05, 7.19-7.23, 7.30-7.33, 7.64, 8.13.

Example 22(17)

1-{2,6-dichloro-4-[(2R)-1,1,1-trifluoro-2-hydroxy-2-propanyl]phenyl}-3-{[2-(trifluoromethyl)-1,3-thiazole-5-yl]methyl}urea TLC: Rf 0.50 (hexane:ethyl acetate=1:1);
$^1$H-NMR (DMSO-$d_6$): δ 1.71, 4.55, 6.95, 7.20, 7.66, 7.98, 8.41.

Example 23

1-{2,6-dichloro-4-[(2R)-1,1,1-trifluoro-2-hydroxy-2-propanyl]phenyl}-3-{[3-(trifluoromethyl)-1,2,4-oxadiazole-5-yl]methyl}urea

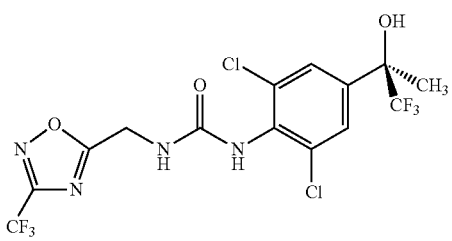 [SMILES: C[C@@](O)(c1cc(Cl)c(NC(=O)NCc2nc(C(F)(F)F)no2)c(Cl)c1)C(F)(F)F]

To a tetrahydrofuran solution (6 mL) of the compound produced in Example 21 (300 mg), N,N-diisopropyl ethyl amine (165 μL) and triphosgene (283 mg) were added. The reaction mixture was stirred at room temperature for one hour, and then concentrated under reduced pressure. The resulting residue was dissolved in tetrahydrofuran (6 mL), 1-[3-(trifluoromethyl)-1,2,4-oxadiazole-5-yl]methanamine hydrochloride (264 mg) (CAS registry number: 944905-93-5) and N,N-diisopropyl ethyl amine (750 μL) were added. The reaction mixture was stirred at 45° C. for 17 hours. Then, tetrabutyl ammonium fluoride (1 M tetrahydrofuran solution, 1 mL) was added, and the mixture was stirred at room temperature for one hour. A saturated ammonium chloride aqueous solution was added to the reaction mixture, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=60:40) to obtain the title compound (380 mg) having the following physical property values.
TLC: Rf 0.50 (hexane:ethyl acetate=1:1);
$^1$H-NMR (DMSO-$d_6$): δ 1.68, 4.68, 6.93, 7.24, 7.63, 8.61.

Example 24

2,6-dichloro-4-{(2S)-1,1,1-trifluoro-2-[(trimethylsilyl)oxy]-2-propanyl}aniline

The compound produced in Example 15b instead of the compound produced in Example 15a was used and subjected to the same procedure as in Example 16→Example 17→Example 18→Example 19→Example 20→Example 21 to obtain the title compound having the following physical property values.
TLC: Rf 0.56 (hexane:ethyl acetate=4:1);
$^1$H-NMR (CDCl$_3$): δ 0.15, 1.75, 4.51, 7.33.

Example 25

1-{2,6-dichloro-4-[(2S)-1,1,1-trifluoro-2-hydroxy-2-propanyl]phenyl}-3-[(5-methyl-1,2-oxazole-3-yl)methyl]urea

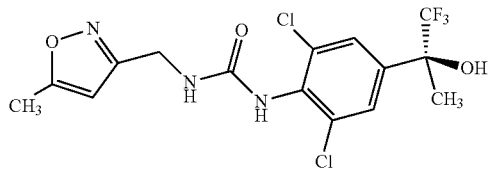 [SMILES: Cc1cc(CNC(=O)Nc2c(Cl)cc([C@](C)(O)C(F)(F)F)cc2Cl)no1]

The compound produced in Example 24 instead of the compound produced in Example 21 was used and subjected to the same procedure as in Example 22 to obtain the title compound having the following physical property values.
TLC: Rf 0.30 (hexane:ethyl acetate=1:1);
$^1$H-NMR (DMSO-$d_6$): δ 1.69, 2.37, 4.25, 6.10, 6.91-7.00, 7.64, 8.24.

Examples 25(1) to (8)

The compound produced in Example 24 instead of the compound produced in Example 21, and amine produced in Example 10 or the corresponding amine instead of 1-(5-methyl-1,2-oxazole-3-yl)methanamine hydrochloride were used and subjected to the same procedure as in Example 22 to obtain the title compound having the following physical property values.

Example 25(1)

1-{2,6-dichloro-4-[(2S)-1,1,1-trifluoro-2-hydroxy-2-propanyl]phenyl}-3-{[5-(trifluoromethyl)-2-pyrimidinyl]methyl}urea

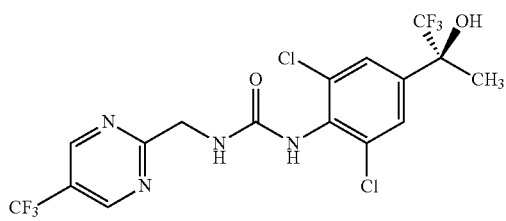 [SMILES: C[C@](O)(c1cc(Cl)c(NC(=O)NCc2ncc(C(F)(F)F)cn2)c(Cl)c1)C(F)(F)F]

TLC: Rf 0.34 (hexane:ethyl acetate=1:1);
$^1$H-NMR (DMSO-$d_6$): δ 1.69, 4.60, 6.92, 7.08, 7.62, 8.46, 9.25.

Example 25(2)

1-{2,6-dichloro-4-[(2S)-1,1,1-trifluoro-2-hydroxy-2-propanyl]phenyl}-3-{[6-(trifluoromethyl)-3-pyridinyl]methyl}urea

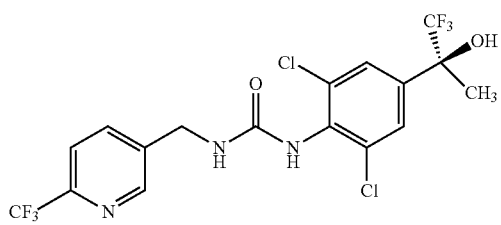 [SMILES: C[C@](O)(c1cc(Cl)c(NC(=O)NCc2ccc(C(F)(F)F)nc2)c(Cl)c1)C(F)(F)F]

TLC: Rf 0.29 (hexane:ethyl acetate=1:1);
$^1$H-NMR (DMSO-$d_6$): δ 1.69, 4.40, 6.93, 7.08, 7.64, 7.89, 7.97, 8.35, 8.67.

Example 25(3)

1-{2,6-dichloro-4-[(2S)-1,1,1-trifluoro-2-hydroxy-2-propanyl]phenyl}-3-{[2-(trifluoromethyl)-5-pyrimidinyl]methyl}urea TLC: Rf 0.21 (hexane:ethyl acetate=1:1);
$^1$H-NMR (DMSO-$d_6$): δ 1.69, 4.41, 6.93, 7.12, 7.65, 8.46, 8.95.

Example 25(4)

1-{2,6-dichloro-4-[(2S)-1,1,1-trifluoro-2-hydroxy-2-propanyl]phenyl}-3-{[5-(trifluoromethyl)-2-pyridinyl]methyl}urea TLC: Rf 0.16 (hexane:ethyl acetate=1:1);
$^1$H-NMR (CDCl$_3$): δ 1.76, 2.67, 4.65, 5.73, 6.60, 7.49, 7.61, 7.91-7.95, 8.79.

Example 25(5)

1-[(5-chloro-2-pyridinyl)methyl]-3-{2,6-dichloro-4-[(2S)-1,1,1-trifluoro-2-hydroxy-2-propanyl]phenyl}urea

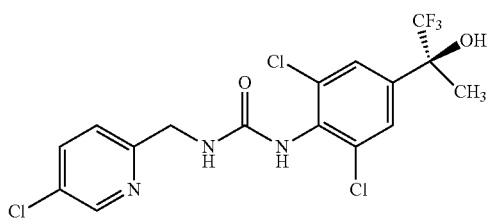 [SMILES: C[C@](O)(c1cc(Cl)c(NC(=O)NCc2ccc(Cl)cn2)c(Cl)c1)C(F)(F)F]

TLC: Rf 0.24 (hexane:ethyl acetate=1:1);
$^1$H-NMR (DMSO-$d_6$): δ 1.69, 4.36, 6.93, 7.06, 7.38, 7.64, 7.94, 8.37, 8.55.

Example 25(6)

1-{2,6-dichloro-4-[(2S)-1,1,1-trifluoro-2-hydroxy-2-propanyl]phenyl}-3-{[6-(2,2,2-trifluoro ethoxy)-3-pyridinyl]methyl}urea TLC: Rf 0.37 (hexane:ethyl acetate=1:1);
$^1$H-NMR (DMSO-$d_6$): δ 1.70, 4.25, 4.93-5.02, 6.93-6.98, 7.64, 7.74, 8.11, 8.19.

Example 25(7)

1-{2,6-dichloro-4-[(2S)-1,1,1-trifluoro-2-hydroxy-2-propanyl]phenyl}-3-[4-(trifluoromethyl)benzyl]urea TLC: Rf 0.60 (hexane:ethyl acetate=1:1);
$^1$H-NMR (DMSO-$d_6$): δ 1.70, 4.38, 6.93, 7.02, 7.50-7.53, 7.65, 7.69-7.72, 8.25.

Example 25(8)

1-{2,6-dichloro-4-[(2S)-1,1,1-trifluoro-2-hydroxy-2-propanyl]phenyl}-3-{[2-(trifluoromethyl)-1,3-thiazole-5-yl]methyl}urea TLC: Rf 0.50 (hexane:ethyl acetate=1:1);
$^1$H-NMR (DMSO-$d_6$): δ 1.71, 4.55, 6.95, 7.19, 7.66, 7.98, 8.40.

Example 26

1-{2,6-dichloro-4-[(2S)-1,1,1-trifluoro-2-hydroxy-2-propanyl]phenyl}-3-{[3-(trifluoromethyl)-1,2,4-oxadiazole-5-yl]methyl}urea

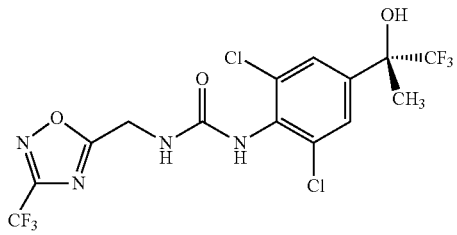 [SMILES: C[C@](O)(c1cc(Cl)c(NC(=O)NCc2nc(C(F)(F)F)no2)c(Cl)c1)C(F)(F)F]

The compound produced in Example 24 instead of the compound produced in Example 21 was used and subjected to the same procedure as in Example 23 to obtain the title compound having the following physical property values.
TLC: Rf 0.50 (hexane:ethyl acetate=1:1);
$^1$H-NMR (DMSO-$d_6$): δ 1.68, 4.68, 6.92, 7.24, 7.63, 8.60.

Examples 27a and 27b (1R)-1-(4-bromophenyl)-2,2,2-trifluoro ethyl[(1S)-1-(1-naphthyl)ethyl]carbamate (27a) and (1S)-1-(4-bromophenyl)-2,2,2-trifluoroethyl[(1S)-1-(1-naphthyl)ethyl]carbamate (27b)

To a dichloromethane solution (80 mL) of 1-(4-bromophenyl)-2,2,2-trifluoroethanol (4.0 g) (CAS registry number: 76911-73-4), 4-dimethyl amino pyridine (2.3 g) and 4-nitrophenyl chloroformate (3.3 mL) were added under ice-cooling. The resulting mixture was stirred at room temperature for one hour. The reaction solution was cooled again in ice, (1S)-1-(1-naphthyl)ethanamine (4 mL) (CAS registry number: 10420-89-0) was added thereto, followed by stirring at room temperature for 30 minutes. The reaction solution was filtered, and the filtrate was washed sequentially with 1 N sodium hydroxide aqueous solution twice, with 1 N hydrochloric acid once, and with saturated brine once. The organic layer was dried over anhydrous magnesium sulfate, and concentrated under reduced pressure. The resulting residue was purified by column chromatography on silica gel (hexane:tert-butyl methyl ether=90:10) to obtain the title compounds 27a (1.91 g) and 27b (2.44 g) having the following physical property values.
27a
TLC: Rf 0.57 (hexane:tert-butyl methyl ether=3:1);
$^1$H-NMR (CDCl$_3$): δ 1.65, 5.30, 5.64, 6.04, 7.34, 7.47-7.57, 7.82, 7.89, 8.07.

27b

TLC: Rf 0.69 (hexane:tert-butyl methyl ether=3:1);
¹H-NMR (CDCl₃): δ 1.72, 5.29, 5.60, 6.03, 7.28, 7.41-7.51, 7.80, 7.86, 7.94.

Example 28

(1R)-1-(4-bromophenyl)-2,2,2-trifluoroethanol

To a mix solution of 1,4-dioxane (40 mL) and water (20 mL) of the compound produced in Example 27a (2.37 g), lithium hydroxide 1 hydrate (2.20 g) was added, and the resulting mixture was stirred at 50° C. for one hour. To the reaction mixture, 2 N hydrochloric acid (40 mL) was added in an ice bath, followed by extraction with ethyl acetate. The organic layer was dried over anhydrous magnesium sulfate, and then concentrated under reduced pressure. The resulting residue was purified by column chromatography on silica gel (hexane:ethyl acetate=90:10) to obtain the title compound (1.34 g) having the following physical property values.
TLC: Rf 0.65 (hexane:ethyl acetate=3:1);
¹H-NMR (CDCl₃): δ 2.57, 4.97-5.05, 7.35-7.38, 7.54-7.57.

Example 29

2-methyl-2-propanyl{4-[(1R)-2,2,2-trifluoro-1-hydroxyethyl]phenyl}carbamate

To a 1,4-dioxane solution (30 mL) of the compound produced in Example 28 (1.34 g), tert-butyl carbamate (800 mg), palladium acetate (II) (118 mg), 4,5-bis(diphenylphosphino)-9,9-dimethyl xanthene (456 mg), and cesium carbonate (2.57 g) were added. The resulting mixture was heated and refluxed for three hours. The reaction mixture was filtered through a Celite (product name), and the filtrate was concentrated under reduced pressure. The resulting residue was purified by column chromatography on silica gel (hexane:ethyl acetate=80:20) to obtain the title compound (1.32 g) having the following physical property values.
TLC: Rf 0.48 (hexane:ethyl acetate=3:1);
¹H-NMR (CDCl₃): δ 1.52, 2.58, 4.98, 6.56, 7.40.

Example 30

(1R)-1-(4-amino-3,5-dichlorophenyl)-2,2,2-trifluoroethanol

To a dichloromethane solution (20 mL) of the compound produced in Example 29 (1.32 g), trifluoroacetic acid (10 mL) was added in an ice bath. The resulting mixture was stirred at room temperature for one hour. Toluene (10 mL) was added to the reaction mixture, followed by concentration under reduced pressure. A saturated sodium hydrogencarbonate aqueous solution was added to the resulting residue, followed by extraction with ethyl acetate. The organic layer was dried over anhydrous magnesium sulfate, and then concentrated under reduced pressure. The resulting residue was dissolved in N,N-dimethylformamide (10 mL), and N-chlorosuccinimide (684 mg) to the resulting solution. The reaction mixture was stirred at 40° C. for 18 hours. Water was added to the reaction mixture, followed by extraction with a mixed solvent of ethyl acetate and hexane. The organic layer was dried over anhydrous magnesium sulfate, and then concentrated under reduced pressure. The resulting residue was purified by column chromatography on silica gel (hexane:ethyl acetate=85:15) to obtain the title compound (310 mg) having the following physical property values.
TLC: Rf 0.50 (hexane:ethyl acetate=3:1);
¹H-NMR (CDCl₃): δ 4.58, 4.83-4.91, 7.31.

Example 31

2,6-dichloro-4-{(1R)-2,2,2-trifluoro-1-[(trimethylsilyl)oxy]ethyl}aniline

To a tetrahydrofuran solution (10 mL) of the compound produced in Example 30 (310 mg), chlorotrimethylsilane (583 µL) and imidazole (405 mg) were added. The resulting mixture was stirred at room temperature for three hours. A saturated ammonium chloride aqueous solution was added to the reaction mixture, followed by extraction with ethyl acetate. The organic layer was dried over anhydrous magnesium sulfate, and concentrated under reduced pressure. The resulting residue was purified by column chromatography on silica gel (hexane:ethyl acetate=95:5) to obtain the title compound (396 mg) having the following physical property values.
TLC: Rf 0.75 (hexane:ethyl acetate=5:1);
¹H-NMR (CDCl₃): δ 0.13, 4.56, 4.75, 7.26.

Example 32

1-{2,6-dichloro-4-[(1R)-2,2,2-trifluoro-1-hydroxyethyl]phenyl}-3-{[5-(trifluoromethyl)-2-pyridinyl]methyl}urea

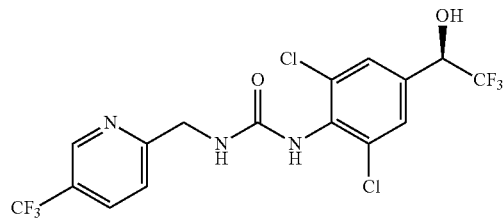 [SMILES: O=C(NCc1ccc(C(F)(F)F)cn1)Nc1c(Cl)cc([C@@H](O)C(F)(F)F)cc1Cl]

To a tetrahydrofuran solution (4 mL) of the compound produced in Example 31 (80 mg), N,N-diisopropyl amine (49 µL) and triphosgene (78 mg) were added. The reaction mixture was stirred at room temperature for two hours, and then concentrated under reduced pressure. The resulting residue was dissolved in tetrahydrofuran (4 mL), and 1-[5-(trifluoromethyl)-2-pyridinyl]methanamine hydrochloride (76 mg) and N,N-diisopropyl ethyl amine (83 µL) were added thereto. The reaction mixture was stirred at 50° C. for two hours, and then a saturated sodium hydrogencarbonate aqueous solution was added thereto, followed by extraction with ethyl acetate. The organic layer was washed sequentially with water and saturated brine, and then dried over anhydrous sodium sulfate, followed by concentration under reduced pressure. The resulting residue was purified by column chromatography on silica gel (hexane:ethyl acetate=100:0→90/10→50/50) to obtain the title compound (67 mg) having the following physical property values.
TLC: Rf 0.21 (hexane:ethyl acetate=1:1);
¹H-NMR (CD₃OD): δ 4.58, 5.07, 7.57, 7.64, 8.11, 8.80.

Examples 32 (1) to (7)

The corresponding amine instead of 1-[5-(trifluoromethyl)-2-pyridinyl]methanamine hydrochloride was used and subjected to the same procedure as in Example 32 to obtain the title compound having the following physical property values.

Example 32(1)

1-{2,6-dichloro-4-[(1R)-2,2,2-trifluoro-1-hydroxyethyl]phenyl}-3-{[3-(trifluoromethyl)-1,2,4-oxadiazole-5-yl]methyl}urea

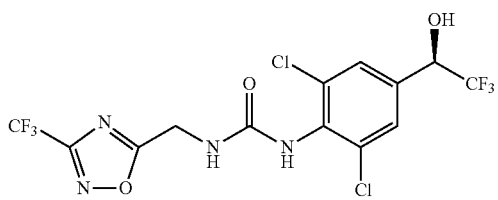 [SMILES: O=C(NCc1nc(C(F)(F)F)no1)Nc1c(Cl)cc([C@@H](O)C(F)(F)F)cc1Cl]

TLC: Rf 0.38 (hexane:ethyl acetate=1:2);
$^1$H-NMR (DMSO-$d_6$): δ 4.68, 5.27, 7.13, 7.25, 7.57, 8.62.

Example 32(2)

1-{2,6-dichloro-4-[(1R)-2,2,2-trifluoro-1-hydroxyethyl]phenyl}-3-[(5-methyl-1,2-oxazole-3-yl)methyl]urea TLC: Rf 0.23 (hexane:ethyl acetate=1:2);
$^1$H-NMR (DMSO-$d_6$): δ 2.36, 4.24, 5.27, 6.09, 6.95, 7.17, 7.57, 8.27.

Example 32(3)

1-{2,6-dichloro-4-[(1R)-2,2,2-trifluoro-1-hydroxyethyl]phenyl}-3-{[2-(trifluoromethyl)-5-pyrimidinyl]methyl}urea

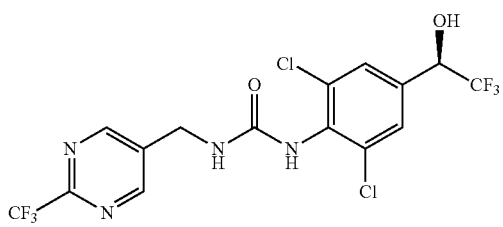 [SMILES: O=C(NCc1cnc(C(F)(F)F)nc1)Nc1c(Cl)cc([C@@H](O)C(F)(F)F)cc1Cl]

TLC: Rf 0.35 (hexane:ethyl acetate=1:2);
$^1$H-NMR (DMSO-$d_6$): δ 4.41, 5.27, 7.10-7.14, 7.58, 8.47, 8.94.

Example 32(4)

1-{2,6-dichloro-4-[(1R)-2,2,2-trifluoro-1-hydroxyethyl]phenyl}-3-{[5-(trifluoromethyl)-2-pyrimidinyl]methyl}urea

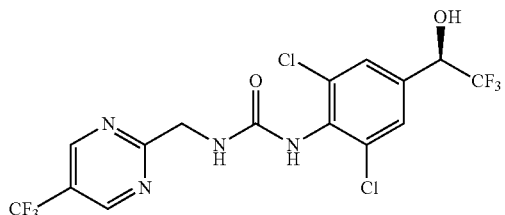

TLC: Rf 0.27 (hexane:ethyl acetate=1:1);
$^1$H-NMR (CD$_3$OD): δ 4.72, 5.06, 7.55, 9.08.

Example 32(5)

1-{2,6-dichloro-4-[(1R)-2,2,2-trifluoro-1-hydroxyethyl]phenyl}-3-{[6-(trifluoromethyl)-3-pyridinyl]methyl}urea TLC: Rf 0.29 (hexane:ethyl acetate=1:1);
$^1$H-NMR (CD$_3$OD): δ 4.51, 5.08, 7.57, 7.78, 8.00, 8.69.

Example 32(6)

1-{2,6-dichloro-4-[(1R)-2,2,2-trifluoro-1-hydroxyethyl]phenyl}-3-{[6-(2,2,2-trifluoroethoxy)-3-pyridinyl]methyl}urea TLC: Rf 0.36 (hexane:ethyl acetate=1:1);
$^1$H-NMR (DMSO-$d_6$): δ 4.24, 4.92-5.01, 5.27, 6.92-6.97, 7.11, 7.58, 7.73, 8.10, 8.19.

Example 32(7)

1-{2,6-dichloro-4-[(1R)-2,2,2-trifluoro-1-hydroxyethyl]phenyl}-3-[4-(trifluoromethyl)benzyl]urea TLC: Rf 0.55 (hexane:ethyl acetate=1:1);
$^1$H-NMR (DMSO-$d_6$): δ 4.38, 5.24-5.33, 7.02, 7.13, 7.50-7.53, 7.59, 7.69-7.72, 8.27.

Example 33

1-{2,6-dichloro-4-[(1R)-2,2,2-trifluoro-1-hydroxyethyl]phenyl}-3-{[2-(trifluoromethyl)-1,3-thiazole-5-yl]methyl}urea

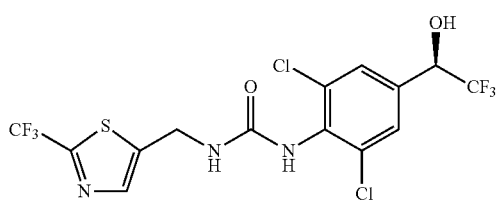 [SMILES: O=C(NCc1cnc(C(F)(F)F)s1)Nc1c(Cl)cc([C@@H](O)C(F)(F)F)cc1Cl]

The compound produced in Example 10 instead of 1-[5-(trifluoromethyl)-2-pyridinyl]methanamine hydrochloride was used and subjected to the same procedure as in Example 32 to obtain the title compound having the following physical property values.
TLC: Rf 0.33 (hexane:ethyl acetate=1:1);
$^1$H-NMR (DMSO-$d_6$): δ 4.53, 5.27, 7.12, 7.18, 7.58, 7.95, 8.40.

Example 34

2,6-dichloro-4-{(1S)-2,2,2-trifluoro-1-[(trimethylsilyl)oxy]ethyl}aniline

The compound produced in Example 27b instead of the compound produced in Example 27a was used and subjected to the same procedure as in Example 28→Example 29→Example 30→Example 31 to obtain the title compound having the following physical property values.
TLC: Rf 0.75 (hexane:ethyl acetate=5:1);
$^1$H-NMR (CDCl$_3$): δ 0.13, 4.56, 4.75, 7.26.

Example 35

1-{2,6-dichloro-4-[(1S)-2,2,2-trifluoro-1-hydroxyethyl]phenyl}-3-{[5-(trifluoromethyl)-2-pyridinyl]methyl}urea

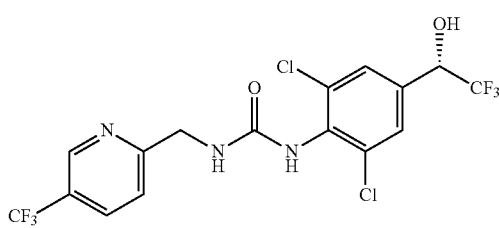

The compound produced in Example 34 instead of the compound produced in Example 31 was used and subjected to the same procedure as in Example 32 to obtain the title compound having the following physical property values.
TLC: Rf 0.31 (hexane:ethyl acetate=1:1);
$^1$H-NMR (CD$_3$OD): δ 4.58, 5.08, 7.57, 7.64, 8.11, 8.80.

Examples 35(1) to (7)

The compound produced in Example 34 instead of the compound produced in Example 31, and the corresponding amine instead of 1-[5-(trifluoromethyl)-2-pyridinyl]methanamine hydrochloride were used and subjected to the same procedure as in Example 32 to obtain the title compound having the following physical property values.

Example 35(1)

1-{2,6-dichloro-4-[(1S)-2,2,2-trifluoro-1-hydroxyethyl]phenyl}-3-{[3-(trifluoromethyl)-1,2,4-oxadiazole-5-yl]methyl}urea

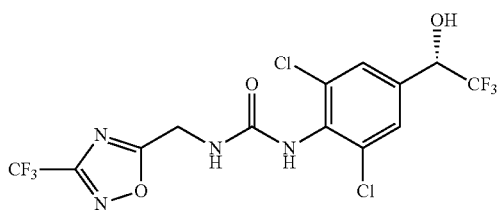 [SMILES: O=C(NCc1nc(C(F)(F)F)no1)Nc1c(Cl)cc([C@H](O)C(F)(F)F)cc1Cl]

TLC: Rf 0.38 (hexane:ethyl acetate=1:2);
$^1$H-NMR (DMSO-$d_6$): δ 4.68, 5.28, 7.14, 7.26, 7.58, 8.63.

Example 35(2)

1-{2,6-dichloro-4-[(1S)-2,2,2-trifluoro-1-hydroxyethyl]phenyl}-3-[(5-methyl-1,2-oxazole-3-yl)methyl]urea TLC: Rf 0.23 (hexane:ethyl acetate=1:2);
$^1$H-NMR (DMSO-$d_6$): δ 2.36, 4.24, 5.27, 6.09, 6.95, 7.17, 7.57, 8.27.

Example 35(3)

1-{2,6-dichloro-4-[(1S)-2,2,2-trifluoro-1-hydroxyethyl]phenyl}-3-{[2-(trifluoromethyl)-5-pyrimidinyl]methyl}urea

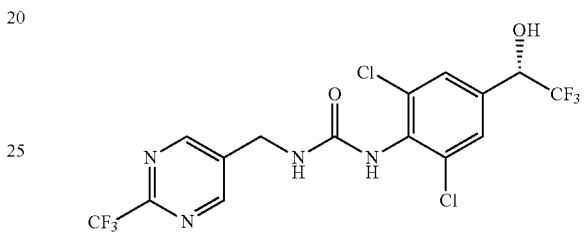

TLC: Rf 0.35 (hexane:ethyl acetate=1:2);
$^1$H-NMR (DMSO-$d_6$): δ 4.41, 5.27, 7.10-7.14, 7.58, 8.47, 8.94.

Example 35(4)

1-{2,6-dichloro-4-[(1S)-2,2,2-trifluoro-1-hydroxyethyl]phenyl}-3-{[5-(trifluoromethyl)-2-pyrimidinyl]methyl}urea TLC: Rf 0.48 (hexane:ethyl acetate=3:2);
$^1$H-NMR (CD$_3$OD): δ 4.72, 5.07, 7.56, 9.09.

Example 35(5)

1-{2,6-dichloro-4-[(1S)-2,2,2-trifluoro-1-hydroxyethyl]phenyl}-3-{[6-(trifluoromethyl)-3-pyridinyl]methyl}urea TLC: Rf 0.29 (hexane:ethyl acetate=1:1);
$^1$H-NMR (CD$_3$OD): δ 4.51, 5.08, 7.57, 7.79, 8.00, 8.69.

Example 35(6)

1-{2,6-dichloro-4-[(1S)-2,2,2-trifluoro-1-hydroxyethyl]phenyl}-3-{[6-(2,2,2-trifluoroethoxy)-3-pyridinyl]methyl}urea TLC: Rf 0.38 (hexane:ethyl acetate=1:1);
$^1$H-NMR (DMSO-$d_6$): δ 4.24, 4.92-5.01, 5.27, 6.90-6.97, 7.11, 7.58, 7.73, 8.10, 8.20.

Example 35(7)

1-{2,6-dichloro-4-[(1S)-2,2,2-trifluoro-1-hydroxyethyl]phenyl}-3-[4-(trifluoromethyl)benzyl]urea TLC: Rf 0.55 (hexane:ethyl acetate=1:1);
$^1$H-NMR (DMSO-$d_6$): δ 4.38, 5.24-5.31, 7.02, 7.13, 7.50-7.53, 7.59, 7.69-7.72, 8.27.

Example 36

1-{2,6-dichloro-4-[(1S)-2,2,2-trifluoro-1-hydroxy-ethyl]phenyl}-3-{[2-(trifluoromethyl)-1,3-thiazole-5-yl]methyl}urea

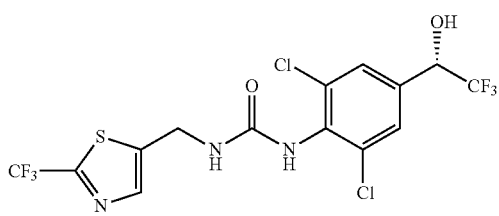 [SMILES: O=C(NCc1cnc(C(F)(F)F)s1)Nc1c(Cl)cc([C@H](O)C(F)(F)F)cc1Cl]

The compound produced in Example 10 instead of 1-[5-(trifluoromethyl)-2-pyridinyl]methanamine hydrochloride was used and subjected to the same procedure as in Example 32 to obtain the title compound having the following physical property values.

TLC: Rf 0.33 (hexane:ethyl acetate=1:1);
$^1$H-NMR (DMSO-d$_6$): δ 4.53, 5.27, 7.12, 7.18, 7.58, 7.96, 8.39.

Example 37

4-acetyl-3-fluorophenyl trifluoromethane sulfonate 1-(2-fluoro-4-hydroxyphenyl)ethanone (2.05 g) (CAS registry number: 68301-59-7) was suspended in dichloromethane (20 mL), and triethylamine (2.04 mL) and trifluoromethane sulfonic acid anhydride (2.46 mL) were added thereto under ice-cooling. The reaction mixture was stirred at room temperature for 30 minutes, followed by concentration under reduced pressure. The resulting residue was purified by column chromatography on silica gel (hexane:ethyl acetate=100:0→90/10→70/30) to obtain the title compound (3.90 g) having the following physical property values.

TLC: Rf 0.69 (hexane:ethyl acetate=3:1);
$^1$H-NMR (CDCl$_3$): δ 2.67, 7.13-7.21, 8.02.

Example 38

3-fluoro-4-(1,1,1-trifluoro-2-hydroxy-2-propanyl)phenyl trifluoromethane sulfonate To a tetrahydrofuran solution (13.6 mL) of the compound produced in Example 37 (3.90 g), (trifluoromethyl)trimethylsilane (3.88 g) and tetrabutyl ammonium fluoride (1 M tetrahydrofuran solution, 40 µL) were added. The reaction mixture was stirred at room temperature for 14 hours, and then (trifluoromethyl)trimethylsilane (2.9 g) was added, followed by stirring at room temperature for six hours. The reaction mixture was cooled in ice, and then tetrabutyl ammonium fluoride (1 M tetrahydrofuran solution, 7 mL) was added to the reaction mixture, followed by stirring at room temperature for five minutes. To the reaction mixture, 1N hydrochloric acid was added, followed by extraction with ethyl acetate. The organic layer was dried over anhydrous sodium sulfate, and then concentrated under reduced pressure. The resulting residue was purified by column chromatography on silica gel (hexane:ethyl acetate=90/10→60/40) to obtain the title compound (2.06 g) having the following physical property values.

TLC: Rf 0.26 (hexane:ethyl acetate=6:1);
$^1$H-NMR (CDCl$_3$): δ 1.90-1.92, 2.81, 7.07-7.11, 7.15-7.18, 7.82.

Example 39

2-methyl-2-propanyl[3-fluoro-4-(1,1,1-trifluoro-2-hydroxy-2-propanyl)phenyl]carbamate To a 1,4-dioxane solution (22.4 mL) of the compound produced in Example 38 (1.49 g), tert-butyl carbamate (735 mg), palladium acetate (II) (93 mg), 4,5-bis(diphenylphosphino)-9,9-dimethyl xanthene (363 mg), and cesium carbonate (2.04 g) were added. Then, the resulting mixture was stirred under argon atmosphere at 110° C. for 1.5 hours. Insoluble matter in the reaction mixture was separated by filtration. Filtrate was concentrated. The resulting residue was purified by column chromatography on silica gel (hexane:ethyl acetate=95/5→75/25) to obtain the title compound (1.12 g) having the following physical property values.

TLC: Rf 0.40 (hexane:ethyl acetate=3:1);
$^1$H-NMR (CDCl$_3$): δ 1.52, 1.83, 3.10, 6.57, 6.97-7.00, 7.38-7.47.

Example 40

2-(4-amino-2-fluorophenyl)-1,1,1-trifluoro-2-propanol

To a dichloromethane solution (22 mL) of the compound produced in Example 39 (1.12 g), and trifluoroacetic acid (5 mL) was added thereto under ice-cooling. The resulting mixture was stirred at room temperature for 14 hours, followed by concentration under reduced pressure. The resulting residue was purified by column chromatography on silica gel (hexane:ethyl acetate=80/20→60/40) to obtain the title compound (540 mg) having the following physical property values.

TLC: Rf 0.25 (hexane:ethyl acetate=3:1);
$^1$H-NMR (CDCl$_3$): δ 1.79, 3.14, 3.86, 6.35-6.41, 6.44-6.48, 7.23-7.29.

Example 41

2-(4-amino-3,5-dichloro-2-fluorophenyl)-1,1,1-trifluoro-2-propanol

To an N,N-dimethylformamide solution (5 mL) of the compound produced in Example 40 (290 mg), N-chlorosuccinimide (347 mg) was added, and the resulting mixture was stirred at 80° C. for 17 hours. Water was added to the reaction mixture, followed by extraction with a mixed solvent of ethyl acetate and hexane (1:1). The organic layer was dried over anhydrous magnesium sulfate, and concentrated under reduced pressure. The resulting residue was purified by column chromatography on silica gel (hexane:ethyl acetate=90/10) to obtain the title compound (219 mg) having the following physical property values.

TLC: Rf 0.49 (hexane:ethyl acetate=5:1);
$^1$H-NMR (CDCl$_3$): δ 1.84, 2.82, 4.67, 7.46.

Example 42

2,6-dichloro-3-fluoro-4-{1,1,1-trifluoro-2-[(trimethylsilyl)oxy]-2-propanyl}aniline To a tetrahydrofuran solution (5 mL) of the compound produced in Example 41 (250 mg), chlorotrimethylsilane (419 µL) and imidazole (291 mg) were added, and the resulting mixture was stirred at 55° C. for three hours. A saturated ammonium chloride aqueous solution was added to the reaction mixture, followed by extraction with ethyl acetate. The organic layer was dried over anhydrous magnesium sulfate, and then concentrated under reduced pressure. The resulting residue was purified by column chromatography on silica gel (hexane:ethyl acetate=95/5) to obtain the title compound (310 mg) having the following physical property values.

TLC: Rf 0.65 (hexane:ethyl acetate=5:1);
$^1$H-NMR (CDCl$_3$): δ 0.19, 1.89, 4.63, 7.45.

Example 43

1-[2,6-dichloro-3-fluoro-4-(1,1,1-trifluoro-2-hydroxy-2-propanyl)phenyl]-3-{[5-(trifluoromethyl)-2-pyridinyl]methyl}urea

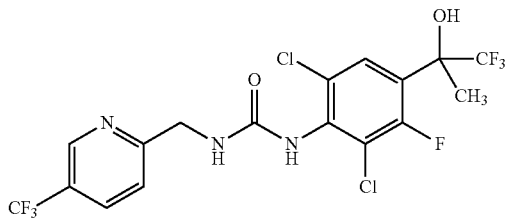 [SMILES: CC(O)(c1cc(Cl)c(NC(=O)NCc2ccc(C(F)(F)F)cn2)c(Cl)c1F)C(F)(F)F]

The compound produced in Example 42 instead of the compound produced in Example 4 was used and subjected to the same procedure as in Example 5 to obtain the title compound having the following physical property values.

TLC: Rf 0.30 (hexane:ethyl acetate=1:1);
$^1$H-NMR (CD$_3$OD): δ 1.84, 4.59, 7.64, 7.85, 8.12, 8.81.

Examples 43(1) to (3)

The compound produced in Example 42 instead of the compound produced in Example 4, and the corresponding amine instead of 1-[5-(trifluoromethyl)-2-pyridinyl]methanamine hydrochloride were used and subjected to the same procedure as in Example 5 to obtain the title compound having the following physical property values.

Example 43(1)

1-[2,6-dichloro-3-fluoro-4-(1,1,1-trifluoro-2-hydroxy-2-propanyl)phenyl]-3-{[5-(trifluoromethyl)-2-pyrimidinyl]methyl}urea TLC: Rf 0.29 (hexane:ethyl acetate=1:1);
$^1$H-NMR (CD$_3$OD): δ 1.83, 4.72, 7.83, 9.10.

Example 43(2)

1-[(5-chloro-2-pyridinyl)methyl]-3-[2,6-dichloro-3-fluoro-4-(1,1,1-trifluoro-2-hydroxy-2-propanyl)phenyl]urea TLC: Rf 0.35 (hexane:ethyl acetate=1:2);
$^1$H-NMR (CD$_3$OD): δ 1.84, 4.49, 7.45, 7.82-7.86, 8.49.

Example 43(3)

1-[2,6-dichloro-3-fluoro-4-(1,1,1-trifluoro-2-hydroxy-2-propanyl)phenyl]-3-{[5-(trifluoromethyl)-1,2,4-oxadiazol-3-yl]methyl}urea TLC: Rf 0.64 (hexane:ethyl acetate=1:2);
$^1$H-NMR (CD$_3$OD): δ 1.83, 4.63, 7.84.

Example 44

4-acetyl-2-fluorophenyl trifluoromethane sulfonate

To a dichloromethane solution (20 mL) of 1-(3-fluoro-4-hydroxyphenyl)ethanone (1.0 g) (CAS registry number: 403-14-5), triethylamine (995 µL) and trifluoromethane sulfonic acid anhydride (1.2 mL) were added under ice-cooling. The resulting mixture was stirred at room temperature for one hour. A saturated sodium hydrogencarbonate aqueous solution was added to the reaction mixture, followed by extraction with ethyl acetate. The organic layer was dried over anhydrous magnesium sulfate, and concentrated under reduced pressure. The resulting residue was purified by column chromatography on silica gel (hexane:ethyl acetate=90/10) to obtain the title compound (1.8 g) having the following physical property values.

TLC: Rf 0.57 (hexane:ethyl acetate=3:1);
$^1$H-NMR (CDCl$_3$): δ 2.63, 7.46, 7.80-7.88.

Example 45

2-fluoro-4-(1,1,1-trifluoro-2-hydroxy-2-propanyl) phenyl trifluoromethane sulfonate To a tetrahydrofuran solution (54 mL) of the compound produced in Example 44 (1.8 g) and (trifluoromethyl)trimethylsilane (2.8 mL), tetrabutyl ammonium fluoride (1 M tetrahydrofuran solution, 310 µL) was added in an ice bath, and the resulting mixture was stirred at room temperature for two hours. Tetrabutyl ammonium fluoride (1 M tetrahydrofuran solution, 7.5 mL) was added to the reaction mixture under ice-cooling, followed by stirring for 10 minutes. A saturated sodium hydrogencarbonate aqueous solution was added to the reaction mixture, followed by extraction with ethyl acetate. The organic layer was dried over anhydrous magnesium sulfate, and concentrated under reduced pressure. The resulting residue was purified by column chromatography on silica gel (hexane:ethyl acetate=90/10) to obtain the title compound (855 mg) having the following physical property values.

$^1$H-NMR (CDCl$_3$): δ 1.79, 2.52, 7.35-7.45, 7.56.

Example 46

2-methyl-2-propanyl[2-fluoro-4-(1,1,1-trifluoro-2-hydroxy-2-propanyl)phenyl]carbamate To a 1,4-dioxane solution (12 mL) of the compound produced in Example 45 (855 mg), tert-butyl carbamate (421 mg), palladium acetate (II) (54 mg), 4,5-bis(diphenylphosphino)-9,9-dimethyl xanthene (208 mg), and cesium carbonate (1.17 g) were added and reacted under irradiation with microwave (Initiator60, manufactured by Biotage) at 110° C. for one hour. The reaction mixture was filtered through Celite (product name), and the filtrate was concentrated under reduced pressure. The resulting residue was purified by column chromatography on silica gel (hexane:ethyl acetate=80/20) to obtain the title compound (160 mg) having the following physical property values.

TLC: Rf 0.85 (hexane:ethyl acetate=2:1);

$^1$H-NMR (CDCl$_3$): δ 1.53, 1.75, 2.36, 6.74, 7.27-7.39, 8.11.

Example 47

2-(4-amino-3-fluorophenyl)-1,1,1-trifluoro-2-propanol

To a dichloromethane solution (4 mL) of the compound produced in Example 46 (160 mg), trifluoroacetic acid (2 mL) was added in an ice bath. The resulting mixture was stirred at room temperature for one hour. Toluene (2 mL) was added to the reaction mixture, followed by concentration under reduced pressure. The resulting residue was purified by column chromatography on silica gel (hexane:ethyl acetate=70/30) to obtain the title compound (53 mg) having the following physical property values.

TLC: Rf 0.65 (hexane:ethyl acetate=2:1);

$^1$H-NMR (CD$_3$OD): δ 1.67, 6.95, 7.20, 7.28.

Example 48

2-chloro-6-fluoro-4-{1,1,1-trifluoro-2-[(trimethylsilyl)oxy]-2-propanyl}aniline

To an N,N-dimethylformamide solution (2 mL) of the compound produced in Example 47 (53 mg), N-chlorosuccinimide (32 mg) was added, and the resulting mixture was stirred at room temperature for 18 hours. Water was added to the reaction mixture, followed by extraction with a mixed solvent of ethyl acetate and hexane. The organic layer was dried over anhydrous magnesium sulfate, and concentrated under reduced pressure. The resulting residue was dissolved in tetrahydrofuran (2 mL), and chlorotrimethylsilane (116 μL) and imidazole (80 mg) were added to the solution, and the solution was stirred at room temperature for two hours. A saturated ammonium chloride aqueous solution was added to the reaction mixture, followed by extraction with ethyl acetate. The organic layer was dried over anhydrous magnesium sulfate, and then concentrated under reduced pressure. The resulting residue was purified by column chromatography on silica gel (hexane:ethyl acetate=95/5) to obtain the title compound (53 mg) having the following physical property values.

TLC: Rf 0.84 (hexane:ethyl acetate=3:1);

$^1$H-NMR (CDCl$_3$): δ 0.15, 1.75, 4.13, 7.13, 7.20.

Example 49

1-[2-chloro-6-fluoro-4-(1,1,1-trifluoro-2-hydroxy-2-propanyl)phenyl]-3-{[5-(trifluoromethyl)-2-pyridinyl]methyl}urea

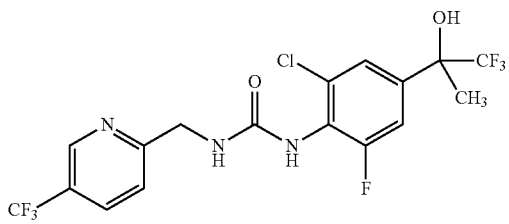 [SMILES: CC(O)(c1cc(F)c(NC(=O)NCc2ccc(C(F)(F)F)cn2)c(Cl)c1)C(F)(F)F]

The compound produced in Example 48 instead of the compound produced in Example 4 was used and subjected to the same procedure as in Example 5 to obtain the title compound having the following physical property values.

TLC: Rf 0.18 (hexane:ethyl acetate=1:1);

$^1$H-NMR (CD$_3$OD): δ 1.70, 4.59, 7.38, 7.53, 7.62, 8.12, 8.82.

Example 50

2-cyclohexyl-N-[2,6-dichloro-4-(1,1,1-trifluoro-2-hydroxy-2-propanyl)phenyl]acetamide

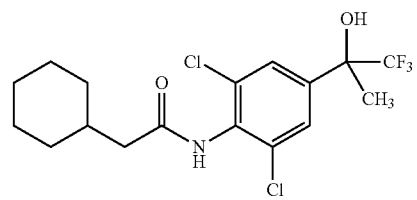 [SMILES: CC(O)(c1cc(Cl)c(NC(=O)CC2CCCCC2)c(Cl)c1)C(F)(F)F]

To a toluene solution (2 mL) of the compound produced in Example 4 (50 mg), cyclohexylacetyl chloride (27 mg) was added, followed by stirring under irradiation with microwave (Initiator60, manufactured by Biotage) at 100° C. for one hour. Tetrabutyl ammonium fluoride (1 M tetrahydrofuran solution, 288 μL) was added to the reaction mixture, and the resulting mixture was stirred at room temperature for 20 hours. A saturated sodium hydrogencarbonate aqueous solution was added to the reaction mixture, followed by extraction with ethyl acetate. The organic layer was concentrated under reduced pressure. The resulting residue was purified by column chromatography on silica gel (hexane:ethyl acetate=60/40) to obtain the title compound (8 mg) having the following physical property values.

TLC: Rf 0.50 (hexane:ethyl acetate=3:1);

$^1$H-NMR (CD$_3$OD): δ 1.02-1.40, 1.65-1.91, 2.31, 7.67.

Examples 50(1) to (7)

The corresponding acid chloride instead of cyclohexylacetyl chloride was used and subjected to the same procedure as in Example 50 to obtain the title compound having the following physical property values.

Example 50(1)

N-[2,6-dichloro-4-(1,1,1-trifluoro-2-hydroxy-2-propanyl)phenyl]-2-(4-fluorophenyl)acetamide

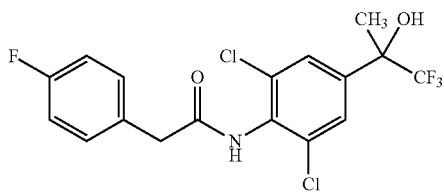 [SMILES: CC(O)(c1cc(Cl)c(NC(=O)Cc2ccc(F)cc2)c(Cl)c1)C(F)(F)F]

TLC: Rf 0.47 (hexane:ethyl acetate=2:1);
$^1$H-NMR (DMSO-$d_6$): δ 1.70, 3.68, 6.97, 7.12-7.18, 7.35-7.40, 7.67, 10.11.

Example 50(2)

N-[2,6-dichloro-4-(1,1,1-trifluoro-2-hydroxy-2-propanyl)phenyl]-3-(4-fluorophenyl)propanamide LC retention time (min), LC condition 1: 0.97;
$^1$H-NMR (DMSO-$d_6$): δ 1.70, 2.62-2.67, 2.89-2.94, 6.96, 7.07-7.12, 7.27-7.32, 7.66, 9.87.

Example 50(3)

N-[2,6-dichloro-4-(1,1,1-trifluoro-2-hydroxy-2-propanyl)phenyl]-2-[4-(trifluoromethyl)phenyl]acetamide TLC: Rf 0.70 (hexane:ethyl acetate=1:1);
$^1$H-NMR (CD$_3$OD): δ 1.71, 3.86, 7.60-7.67.

Example 50(4)

N-[2,6-dichloro-4-(1,1,1-trifluoro-2-hydroxy-2-propanyl)phenyl]-3,3-dimethylbutane amide TLC: Rf 0.18 (hexane:ethyl acetate=4:1);
$^1$H-NMR (DMSO-$d_6$): δ 1.05, 1.70, 2.22, 6.97, 7.67, 9.74.

Example 50(5)

N-[2,6-dichloro-4-(1,1,1-trifluoro-2-hydroxy-2-propanyl)phenyl]-3-[4-(trifluoromethyl)phenyl]propanamide TLC: Rf 0.50 (hexane:ethyl acetate=1:1);
$^1$H-NMR (DMSO-$d_6$): δ 1.68, 2.70, 3.01, 6.94, 7.48, 7.62-7.65, 9.89.

Example 50(6)

N-[2,6-dichloro-4-(1,1,1-trifluoro-2-hydroxy-2-propanyl)phenyl]-3-[3-(trifluoromethyl)phenyl]propanamide LC retention time (min), LC condition 2: 1.03;
$^1$H-NMR (DMSO-$d_6$): δ 1.69, 2.72, 3.02, 6.94, 7.50-7.65, 9.87.

Example 50(7)

N-[2,6-dichloro-4-(1,1,1-trifluoro-2-hydroxy-2-propanyl)phenyl]-3-[2-(trifluoromethyl)phenyl]propanamide LC retention time (min), LC condition 2: 1.03;
$^1$H-NMR (DMSO-$d_6$): δ 1.70, 2.67-2.71, 3.06-3.11, 6.95, 7.42, 7.54-7.70, 9.94.

Example 51

2-(4-bromo-3-methyl phenyl)-1,1,1-trifluoro-2-propanol

To a tetrahydrofuran solution (40 mL) of 1-(4-bromo-3-methyl phenyl)ethanone (4.0 g) (CAS registry number: 37074-40-1), (trifluoromethyl)trimethylsilane (8.3 mL) and tetrabutyl ammonium fluoride (1 M tetrahydrofuran solution, 0.9 mL) were added under ice-cooling. The resulting mixture was stirred at room temperature for one hour. Tetrabutyl ammonium fluoride (1 M tetrahydrofuran solution, 22.5 mL) was added to a reaction mixture under ice-cooling, and then the saturated ammonium chloride aqueous solution was added, followed by extraction with ethyl acetate. The organic layer was washed with saturated brine, dried over sodium sulfate, and concentrated under reduced pressure. The resulting residue was purified by column chromatography on silica gel (hexane:ethyl acetate=95:5→85:15) to obtain the title compound (5.3 g) having the following physical property values.

TLC: Rf 0.51 (hexane:ethyl acetate=5:1);
$^1$H-NMR (CDCl$_3$): δ 1.76, 2.43, 2.48, 7.23-7.26, 7.45, 7.54.

Example 52

2-methyl-2-propanyl[2-methyl-4-(1,1,1-trifluoro-2-hydroxy-2-propanyl)phenyl]carbamate To a 1,4-dioxane solution (80 mL) of the compound produced in Example 51 (4.5 g), 4,5-bis(diphenylphosphino)-9,9-dimethyl xanthene (1.4 g), palladium acetate (II) (360 mg), tert-butyl carbamate (2.4 g), and cesium carbonate (7.8 g) were added. The resulting mixture was heated and refluxed for 1.5 hours. The reaction mixture was diluted with ethyl acetate. Insoluble matter was separated by filtration through a Celite (product name), and the filtrate was concentrated under reduced pressure. The resulting residue was purified by column chromatography on silica gel (hexane:ethyl acetate=90:10→80:20→60:40) to obtain the title compound (1.7 g) having the following physical property values.

TLC: Rf 0.49 (hexane:ethyl acetate=2:1);
$^1$H-NMR (CDCl$_3$): δ 1.53, 1.75, 2.28, 2.67, 6.32, 7.36-7.39, 7.85-7.89.

Example 53

2-(4-amino-3-methyl phenyl)-1,1,1-trifluoro-2-propanol

To a dichloromethane solution (20 mL) of the compound produced in Example 52 (1.7 g), trifluoroacetic acid (12 mL) was added under ice-cooling, and the resulting mixture was stirred at room temperature for one hour. Toluene was added to the reaction mixture, followed by concentration under reduced pressure. A saturated sodium hydrogencarbonate aqueous solution was added to the resulting residue, followed by extraction with ethyl acetate. The organic layer was dried over anhydrous sodium sulfate, and then concentrated under reduced pressure to obtain the title compound (743 mg) having the following physical property values.

TLC: Rf 0.54 (hexane:ethyl acetate=1:1);
$^1$H-NMR (CDCl$_3$): δ 1.73, 2.18, 2.27, 3.66, 6.67, 7.20-7.26.

Example 54

2-methyl-4-{1,1,1-trifluoro-2-[(trimethylsilyl)oxy]-2-propanyl}aniline

To a tetrahydrofuran solution (15 mL) of the compound produced in Example 53 (743 mg), imidazole (1.15 g) and chlorotrimethylsilane (1.93 mL) were added. The resulting mixture was stirred at room temperature for one hour. A saturated ammonium chloride aqueous solution was added to the reaction mixture, followed by extraction with ethyl acetate. The organic layer was dried over anhydrous sodium sulfate, and concentrated under reduced pressure to obtain the title compound (990 mg) having the following physical property values.

TLC: Rf 0.55 (hexane:ethyl acetate=2:1);
$^1$H-NMR (CDCl$_3$): δ 0.11, 1.76, 2.17, 3.64, 6.62-6.65, 7.18.

Example 55

2-chloro-6-methyl-4-{1,1,1-trifluoro-2-[(trimethylsilyl)oxy]-2-propanyl}aniline

To an N,N-dimethylformamide solution (8 mL) of the compound produced in Example 54 (960 mg), N-chlorosuccinimide (439 mg) was added. The resulting mixture was stirred at room temperature for six hours. A saturated sodium hydrogencarbonate aqueous solution was added to the reaction mixture, followed by extraction with ethyl acetate. The organic layer was washed with saturated brine, dried over anhydrous sodium sulfate, and then concentrated under reduced pressure. The resulting residue was purified by column chromatography on silica gel (hexane:ethyl acetate=100:0→98:2) to obtain the title compound (619 mg) having the following physical property values.

TLC: Rf 0.47 (hexane:ethyl acetate=8:1);
$^1$H-NMR (CDCl$_3$): δ 0.14, 1.75, 2.22, 4.07, 7.11, 7.30.

Example 56

1-[2-chloro-6-methyl-4-(1,1,1-trifluoro-2-hydroxy-2-propanyl)phenyl]-3-{[5-(trifluoromethyl)-2-pyrimidinyl]methyl}urea

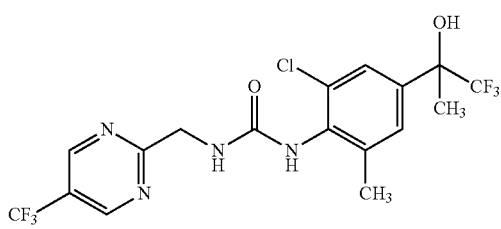 [SMILES: Cc1cc(C(C)(O)C(F)(F)F)cc(Cl)c1NC(=O)NCc1ncc(C(F)(F)F)cn1]

To a tetrahydrofuran solution (0.4 mL) of solution of the compound produced in Example 55 (20 mg), triphosgene (20 mg) and diisopropyl ethyl amine (11 µL) were added. The resulting mixture was stirred at room temperature for one hour. The reaction mixture was concentrated under reduced pressure. The resulting residue was dissolved in tetrahydrofuran (0.4 mL), and 1-[5-(trifluoromethyl)-2-pyridinyl]methanamine hydrochloride (19 mg) and diisopropyl ethyl amine (53 µL) were added thereto. The resulting mixture was stirred at 45° C. for 17 hours. Tetrabutyl ammonium fluoride (1 M tetrahydrofuran solution, 73 µL) was added to the reaction mixture, the resulting mixture was stirred at room temperature for one hour. A saturated ammonium chloride aqueous solution was added to the reaction mixture, followed by extraction with ethyl acetate. The organic layer was washed with saturated brine, dried over anhydrous sodium sulfate, and then concentrated under reduced pressure. The resulting residue was purified by column chromatography on silica gel (hexane:ethyl acetate=70:30→50:50) to obtain the title compound (20 mg) having the following physical property values.

TLC: Rf 0.47 (hexane:ethyl acetate=1:2);
$^1$H-NMR (CDCl$_3$): δ 1.78, 2.43, 2.56, 4.80, 5.57, 6.21, 7.43, 7.57, 8.93.

Examples 56(1) to (3)

The corresponding amine instead of 1-[5-(trifluoromethyl)-2-pyridinyl]methanamine hydrochloride was used and subjected to the same procedure as in Example 56 to obtain the title compound having the following physical property values.

Example 56(1)

1-[2-chloro-6-methyl-4-(1,1,1-trifluoro-2-hydroxy-2-propanyl)phenyl]-3-{[5-(trifluoromethyl)-2-pyridinyl]methyl}urea TLC: Rf 0.40 (hexane:ethyl acetate=1:2);
$^1$H-NMR (CDCl$_3$): δ 1.76, 2.38, 2.59, 4.62, 5.55, 6.20, 7.39, 7.47, 7.55, 7.91, 8.75.

Example 56(2)

1-[2-chloro-6-methyl-4-(1,1,1-trifluoro-2-hydroxy-2-propanyl)phenyl]-3-{[6-(trifluoromethyl)-3-pyridinyl]methyl}urea TLC: Rf 0.36 (hexane:ethyl acetate=1:2);
$^1$H-NMR (CDCl$_3$): δ 1.76, 2.37, 2.53, 4.54, 4.89, 5.97, 7.40, 7.56, 7.66, 7.86-7.88, 8.64.

Example 56(3)

1-[2-chloro-6-methyl-4-(1,1,1-trifluoro-2-hydroxy-2-propanyl)phenyl]-3-[(5-chloro-2-pyridinyl)methyl]urea TLC: Rf 0.49 (hexane:ethyl acetate=1:2);
$^1$H-NMR (CDCl$_3$): δ 1.76, 2.36, 2.50, 4.52, 5.45, 7.30, 7.38, 7.53, 7.65, 8.45.

Example 57

2,2,2-trifluoro-1-(3-methyl-4-nitrophenyl)ethanol

To a tetrahydrofuran solution (40 mL) of 3-methyl-4-nitrobenzaldehyde (2.5 g) (CAS registry number: 18515-67-

8), (trifluoromethyl)trimethylsilane (6.7 mL) and tetrabutyl ammonium fluoride (1 M tetrahydrofuran solution, 0.76 mL) were added under ice-cooling. The resulting mixture was stirred at room temperature for 30 minutes. Tetrabutyl ammonium fluoride (1 M tetrahydrofuran solution, 18 mL) was added thereto under ice-cooling, and the resulting mixture was stirred at room temperature for 30 minutes. A saturated ammonium chloride aqueous solution was added to the reaction mixture, followed by extraction with ethyl acetate. The organic layer was washed with saturated brine, dried over anhydrous sodium sulfate, and then concentrated under reduced pressure. The resulting residue was purified by column chromatography on silica gel (hexane:ethyl acetate=90:10→82:18→50:50) to obtain the title compound (2.0 g) having the following physical property values.

TLC: Rf 0.50 (hexane:ethyl acetate=2:1);

$^1$H-NMR (CDCl$_3$): δ 2.64, 2.89, 5.06-5.14, 7.46-7.49, 7.99-8.02.

Example 58

1-(4-amino-3-methyl phenyl)-2,2,2-trifluoroethanol

To an ethanol solution (90 mL) of the compound produced in Example 57 (1.95 g), 5% palladium/carbon (50% water-containing product, 325 mg) was added. The resulting mixture was stirred under the hydrogen atmosphere for 1.5 hours. The reaction mixture was diluted with ethyl acetate. The reaction mixture was filtered through a Celite (product name), and the filtrate was concentrated under reduced pressure. The resulting residue was purified by column chromatography on silica gel (hexane:ethyl acetate=80:20→67:33→0:100) to obtain the title compound (1.50 g) having the following physical property value.

TLC: Rf 0.34 (hexane:ethyl acetate=2:1);

$^1$H-NMR (CDCl$_3$): δ 2.18, 2.37, 3.72, 4.83-4.92, 6.68, 7.11-7.15.

Example 59

4-(1-{[dimethyl(2-methyl-2-propanyl)silyl]oxy}-2,2,2-trifluoroethyl)-2-methyl aniline To an N,N-dimethylformamide solution (30 mL) of the compound produced in Example 58 (1.50 g), imidazole (2.50 g) and chloro(dimethyl) (2-methyl-2-propanyl)silane (4.94 g) were added. The resulting mixture was stirred at room temperature for 2.5 hours, and then stirred at 50° C. for one hour. Water was added to the reaction mixture, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=95:5→90:10) to obtain the title compound (507 mg) having the following physical property values.

TLC: Rf 0.63 (hexane:ethyl acetate=2:1);

$^1$H-NMR (CDCl$_3$): δ 0.11, 0.89, 2.17, 3.66, 4.75-4.81, 6.63-6.66, 7.09.

Example 60

1-[2-methyl-4-(2,2,2-trifluoro-1-hydroxyethyl)phenyl]-3-{[5-(trifluoromethyl)-2-pyridinyl]methyl}urea

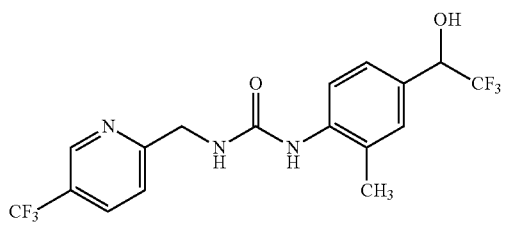 [SMILES: Cc1cc(C(O)C(F)(F)F)ccc1NC(=O)NCc1ccc(C(F)(F)F)cn1]

To a tetrahydrofuran solution (0.6 mL) of the compound produced in Example 59 (30 mg), triphosgene (31 mg) and diisopropyl ethyl amine (17 µL) were added. The resulting mixture was stirred at room temperature for one hour. The reaction mixture was concentrated under reduced pressure, and the resulting residue was dissolved in tetrahydrofuran (0.6 mL), and 1-[5-(trifluoromethyl)-2-pyridinyl]methanamine hydrochloride (30 mg) and diisopropyl ethyl amine (81 µL) were added thereto, followed by stirring at room temperature for one hour. To the reaction mixture, tetrabutyl ammonium fluoride (1 M tetrahydrofuran solution, 112 µL) was added. The reaction mixture was stirred at room temperature for one hour, and then tetrabutyl ammonium fluoride (1 M tetrahydrofuran solution, 940 µL) was added. The reaction mixture was stirred at room temperature for 30 minutes. To the reaction mixture, a saturated ammonium chloride aqueous solution was added, followed by extraction with ethyl acetate. The organic layer was washed with saturated brine, dried over anhydrous magnesium sulfate, concentrated under reduced pressure. The resulting residue was purified by column chromatography on silica gel (hexane:ethyl acetate=70:30→50:50→30:70) to obtain the title compound (32 mg) having the following physical property values.

TLC: Rf 0.46 (hexane:ethyl acetate=1:2);

$^1$H-NMR (DMSO-d$_6$): δ 2.22, 4.51, 4.95-5.05, 6.66, 7.18, 7.24, 7.30, 7.58, 7.83, 8.02, 8.21, 8.92.

Example 61

2-chloro-4-(1-{[dimethyl(2-methyl-2-propanyl)silyl]oxy}-2,2,2-trifluoroethyl)-6-methyl aniline To an acetonitrile solution (20 mL) of the compound produced in Example 59 (470 mg), 1,3-dichloro-5,5-dimethylhydantoin (290 mg) was added. The resulting mixture was stirred at room temperature for 40 minutes. A saturated ammonium chloride aqueous solution was added to the reaction mixture, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=95:5→90:10) to obtain the title compound (435 mg) having the following physical property values.

TLC: Rf 0.58 (hexane:ethyl acetate=8:1);

$^1$H-NMR (CDCl$_3$): δ 0.12, 0.91, 2.23, 4.11, 4.73-4.80, 7.04, 7.24.

Example 62

1-[2-chloro-6-methyl-4-(2,2,2-trifluoro-1-hydroxy-ethyl)phenyl]-3-{[5-(trifluoromethyl)-2-pyridinyl]methyl}urea

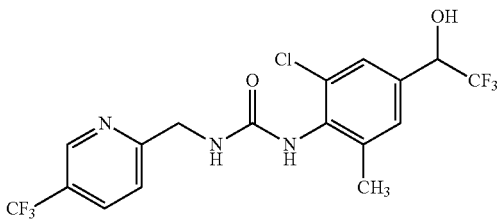 [SMILES: Cc1cc(C(O)C(F)(F)F)cc(Cl)c1NC(=O)NCc1ccc(C(F)(F)F)cn1]

The compound produced in Example 61 instead of the compound produced in Example 59 was used and subjected to the same procedure as in Example 60 to obtain the title compound having the following physical property values.

TLC: Rf 0.44 (hexane:ethyl acetate=1:2);
$^1$H-NMR (DMSO-$d_6$): δ 2.23, 4.47, 5.11-5.20, 6.92, 7.03, 7.30, 7.41, 7.57, 8.13, 8.23, 8.89.

Examples 62(1) to (3)

The compound produced in Example 61 instead of the compound produced in Example 59, and the corresponding amine instead of 1-[5-(trifluoromethyl)-2-pyridinyl]methanamine hydrochloride were used and subjected to the same procedure as in Example 60 to obtain the title compound having the following physical property values.

Example 62(1)

1-[2-chloro-6-methyl-4-(2,2,2-trifluoro-1-hydroxy-ethyl)phenyl]-3-{[5-(trifluoromethyl)-2-pyrimidinyl]methyl}urea TLC: Rf 0.48 (hexane:ethyl acetate=1:2);
$^1$H-NMR (DMSO-$d_6$): δ 2.22, 4.59, 5.10-5.19, 6.90-6.97, 7.29, 7.40, 8.18, 9.24.

Example 62(2)

1-[2-chloro-6-methyl-4-(2,2,2-trifluoro-1-hydroxy-ethyl)phenyl]-3-{[6-(trifluoromethyl)-3-pyridinyl]methyl}urea TLC: Rf 0.56 (hexane:ethyl acetate=1:2);
$^1$H-NMR (DMSO-$d_6$): δ 2.21, 4.40, 5.11-5.20, 6.92, 6.98, 7.30, 7.41, 7.87-7.97, 8.04, 8.67.

Example 62(3)

1-[2-chloro-6-methyl-4-(2,2,2-trifluoro-1-hydroxy-ethyl)phenyl]-3-[(5-chloro-2-pyridinyl)methyl]urea TLC: Rf 0.33 (hexane:ethyl acetate=1:2);
$^1$H-NMR (DMSO-$d_6$): δ 2.22, 4.36, 5.11-5.19, 6.90-6.97, 7.30-7.40, 7.93, 8.07, 8.55.

Example 63

2-[4-(dibenzylamino)phenyl]-4,4,4-trifluoro-2-butanol

To a tetrahydrofuran solution (4 mL) of N,N-dibenzyl-4-bromoaniline (300 mg) (CAS registry number: 65145-14-4), n-butyllithium (1.64 M hexane solution, 0.78 mL) was added dropwise at −78° C. The reaction mixture was stirred at −78° C. for 10 minutes, and then 4,4,4-trifluoro-2-butanone (214 mg) was added thereto. The mixture was stirred at room temperature for one hour. A saturated ammonium chloride aqueous solution was added to the reaction mixture, followed by extraction with ethyl acetate. The organic layer was dried over anhydrous magnesium sulfate, and then concentrated under reduced pressure. The resulting residue was purified by column chromatography on silica gel (hexane:ethyl acetate=85:15) to obtain the title compound (100 mg) having the following physical property values.

TLC: Rf 0.50 (hexane:ethyl acetate=5:1);
$^1$H-NMR (CDCl$_3$): δ 1.67, 2.51-2.67, 4.65, 6.68-6.73, 7.22-7.38.

Example 64

2-(4-aminophenyl)-4,4,4-trifluoro-2-butanol

To a mixed solution of methanol (2 mL) and ethyl acetate (2 mL) of the compound produced in Example 63 (100 mg), 5% palladium/carbon (50% water containing product, 10 mg) was added. The reaction mixture was stirred under the hydrogen atmosphere at room temperature for two hours. The reaction mixture was filtered through a Celite (product name), and the filtrate was concentrated under reduced pressure to obtain the title compound.

TLC: Rf 0.15 (hexane:ethyl acetate=3:1);
1H-NMR (CD3OD): δ 1.60, 2.56-2.70, 6.83-6.86, 7.31-7.34.

Example 65

4-{4,4,4-trifluoro-2-[(trimethylsilyl)oxy]-2-butanyl}aniline

To a tetrahydrofuran solution (5 mL) of the compound produced in Example 64 (54 mg), chlorotrimethylsilane (120 μL) and imidazole (83 mg) were added. The resulting mixture was stirred at room temperature for 17 hours. A saturated ammonium chloride aqueous solution was added to the reaction mixture, followed by extraction with ethyl acetate. The organic layer was dried over anhydrous magnesium sulfate, and concentrated under reduced pressure. The resulting residue was purified by column chromatography on silica gel (hexane:ethyl acetate=85:15) to obtain the title compound (31 mg) having the following physical property values.

TLC: Rf 0.61 (hexane:ethyl acetate=2:1);
$^1$H-NMR (CDCl$_3$): δ 0.04, 1.74, 2.38-2.60, 3.65, 6.63-6.66, 7.18-7.21.

Example 66

2,6-dichloro-4-{4,4,4-trifluoro-2-[(trimethylsilyl)oxy]-2-butanyl}aniline

To an N,N-dimethylformamide solution (2 mL) of the compound produced in Example 65 (31 mg), N-chlorosuccinimide (31 mg) was added. The resulting mixture was stirred at 40° C. for 20 hours. Water was added to the reaction mixture, followed by extraction with ethyl acetate. The organic layer was dried over anhydrous magnesium sulfate, and concentrated under reduced pressure. The resulting residue was purified by column chromatography on silica gel (hexane:ethyl acetate=95:5) to obtain the title compound (21 mg) having the following physical property values.

TLC: Rf 0.80 (hexane:ethyl acetate=5:1);

$^1$H-NMR (CDCl$_3$): 0.09, 1.71, 2.37-2.56, 4.42, 7.22.

Example 67

1-[2,6-dichloro-4-(4,4,4-trifluoro-2-hydroxy-2-butanyl)phenyl]-3-{[5-(trifluoromethyl)-2-pyridinyl]methyl}urea

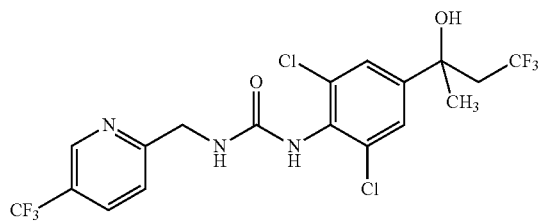 [SMILES: CC(O)(CC(F)(F)F)c1cc(Cl)c(NC(=O)NCc2ccc(C(F)(F)F)cn2)c(Cl)c1]

To a dichloromethane solution (2 mL) of the compound produced in Example 66 (21 mg), N,N-diisopropyl ethyl amine (11 µL) and triphosgene (19 mg) were added. The resulting mixture was stirred at 40° C. for one hour. The reaction mixture concentrated under reduced pressure, and then, the resulting residue was dissolved in tetrahydrofuran (2 mL). N,N-diisopropyl ethyl amine (50 µL) and 1-[5-(trifluoromethyl)-2-pyridinyl]methanamine hydrochloride (14 mg) were added to the solution, and the solution was stirred at 30° C. for 20 hours. A saturated sodium hydrogencarbonate aqueous solution was added to the reaction mixture, followed by extraction with ethyl acetate. The organic layer was washed with saturated brine, dried over anhydrous magnesium sulfate, and concentrated under reduced pressure. The resulting residue was dissolved in tetrahydrofuran (1 mL), and tetrabutyl ammonium fluoride (1 M tetrahydrofuran solution, 582 µL) was added, and the solution was stirred at room temperature for one hour. A saturated ammonium chloride aqueous solution was added to the reaction mixture, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=50:50) to obtain the title compound (2 mg) having the following physical property values.

TLC: Rf 0.35 (hexane:ethyl acetate=1:2);

$^1$H-NMR (CDCl$_3$): δ 1.69, 2.42, 2.56-2.68, 4.62, 5.81, 6.62, 7.47, 7.49, 7.91, 8.76.

Example 68

1-nitro-4-(1,1,1-trifluoro-2-methoxy-2-propanyl)benzene

To an N,N-dimethylformamide solution (13 mL) of the compound produced in Example 1 (1.49 g), sodium hydride (60% in oil, 278 mg) was added under ice-cooling. The resulting mixture was stirred at room temperature for 15 minutes. Methyl iodide (987 mg) was added to the reaction mixture under ice-cooling, the resulting mixture was stirred at room temperature for one hour. A saturated ammonium chloride aqueous solution and water were added to the reaction mixture under ice-cooling, followed by extraction with ethyl acetate. The organic layer was washed sequentially with water and saturated brine, and dried over anhydrous magnesium sulfate, followed by concentration under reduced pressure. The resulting residue was purified by column chromatography on silica gel (hexane:ethyl acetate=100:0→80:20) to obtain the title compound (1.55 g) having the following physical property values.

TLC: Rf 0.69 (hexane:ethyl acetate=4:1);

$^1$H-NMR (CDCl$_3$): δ 1.83, 3.29, 7.70-7.73, 8.25-8.28.

Example 69

4-(1,1,1-trifluoro-2-methoxy-2-propanyl)aniline

To a methanol solution (21 mL) of the compound produced in Example 68 (1.55 g), 5% palladium/carbon (50% water-containing product, 155 mg) was added. The resulting mixture was stirred under the hydrogen atmosphere at room temperature for two hours. The reaction mixture was filtered through a Celite (product name), and then, the filtrate was concentrated to obtain the title compound (1.35 g) having the following physical property values.

TLC: Rf 0.33 (hexane:ethyl acetate=4:1);

$^1$H-NMR (CDCl$_3$): δ 1.72, 3.19, 3.75, 6.67-6.70, 7.27-7.29.

Example 70

2,6-dichloro-4-(1,1,1-trifluoro-2-methoxy-2-propanyl)aniline

To an acetonitrile solution (25 mL) of the compound produced in Example 69 (1.35 g), 1,3-dichloro-5,5-dimethylhydantoin (1.21 g) was added under ice-cooling. The resulting mixture was stirred at room temperature for one hour, and then stirred at 45° C. for three hours. An aqueous solution of sodium sulfite was added to the reaction mixture under ice-cooling. The reaction mixture was stirred at room temperature for 30 minutes, followed by extraction with ethyl acetate. The organic layer was washed sequentially with an aqueous solution of sodium sulfite, water, and saturated brine, then dried over anhydrous magnesium sulfate, and concentrated under reduced pressure. The resulting residue was purified by column chromatography on silica gel (hexane:ethyl acetate=100:0→80:20) to obtain the title compound (1.74 g) having the following physical property.

TLC: Rf 0.62 (hexane:ethyl acetate=4:1);

$^1$H-NMR (CDCl$_3$): δ 1.70, 3.22, 4.56, 7.31.

Example 71

1-[2,6-dichloro-4-(1,1,1-trifluoro-2-methoxy-2-propanyl)phenyl]-3-{[5-(trifluoromethyl)-2-pyridinyl]methyl}urea

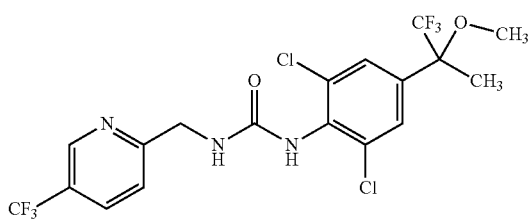 [SMILES: COC(C)(c1cc(Cl)c(NC(=O)NCc2ccc(C(F)(F)F)cn2)c(Cl)c1)C(F)(F)F]

To a tetrahydrofuran solution (1 mL) of the compound produced in Example 70 (30 mg), diisopropyl ethyl amine (20 µL) and triphosgene (34 mg) were added. The resulting mixture was stirred at room temperature for 30 minutes, followed by concentration under reduced pressure. The resulting residue was dissolved in tetrahydrofuran (1 mL), and 1-[5-(trifluoromethyl)-2-pyridinyl]methanamine hydrochloride (24 mg) and triethylamine (35 µL) were added thereto. The resulting mixture was stirred overnight at room temperature. Water was added to the reaction mixture, followed by extraction with ethyl acetate. The organic layer was washed sequentially with water and saturated brine, dried over anhydrous magnesium sulfate, and concentrated under reduced pressure. The resulting residue was washed with hexane-ethyl acetate (9:1) to obtain the title compound (40 mg) having the following physical property values.

TLC: Rf 0.32 (hexane:ethyl acetate=1:1);
$^1$H-NMR (DMSO-$d_6$): δ 1.78, 3.19, 4.46, 7.15, 7.54-7.62, 8.23, 8.48, 8.88.

Example 72

{[1,1-difluoro-2-(4-nitrophenyl)-2-propanyl]oxy}(trimethyl)silane

To an N,N-dimethylformamide solution (15 mL) of 1-(4-nitrophenyl)ethanone (CAS registry number: 100-19-6) (1.00 g), cesium fluoride (183 mg) was added, and (difluoromethyl)(trimethyl)silane (CAS registry number: 65864-64-4) (2.26 g) was added under ice-cooling. The reaction mixture was stirred under ice-cooling for one hour, then stirred at room temperature for two hours, and then stirred at 45° C. for two hours. Water was added to the reaction mixture, followed by extraction with a mixed solvent of ethyl acetate and hexane. The organic layer was washed sequentially with water and saturated brine, and dried over anhydrous sodium sulfate, followed by concentration under reduced pressure. The resulting residue was purified by column chromatography on silica gel (hexane:ethyl acetate=100/0→95/5→65/35→40/60) to obtain the title compound (454 mg) having the following physical property values.

$^1$H-NMR (CDCl$_3$): δ 0.17, 1.76, 5.58, 7.66-7.69, 8.21-8.26.

Example 73

4-{1,1-difluoro-2-[(trimethylsilyl)oxy]-2-propanyl}aniline

To a methanol solution (4.1 mL) of the compound produced in Example 72 (237 mg), 5% palladium/carbon (manufactured by N.E. CHEMCAT CORPORATION, water-containing product, KER type) (20 mg) was added, and the resulting solution was stirred under the hydrogen atmosphere at room temperature for two hours. The reaction mixture was filtered through a Celite (product name), and the filtrate was concentrated under reduced pressure to obtain the title compound (203 mg) having the following physical property values.

TLC: Rf 0.26 (hexane:ethyl acetate=4:1);
$^1$H-NMR (CDCl$_3$): δ 0.08, 1.65, 3.68, 5.51, 6.64-6.69, 7.22-7.25.

Example 74

2,6-dichloro-4-{1,1-difluoro-2-[(trimethylsilyl)oxy]-2-propanyl}aniline

To an N,N-dimethylformamide solution (5.2 mL) of the compound (203 mg) obtained in Example 73, N-chlorosuccinimide (209 mg) was added, and the resulting mixture was stirred at 35° C. for one hour and then stirred at 45° C. overnight. The reaction mixture was diluted with a mixed solvent of ethyl acetate and hexane, then washed sequentially with water and saturated brine, and dried over anhydrous sodium sulfate, followed by concentration under reduced pressure. To a tetrahydrofuran solution (5.2 mL) of the resulting residue, imidazole (106 mg) and chlorotrimethylsilane (0.20 mL) were added, and the resulting mixture solution was stirred at room for two hours. Water was added to the reaction mixture, followed by extraction with ethyl acetate. The organic layer was washed sequentially with water and saturated brine, dried over anhydrous sodium sulfate, and then concentrated under reduced pressure. The resulting residue was purified by column chromatography on silica gel (hexane:ethyl acetate=100/0→95/5→90/10) to obtain the title compound (238 mg) having the following physical property values.

TLC: Rf 0.76 (hexane:ethyl acetate=4:1);
$^1$H-NMR (CDCl$_3$): δ 0.13, 1.63, 4.47, 5.47, 7.26.

Example 75

1-[2,6-dichloro-4-(1,1-difluoro-2-hydroxy-2-propanyl)phenyl]-3-{[5-(trifluoromethyl)-2-pyridinyl]methyl}urea The compound produced in Example 74 instead of the compound produced in Example 4 was used and subjected to the same procedure as in Example 5 to obtain the title compound having the following physical property values.

TLC: Rf 0.35 (hexane:ethyl acetate=1:2);
$^1$H-NMR (DMSO-$d_6$): δ 1.50, 4.47, 6.02, 7.10, 7.57-7.59, 8.22-8.26, 8.39, 8.89.

Example 76

1-(4-amino-3,5-dichlorophenyl)-2,2,2-trifluoroethanone

To an N,N-dimethylformamide solution (30 mL) of 1-(4-aminophenyl)-2,2,2-trifluoroethanone (CAS registry number: 23516-79-2) (2.60 g), N-chlorosuccinimide (3.70 g) was added, followed by stirring at 40° C. for 18 hours. An aqueous solution of saturated sodium hydrogencarbonate was added to reaction mixture, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=95/5) to obtain the title compound (3.20 g) having the following physical property values.

TLC: Rf 0.55 (hexane:ethyl acetate=5:1);
$^1$H-NMR (CDCl$_3$): δ 5.26, 7.94.

Example 77

1-(4-amino-3,5-dichlorophenyl)-2,2,2-trifluoroethanol

To a methanol solution (10 mL) of the compound produced in Example 76 (1.00 g), sodium borohydride (146 mg) was added under ice-cooling, followed by stirring at room temperature for one hour. A saturated ammonium chloride aqueous solution was added to the reaction mixture, followed by extraction with ethyl acetate. The organic layer was washed with saturated brine, dried over anhydrous magnesium sulfate, and concentrated under reduced pressure to obtain the title compound (975 mg) having the following physical property values.

$^1$H-NMR (CDCl$_3$): δ 4.58, 4.83-4.91, 7.31.

Example 78

4-(1-azide-2,2,2-trifluoroethyl)-2,6-dichloroaniline

To a toluene solution (10 mL) of the compound produced in Example 77 (314 mg), 2,3,4,6,7,8,9,10-octahydropyrimido[1,2-a]azepine (CAS registry number: 41015-70-7) (0.22 mL) and diphenyl phosphorazidate (CAS registry number: 26386-88-9) (0.33 mL) were added, followed by stirring at 45° C. for three hours. A saturated sodium hydrogencarbonate aqueous solution was added to the reaction mixture, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=95/5) to obtain the title compound (314 mg) having the following physical property values.

TLC: Rf 0.70 (hexane:ethyl acetate=5:1);
$^1$H-NMR (CDCl$_3$): δ 4.65, 4.75, 7.26.

Example 79

1-[4-(1-amino-2,2,2-trifluoroethyl)-2,6-dichlorophenyl]-3-{[6-(trifluoromethyl)-3-pyridinyl]methyl}urea

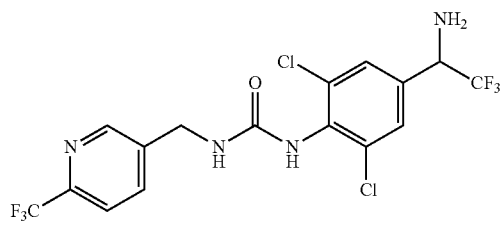 [SMILES: NC(c1cc(Cl)c(NC(=O)NCc2ccc(C(F)(F)F)nc2)c(Cl)c1)C(F)(F)F]

To a tetrahydrofuran solution (5 mL) of the compound produced in Example 78 (310 mg), triphosgene (355 mg) and N,N-diisopropyl ethyl amine (207 μL) were added, and the resulting mixture was stirred at room temperature for one hour, and then concentrated under reduced pressure. The resulting residue (55 mg) was dissolved in tetrahydrofuran (2 mL), and N,N-diisopropyl ethyl amine (153 μL) and 1-[6-(trifluoromethyl)-3-pyridinyl]methanamine (CAS registry number: 23586-96-1) (47 mg) were added thereto, followed by stirring at 45° C. for two hours. A saturated sodium hydrogencarbonate aqueous solution was added to the reaction mixture, followed by extraction with ethyl acetate. The organic layer was washed with saturated brine, dried over anhydrous magnesium sulfate, and concentrated under reduced pressure. The resulting residue was dissolved in tetrahydrofuran (2 mL), and water (0.2 mL) and triphenylphosphine (83 mg) were added thereto. The resulting solution was stirred at room temperature for 30 minutes, and stirred at 50° C. for four hours. The reaction mixture was diluted with water, followed by extraction with ethyl acetate. The organic layer was washed with saturated brine, dried over anhydrous magnesium sulfate, and concentrated under reduced pressure. The resulting residue was purified by column chromatography on silica gel (hexane:ethyl acetate=20/80) to obtain the title compound (31 mg) having the following physical property values.

LC retention time (min), LC condition 3:0.72;
$^1$H-NMR (DMSO-d$_6$): δ 4.41, 5.34-5.46, 7.18, 7.75, 7.88-7.97, 8.52, 8.68.

Examples 79(1) to (4)

Amine produced in Example 10 or the corresponding amine was used instead of 1-[6-(trifluoromethyl)-3-pyridinyl]methanamine and subjected to the same procedure as in Example 79 to obtain a product of the present invention having the following physical property values.

Example 79(1)

1-[4-(1-amino-2,2,2-trifluoroethyl)-2,6-dichlorophenyl]-3-{[5-(trifluoromethyl)-2-pyridinyl]methyl}urea TLC: Rf 0.50 (hexane:ethyl acetate=1:2);
$^1$H-NMR (CD$_3$OD): δ 4.61, 5.37-5.45, 7.63-7.66, 7.69, 8.11-8.14, 8.83.

Example 79(2)

1-[4-(1-amino-2,2,2-trifluoroethyl)-2,6-dichlorophenyl]-3-[(5-chloro-2-pyridinyl)methyl]urea LC retention time (min), LC condition 3: 0.66;
$^1$H-NMR (DMSO-d$_6$): δ 4.38, 5.42-5.50, 7.14, 7.39, 7.75, 7.94, 8.54-8.56.

Example 79(3)

1-[4-(1-amino-2,2,2-trifluoroethyl)-2,6-dichlorophenyl]-3-(4-fluorobenzyl)urea

LC retention time (min), LC condition 3: 0.74;
$^1$H-NMR (DMSO-d$_6$): δ 4.26, 5.30-5.40, 6.98, 7.12-7.18, 7.30-7.35, 7.73, 8.29.

Example 79(4)

1-[4-(1-amino-2,2,2-trifluoroethyl)-2,6-dichlorophenyl]-3-{[2-(trifluoromethyl)-1,3-thiazole-5-yl]methyl}urea LC retention time (min), LC condition 3: 0.74;
$^1$H-NMR (DMSO-d$_6$): δ 4.54, 5.28-5.40, 7.28, 7.74, 7.97, 8.55.

Comparative Example 1

1-[4-(1,1,1-trifluoro-2-hydroxy-2-propanyl)phenyl]-3-{[5-(trifluoromethyl)-2-pyridinyl]methyl}urea

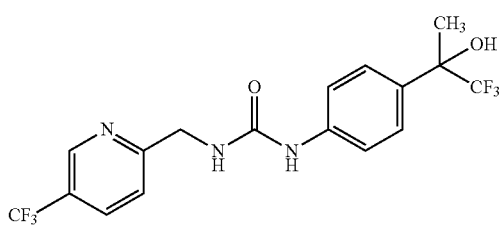 [SMILES: CC(O)(c1ccc(NC(=O)NCc2ccc(C(F)(F)F)cn2)cc1)C(F)(F)F]

The compound produced in Example 2 instead of the compound produced in Example 4 was used and subjected to the same procedure as in Example 5 to obtain the title compound having the following physical property values.
TLC: Rf 0.25 (hexane:ethyl acetate=1:1);
$^1$H-NMR (DMSO-$d_6$): δ 1.63, 4.49, 6.42, 6.86, 7.41, 7.57, 8.18, 8.90.

Comparative Example 2

N-(2-bromo-4,6-dichlorophenyl)-2-(4-fluorophenyl)acetamide (Example 1g of Patent Literature 1)

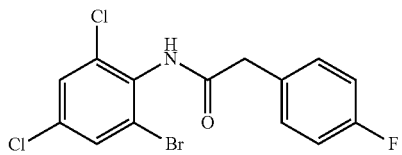 [SMILES: O=C(Cc1ccc(F)cc1)Nc1c(Cl)cc(Cl)cc1Br]

To a toluene solution (8 mL) of 2-bromo-4,6-dichloroaniline (1 g) (CAS registry number: 697-86-9), 4-fluorophenyl acetyl chloride (788 mg) was added, followed by stirring at 90° C. overnight. The reaction mixture was cooled to room temperature, and precipitate was filtered. The precipitate was washed with toluene and then dried under reduced pressure at 50° C. to obtain the title compound (1.28 g) having the following physical property values.
TLC: Rf 0.43 (hexane:ethyl acetate=1:1);
$^1$H-NMR (CD$_3$OD): δ 3.72, 7.02-7.08, 7.38-7.43, 7.58, 7.69.

The advantageous effects of the compound of the present invention can be demonstrated by the below-mentioned experiments, but not limited thereto.

(1) Biological Example 1: Opening Action with Respect to KCNQ2/3 Channel by Depolarization Stimulation Human KCNQ2/3 expression cells (CHO-DHFR-cells) were seeded in each well of 384 well plate (collagen-coated, black, clear bottom) at 0.5×10$^4$ cells/50 μL per well, and cultured in a MEM ALPHA medium (containing 10 vol % inactivated (56° C., 30 min) Fetal Bovine Serum and 100 IU/mL Penicillin—100 μg/mL Streptomycin—2 mM L-Glutamine) at 37° C. in 5% CO$_2$ for 18 to 24 hours. The medium in the plate was removed. Then, incubation (room temperature, 60 minutes, light-shielded) was carried out in a loading buffer (prepared by the method described in the manual of FluxOR Thallium Detection Kit (Invitrogen, F10016, F10017)). KCNQ2/3 channel opening action (thallium influx into cells) by the depolarization stimulation (5 mM potassium and 0.5 mM thallium) was measured by FLIPR TETRA (Molecular Devices). The compound of the present invention had been treated five minutes before the depolarization stimulation, and the reaction induced by the depolarization stimulation was measured over time for 180 seconds. The channel opening action of the compound of the present invention was evaluated based on the change amount of the fluorescence intensity from the time before the depolarization stimulation to the time after the passage of 180 seconds. Thus, the concentration (ECrtg50) satisfying 50% of the fluorescence intensity change of maximum reaction (at the time of 10 μM-treatment) of retigabine under this experiment condition was calculated.

The KCNQ2/3 channel opening action of the compound of the present invention showed 100 μM or less in terms of the ECrtg50 value. Table 1 shows the opening action (ECrtg50 values) with respect to the KCNQ2/3 channel of the following compounds as representative examples of the compound of the present invention. As is apparent from Table 1, the compound of the present invention showed a strong opening action with respect to the KCNQ2/3 channel. On the other hand, the ECrtg50 value of the comparative compound 1 was >10 μM. This shows that it is essential for improvement of the KCNQ opening activity of the compound of the present invention that at least one of $R^4$ and $R^5$ in the general formula (I) is a substituent such as halogen.

Furthermore, in the above-mentioned method, when expression cells of the human KCNQ4 or human KCNQ5 are used instead of the human KCNQ2/3 expression cells and the above-mentioned conditions are appropriately changed based on the ordinary knowledge of a person skilled in the art, the opening action with respect to the human KCNQ4 channel or the human KCNQ5 channel can be measured.

TABLE 1

| Compound | KCNQ2/3 ECrtg50 (μM) |
| --- | --- |
| Example 5 (3) | 0.5 |
| Example 5 (4) | 0.003 |
| Example 5 (5) | 0.3 |
| Example 5 (6) | 0.4 |
| Example 5 (7) | 0.5 |
| Example 5 (8) | 0.001 |
| Example 5 (9) | 0.3 |
| Example 5 (10) | 0.0003 |
| Example 5 (11) | 0.07 |
| Example 5 (12) | 2.9 |
| Example 5 (13) | 0.6 |
| Example 5 (15) | 2.3 |
| Example 5 (16) | 0.01 |
| Example 5 (17) | 0.003 |
| Example 5 (19) | 0.1 |
| Example 5 (20) | 0.5 |
| Example 5 (21) | 0.07 |
| Example 5 (22) | 0.7 |
| Example 13 | 0.01 |
| Example 22 (1) | 0.06 |
| Example 22 (2) | 0.5 |
| Example 22 (3) | 0.2 |
| Example 22 (5) | 0.8 |
| Example 22 (15) | 0.2 |
| Example 22 (16) | 0.004 |
| Example 23 | 0.01 |
| Example 25 (1) | 1.4 |
| Example 25 (2) | 0.3 |

TABLE 1-continued

| Compound | KCNQ2/3 ECrtg50 (μM) |
|---|---|
| Example 25 (5) | 0.6 |
| Example 25 (6) | 0.06 |
| Example 26 | 0.04 |
| Example 32 (1) | 0.007 |
| Example 32 (3) | 0.5 |
| Example 32 (4) | 0.2 |
| Example 33 | 0.04 |
| Example 35 (1) | 0.008 |
| Example 35 (3) | 0.3 |
| Example 36 | 0.03 |
| Example 43 (1) | 0.4 |
| Example 49 | 0.6 |
| Example 50 (1) | 0.06 |
| Example 50 (2) | 0.03 |
| Example 50 (4) | 0.05 |
| Example 50 (6) | 0.06 |
| Example 50 (7) | 0.04 |
| Example 60 | 1.7 |
| Example 62 | 0.06 |
| Example 67 | 3.5 |
| Example 71 | 0.2 |
| Example 75 | 0.4 |
| Example 79 (1) | 1.6 |
| Example 79 (4) | 0.3 |
| Comparative Example 1 | >10 |
| Comparative Example 2 | 0.2 |

(2) Biological Example 2: Relaxing Action on Urinary Bladder Extracted from Rat

Female Jcl Wistar rats (CLEA Japan, Inc., body weight in use: 170 to 200 g) were anesthetized by intraperitoneal administration of about 40 mg/kg of pentobarbital (Somnopentyl, Schering Plough Animal Health Corporation), and killed by bloodletting, followed by abdominal incision to extract the urinary bladder. Immediately, the extracted urinary bladder was immersed in ice-cooled Krebs buffer (Krebs Ringer bicarbonate buffer (Sigma-Aldlich Co.) containing sodium hydrogencarbonate (final concentration: 15 mM) and calcium chloride (final concentration: 2.5 mM)) which had been saturated with a mixed gas (95% $O_2$, 5% $CO_2$).

The urinary bladder bodies were cut in the longitudinal direction to prepare strip specimens (about 10×3 mm) on ice. Immediately, the prepared specimens were suspended in a Magnus tube with 500 mg of tension loaded. The tube was filled with Krebs buffer (37° C.) aerated with a mixed gas. Note here that specimens were prepared within 24 hours after extraction of the tissue.

Change of tension of the specimens was recorded in data collection system (NR-1000, KEYENCE CORPORATION) using a Magnus system equipped with isometric transducer (UFER UM-203, Iwashiya Kishimoto Medical Instruments) and an amplifier (UFER AP-5, Iwashiya Kishimoto Medical Instruments), and displayed on the computer via recorder analysis software WAVE THERMO 1000 (KEYENCE CORPORATION). When one hour or more had passed after the specimen was suspended, 2.5M KCl was added so that the final concentration became 100 mM, specimens showing contraction reaction were used.

Carbachol (a contraction-inducing substance) at the concentration of contraction of 1 μM was used to induce contraction. The substances were arbitrarily assigned in groups so that difference in the degree of contraction was not generated between groups and the specimens harvested from the same individual did not belong to the same group. After the contraction reaction was stabilized, a physiological salt solution or the compound of the present invention was added in a cumulative manner from low concentration such that the final concentration became 1, 10, 100 nM, 1 and 10 μM.

The tension (mg) of the extracted urinary bladder was employed as an evaluation parameter. The tension was read by using analysis software WAVE THERMO 1000. Tension after addition of the contraction-inducing substance was set to 0%. The change rate of the tension after addition of the compound of the present invention relative to the tension after addition of the contraction-inducing substance was defined as tension change rate (%). The tension change rate (%) was adopted as an evaluation indicator. The tension change rate (%) is calculated from the following formula.

Tension change rate (%)={Tension after addition of compound of the present invention and the like (mg)−Tension before addition of contraction-inducing substance (mg)}/{Tension after addition of contraction-inducing substance (mg)−Tension before addition of contraction-inducing substance (mg)}×100−100

The value at which the tension change rate (%) was −20% was calculated as $IC_{20}$, and the value was adopted as an indicator of the relaxing action of the extracted urinary bladder.

Table 2 shows $IC_{20}$ values in the rat Magnus test of the following compounds as representative examples of the compound of the present invention. As is apparent from Table 2, the compound of the present invention had relaxing action with respect to the extracted rat urinary bladder. Consequently, the compound of the present invention is useful as a therapeutic agent for overactive urinary bladder.

TABLE 2

| Compound | Rat Magnus test $IC_{20}$ (uM) |
|---|---|
| Example 22 (1) | 0.3 |
| Example 22 (2) | 0.4 |
| Example 22 (3) | 0.3 |
| Example 22 (5) | 0.3 |
| Example 23 | 0.1 |
| Example 25 (1) | 0.6 |
| Example 25 (2) | 0.2 |
| Example 25 (5) | 0.5 |
| Example 26 | 0.2 |
| Example 32 (1) | 0.02 |
| Example 32 (3) | 0.1 |
| Example 32 (4) | 0.2 |
| Example 33 | 0.03 |
| Example 35 (1) | 0.02 |
| Example 35 (3) | 0.1 |
| Example 36 | 0.01 |

(3) Solubility Test

A calibration curve solution was prepared by diluting a test substance (10 mM DMSO solution) with acetonitrile and adding acetonitrile including an internal standard substance (candesartan) so as to be 0.1, 0.4, and 2 μM.

Sample solution was prepared as follows: 5 μL of the compound of the present invention (10 mM DMSO solution) was added to 495 μL of the Pharmacopoeia of Japan elution test second solution (pH=6.8), and the resulting mixture was stirred at room temperature for five hours. Then, the solution was placed into a solubility filter plate and subjected to suction filtration. The filtrate (20 μL) was diluted with acetonitrile, followed by adding acetonitrile including an internal standard substance (CANDESARTAN).

The calibration curve and sample solutions in the amount of 5 μL were infused into LC-MS/MS (Discovery Max manufactured by Thermo Scientific) and subjected to quantitation (quantitation range: 5 to 100 μM). The solubility was set to <5 μM when the value was less than the quantitation range, and the solubility was set to 100 μM when the value was more than the quantitation range.

The results are shown in Table 3. As is apparent from Table 3, the compounds shown in Table 3 as the representative examples of the compound of the present invention showed excellent solubility. On the contrary, the solubility of Comparative Example 2 (Example 1g of Patent Literature 1) was not more than the detection limit (<5 μM), showing that the solubility of Comparative Example 2 was low.

TABLE 3

| Compound | Solubility (uM) |
| --- | --- |
| Example 5 (4) | 79 |
| Example 5 (5) | 93 |
| Example 5 (6) | 94 |
| Example 5 (9) | 91 |
| Example 5 (13) | 81 |
| Example 5 (15) | 90 |
| Example 5 (19) | 76 |
| Example 5 (20) | 100 |
| Example 5 (22) | 85 |
| Example 13 | 69 |
| Example 22 (1) | 77 |
| Example 22 (2) | 89 |
| Example 22 (3) | 81 |
| Example 22 (5) | 91 |
| Example 23 | 46 |
| Example 25 (1) | 96 |
| Example 25 (2) | 86 |
| Example 25 (5) | 98 |
| Example 25 (6) | 40 |
| Example 26 | 59 |
| Example 32 (1) | 100 |
| Example 32 (3) | 100 |
| Example 32 (4) | 77 |
| Example 33 | 91 |
| Example 35 (1) | 100 |
| Example 35 (3) | 87 |
| Example 36 | 44 |
| Example 43 (1) | 89 |
| Example 50 (1) | 82 |
| Example 50 (2) | 41 |
| Example 62 | 71 |
| Example 79 (1) | 87 |
| Comparative Example 2 | <5 |

(4) Evaluation of Stability in Human Liver Microsome

A test compound (10 mmol/L DMSO solution, 5 μL) was diluted with 50% acetonitrile aqueous solution (195 μL) to prepare 0.25 mmol/L solution.

To a reactor vessel which had been warmed to 37° C. in advance, 0.5 mg/mL of human liver microsome (Xenotech) and 245 μL of 0.1 M phosphate buffer solution (pH 7.4) including NADPH-Co-factor (BD Biosciences) were added, followed by preincubation for five minutes. Then, the above-mentioned test compound solution (5 μL) was added so as to start reaction (final concentration: 5 μmol/L). Immediately after the start, 20 μL was harvested and added to 180 μL of acetonitrile including an internal standard substance (warfarin) to stop the reaction. This solution (20 μL) was stirred with 180 μL of 50% acetonitrile aqueous solution on a plate equipped with a deproteinization filter. Then, the resulting mixture solution was subjected to suction filtration. The filtrate was adopted as a standard sample.

The above-mentioned reaction solution was incubated at 37° C. for 15 minutes, and 20 μL of the solution was added to 180 μL of cooled acetonitrile (including warfarin that is an internal standard substance) to stop the reaction. This solution (20 μL) was stirred with 180 μL of 50% acetonitrile aqueous solution on a plate equipped with a deproteinization filter, and then the resulting mixture solution was subjected to suction filtration. The filtrate was adopted as a reaction sample.

Residual rate (%) was obtained as follows: 1 μL of the sample solution was infused into LC-MS/MS (Discovery Max manufactured by Thermo Scientific), and a quotient obtained by dividing a peak area ratio of the reaction sample (peak area of test compound/peak area of internal standard substance) was divided by the peak area ratio of the standard sample was multiplied by 100.

The results are shown in Table 4. As is apparent from Table 4, the compounds shown in Table 4 shown as the representative examples of the compound of the present invention showed high stability with respect to a human liver microsome, showing that the compound is excellent in the metabolic stability.

TABLE 4

| Compound | Residual rate (%) |
| --- | --- |
| Example 5 (13) | 75 |
| Example 5 (15) | 97 |
| Example 5 (19) | 100 |
| Example 5 (20) | 91 |
| Example 22 (1) | 100 |
| Example 22 (2) | 100 |
| Example 22 (3) | 98 |
| Example 22 (5) | 99 |
| Example 22 (15) | 93 |
| Example 22 (16) | 94 |
| Example 23 | 100 |
| Example 25 (1) | 78 |
| Example 25 (2) | 80 |
| Example 25 (5) | 87 |
| Example 25 (6) | 73 |
| Example 26 | 64 |
| Example 32 (3) | 100 |
| Example 32 (4) | 100 |
| Example 33 | 100 |
| Example 35 (1) | 100 |
| Example 35 (3) | 100 |
| Example 36 | 100 |
| Example 50 (1) | 96 |
| Example 50 (4) | 100 |
| Example 60 | 98 |
| Example 75 | 100 |
| Example 79 (1) | 82 |

(5) Evaluation of Action on hERG IKr Current

Using HEK293 cell overexpressing a human ether-a-go-go-related gene (hERG), the maximum tale current of the hERG IKr current induced by redepolarization pulse subsequent to depolarization pulse was measured by a patch-clamp method. The change rate (inhibition rate) of the 10 minutes after application of the test compound, with respect to the maximum tale current before application of the test compound, was calculated (see, Biophysical Journal, Vol. 74, 230-241 (1998)). The results are shown in Table 5. As is apparent from Table 5, the compounds shown in Table 5 as the representative examples of the compounds of the present invention showed that the 50% inhibitory activity of hERG channel thereof were >10 μM and less possibility of inducing Q-T extension due to drug, showing that the compounds the present invention had excellent safety.

TABLE 5

| Compound | IC$_{50}$ (uM) |
|---|---|
| Example 22 (1) | >10 |
| Example 22 (2) | >10 |
| Example 22 (3) | >10 |
| Example 22 (5) | >10 |
| Example 23 | >10 |
| Example 25 (1) | >10 |
| Example 25 (2) | >10 |
| Example 25 (5) | >10 |
| Example 26 | >10 |
| Example 32 (3) | >10 |
| Example 32 (4) | >10 |
| Example 33 | >10 |
| Example 35 (3) | >10 |
| Example 36 | >10 |
| Example 50 (1) | >10 |
| Example 79 (1) | >10 |

Formulation Example

Representative formulation examples to be used in the present invention are shown as follows.

Formulation Example 1

The following components were mixed with each other in a usual method and punched out to obtain 10,000 tablets each containing 10 mg of the active ingredient.
1-{2,6-dichloro-4-[(2R)-1,1,1-trifluoro-2-hydroxy-2-propanyl]phenyl}-3-{[5-(trifluoromethyl)-2-pyridinyl]methyl}urea (100 g);
carboxymethylcellulose calcium (disintegrating agent) (20 g);
magnesium stearate (lubricant) (10 g);
microcrystalline cellulose (870 g).

Formulation Example 2

The following components were mixed with each other in a usual method and filtered with a dust removal filter, and 5 mL each of the filtrate was filled into ampoules. The ampoules were heated and sterilized in an autoclave, thereby obtaining 10,000 ampoules each containing 20 mg of the active ingredient.

1-{2,6-dichloro-4-[(2R)-1,1,1-trifluoro-2-hydroxy-2-propanyl]phenyl}-3-{[5-(trifluoromethyl)-2-pyridinyl]methyl}urea (200 g);
mannitol (2 kg);
distilled water (50 L).

INDUSTRIAL APPLICABILITY

The compound of the present invention has sufficiently low toxicity, and can be used safely as a pharmaceutical agent, and useful as a therapeutic agent for KCNQ2-5 channel-related diseases.

The invention claimed is:

1. A pharmaceutical composition comprising 1-[(5-chloro-2-pyridinyl)methyl]-3-{2,6-dichloro-4-[(2S)-1,1,1-trifluoro-2-hydroxy-2-propanyl]phenyl}urea, or a pharmaceutically acceptable salt thereof, and a pharmaceutically acceptable carrier.

2. The pharmaceutical composition according to claim 1, which is a therapeutic agent for dysuria.

3. The pharmaceutical composition according to claim 2, wherein the dysuria is overactive urinary bladder.

4. A method for treating dysuria, the method comprising: administering an effective amount of 1-[(5-chloro-2-pyridinyl)methyl]-3-{2,6-dichloro-4-[(2S)-1,1,1-trifluoro-2-hydroxy-2-propanyl]phenyl}urea, or a pharmaceutically acceptable salt thereof, to a mammal.

5. The method according to claim 4, wherein the dysuria is overactive urinary bladder.

6. A pharmaceutical composition comprising 1-[(5-chloro-2-pyridinyl)methyl]-3-{2,6-dichloro-4-[(2 S)-1,1,1-trifluoro-2-hydroxy-2-propanyl]phenyl}urea and a pharmaceutically acceptable carrier.

7. The pharmaceutical composition according to claim 6, which is a therapeutic agent for a dysuria.

8. The pharmaceutical composition according to claim 7, wherein the dysuria is overactive urinary bladder.

9. A method for treating dysuria, the method comprising: administering an effective amount of 1-[(5-chloro-2-pyridinyl)methyl]-3-{2,6-dichloro-4-[(2S)-1,1,1-trifluoro-2-hydroxy-2-propanyl]phenyl}urea to a mammal.

10. The method according to claim 9, wherein the dysuria is overactive urinary bladder.

11. A method for treating overactive urinary bladder, the method comprising: administering an effective amount of 1-[(5-chloro-2-pyridinyl)methyl]-3-{2,6-dichloro-4-[(2S)-1,1,1-trifluoro-2-hydroxy-2-propanyl]phenyl}urea to a mammal.

* * * * *

UNITED STATES PATENT AND TRADEMARK OFFICE
CERTIFICATE OF CORRECTION

PATENT NO. : 10,196,358 B2
APPLICATION NO. : 15/671428
DATED : February 5, 2019
INVENTOR(S) : Kentaro Yashiro et al.

Page 1 of 1

It is certified that error appears in the above-identified patent and that said Letters Patent is hereby corrected as shown below:

Column 100, Claim 6, Line 32, "[(2 S)]" should be -- [(2S)] --.

Column 100, Claim 7, Line 36, "for a dysuria" should be -- for dysuria --.

Signed and Sealed this
Sixth Day of August, 2019

Andrei Iancu
*Director of the United States Patent and Trademark Office*